United States Patent
Boral et al.

(10) Patent No.: US 9,266,869 B2
(45) Date of Patent: Feb. 23, 2016

(54) SUBSTITUTED DIALKYL(OXIDO)-LAMBDA 4-SULFANYLIDENE NICOTINAMIDE DERIVATIVES AS KINASE INHIBITORS

(71) Applicant: Allergan, Inc., Irvine, CA (US)

(72) Inventors: Sougato Boral, Santa Ana, CA (US); Shimiao Wang, Irvine, CA (US); Thomas Malone, Irvine, CA (US); Julie Wurster, Irvine, CA (US); Jie Shen, Irvine, CA (US); Michael Robinson, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/565,660

(22) Filed: Dec. 10, 2014

(65) Prior Publication Data
US 2015/0166521 A1 Jun. 18, 2015

Related U.S. Application Data

(60) Provisional application No. 61/915,172, filed on Dec. 12, 2013.

(51) Int. Cl.
| | |
|---|---|
| *C07D 413/12* | (2006.01) |
| *C07D 405/12* | (2006.01) |
| *C07D 409/14* | (2006.01) |
| *C07D 213/82* | (2006.01) |
| *C07D 401/12* | (2006.01) |
| *C07D 405/14* | (2006.01) |

(52) U.S. Cl.
CPC ............ *C07D 413/12* (2013.01); *C07D 213/82* (2013.01); *C07D 401/12* (2013.01); *C07D 405/12* (2013.01); *C07D 405/14* (2013.01); *C07D 409/14* (2013.01)

(58) Field of Classification Search
None
See application file for complete search history.

(56) References Cited

U.S. PATENT DOCUMENTS

| | | | | |
|---|---|---|---|---|
| 7,915,443 B2 * | 3/2011 | Wurster et al. | ................ | 560/317 |
| 8,143,410 B2 * | 3/2012 | Spada et al. | ................ | 546/316 |
| 8,558,002 B2 * | 10/2013 | Boral et al. | ................ | 546/316 |

FOREIGN PATENT DOCUMENTS

| | | |
|---|---|---|
| WO | 2008-061236 A2 | 5/2008 |
| WO | 2013-062843 A1 | 5/2013 |

OTHER PUBLICATIONS

Adamis, A., et al., Inhibition of Platelet-Derived Growth Factor B Signaling Enhances the Efficacy of Anti-Vascular Endothelial Growth Factor Therapy in Multiple Models of Ocular Neovascularization, Amer. Journal Pathology 2006, 168: 2036-2053, 6.
Aora, A., et al., Role of Tyrosine Kinase Inhibitors in Cancer Therapy, J. Pharma. & Exp. Therapeutics 2015, 315: 971-979, 3.
Baraket, M., et al., VEGF inhibitors for the treatment of neovascular age-related macular degeneration, Informa Healthcare, 2009, 637-646.
Berge, S., et al., Pharmaceutical Salts, J. Pharma. Sci. 1977, 66: 1-19, 1.
Bergers, G., et al., Benefits of targeting both pericytes and endothelial cells in the tumor vasculature with kinase inhibitors, J. Clin. Invest. 2003, 111: 1287-1295, 9.
Chappelow, A., et al., Neovascular Age-Related Macular Degeneration Potential Therapies, Drugs 2008, 68: 1029-1036, 8.
Cowan-Jacob, S.W., Structural biology of protein tyrosine kinases, Cell. Mol. Life Sci. 2006, 63: 2608-2625.
DePinho, R., et al., Coactivation of Receptor Tyrosine Kinases Affects the Response of Tumor Cells to Targeted Therapies, Science 2007, 318: 287-291.
Edelmen, J., et al., Corticosteroids inhibit VEGF-induced vascular leakage in a rabbit model of blood-retinal and blood-aqueous barrier breakdown, Exp. Eye Res. 2005, 80: 249-258.
Gould, P., Salt selection for basic drugs, Int'l J. Pharma. 1986, 33: 201-217.
Heidenreich, R., et al., Angiogenesis: The New Potential Target for the Therapy of Psoriasis?, Drug News Perspect 2008, 21: 97-105, 2.
Higuchi, T., et al., Pro-drugs as Novel Drug Delivery Systems, ACS Symposium Series 14, 1975, pp. 1-15.
Ni, Z., et al., Emerging Pharmacologic Therapies for Wet Age-Related Macular Degeneration, Ophthalmologica 2009, 223: 401-410.
Perez-Santonja, J., et al., Inhibition of Corneal Neovascularization by Topical Bevacizumab (Anti-VEGF) and Sunitinib (Anti-VEGF and Anti-PDGF) in an Animal Model, American J. Ophthal. 2010, 150: 519-529, 4.
Smith, J., et al., Expression of vascular endothelial growth factor and its receptors in rosacea, Br. J. Ophthalmol. 2007, 91: 226-229.
Zhang, X., et al., Vascular endothelial growth factor-A: A multifunctional molecular player in diabetic retinopathy, Int'l. J. Biochem. & Cell Biol. 2009, 41: 2368-2371.
Stahl, P. et al., Handbook of Pharmaceutical Salts, Properties, Selection, and Use, 2002, 329-345.
Roche, Edward, Application of Physical Organic Concepts to in Vitro and in Vivo Lability Design of Water Soluble Prod rugs, Chap. 4: 121-163, in Bioreversible Carriers on Drug Design: Theory & Application, 1987.
Anderson, B. et al., The Practice of Medicinal Chemistry, 3rd Ed. pp. 1-32, 1996.

* cited by examiner

*Primary Examiner* — Timothy R Rozof
(74) *Attorney, Agent, or Firm* — Jonathan Bass

(57) ABSTRACT

The present invention relates to organic molecules capable of modulating tyrosine kinase signal transduction in order to regulate, modulate and/or inhibit abnormal cell proliferation.

18 Claims, No Drawings

SUBSTITUTED DIALKYL(OXIDO)-LAMBDA4-SULFANYLIDENE NICOTINAMIDE DERIVATIVES AS KINASE INHIBITORS

CROSS REFERENCE TO RELATED APPLICATIONS

This application claims priority to and the benefit of U.S. Provisional Patent Application No. 61/915,172, filed Dec. 12, 2013, the disclosure of which is hereby incorporated by reference in its entirety.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The receptor-type tyrosine kinases (RTKs) comprise a large family of transmembrane receptors with diverse biological activities. The intrinsic function of RTKs is activated upon ligand binding, which results in phosphorylation of the receptor and multiple cellular substrates, and subsequently in a variety of cellular responses. The non-receptor tyrosine kinases represent a collection of cellular enzymes which lack extracellular and transmembrane sequences. A more detailed discussion of receptor and non-receptor tyrosine kinases is provided in Cowan-Jacob Cell Mol. Life Sci., 1996, 63, 2608-2625 which is incorporated herein by reference.

There are a number of examples where RTK kinases, have been found to be involved in cellular signaling pathways leading to pathological conditions, including exudative age-related macular degeneration (Ni et al. Opthalmologica 2009 223 401-410; Chappelow et al. Drugs 2008 68 1029-1036), diabetic retinopathy (Zhang et al., Int. J. Biochem. Cell Biol. 2009 41 2368-2371), cancer (Aora et al. J. Path. Exp. Ther. 2006, 315, 971), psoriasis (Heidenreich et al Drug News Perspective 2008 21 97-105) and rosacea (Smith, J. R., V. B. Lanier, et al. *Br J Ophthalmol* 2007, 91(2): 226-229). In ophthalmic diseases such as exudative age-related macular degeneration and diabetic retinopathy aberrant activation of VEGF receptors can lead to abnormal blood vessel growth. The importance of VEGFR signaling in the exudative age-related macular degeneration disease process is evident by the clinical success of multiple anti-VEGF targeting agents including Lucentis®, Avastin®, and EYLEA™ (Barakat et al., Expert Opin. Investig. Drugs 2009, 18, 637). Recently it has been suggested that inhibition of multiple RTK signaling pathways may provide a greater therapeutic effect than targeting a single RTK signaling pathway. For example in neovascular ocular disorders such as exudative age-related macular degeneration and diabetic retinopathy the inhibition of both VEGFR and PDGFRβ may provide a greater therapeutic effect by causing regression of existing neovascular blood vessels present in the disease (Adamis et al., Am. J. Pathol. 2006 168 2036-2053). In cancer inhibition of multiple RTK signaling pathways has been suggested to have a greater effect than inhibiting a single RTK pathway (DePinho et al., Science 2007 318 287-290; Bergers et al. J. Clin Invest. 2003 111 1287-1295).

WO 2013/062843 A1 refers to pyridine-sulfoximines as tyrosine kinase inhibitors.

WO 2008/061236 A2 refers to sulfoximine-nicotine derivatives as kinase inhibitors and their preparation, pharmaceutical compositions and use in the treatment of proliferative diseases.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

The above references are hereby incorporated by reference in their entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction by blocking the VEGF and/or PDGF receptors. Such compounds are useful for the treatment of diseases related to unregulated tyrosine kinase signal transduction, including vascular proliferative disorders such as diabetic retinopathy, age-related macular degeneration and retinopathy of prematurity.

In one illustrative embodiment, the compounds of the present invention have the following general formula I:

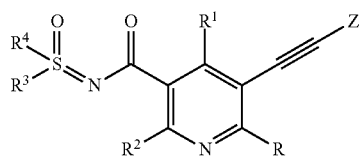

wherein
Z is

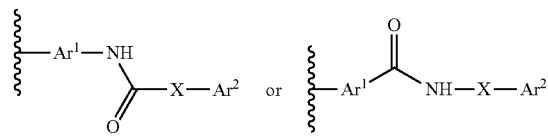

wherein X is absent or X is selected from the group consisting of O, NH and $CH_2$;
R is selected from the group consisting of hydrogen, amino and lower alkyl:
$R^1$ is selected from the group consisting of hydrogen, halogen, lower alkyl, $CF_3$,
$R^2$ is selected from the group consisting of hydrogen, amino and lower alkyl,
$R^3$ and $R^4$ are independently selected from the group consisting of hydrogen, $C_1$ to $C_8$ alkyl, $(CR^5R^6)_aC(O)OR^7$, $(CR^5R^6)_a$ $OR^7$, $(CR^5R^6)_aN(R^5)C(O)R^7$, $(CR^5R^6)_aC(O)N$ $(R^7)_2$, $(CR^5R^6)_aN(R^5)C(O)OR^7$, $(CR^5R^6)_aN(R^5)C(O)N$ $(R^7)_2$, $(CR^5R^6)_aN(R^7)_2$, wherein $N(R^7)_2$ may be taken together to form a heterocyclic ring optionally substituted with one or more of $R^5$ and wherein when one of $R^3$ and $R^4$ is selected from the group consisting of, $(CR^5R^6)_aC(O)OR^7$, $(CR^5R^6)_a$ $OR^7$, $(CR^5R^6)_aC(O)N(R^7)$ and, $(CR^5R^6)_aN(R^7)_2$, then the other may not be aryl, or;
$R^3$ and $R^4$ may be taken together with the sulfur atom to form a 4 to 7 membered carbocyclic or heterocyclic ring containing one or more heteroatoms optionally substituted by one or more of $R^9$.
$R^5$ is selected from the group consisting of hydrogen, $C_1$ to $C_8$ alkyl, fluoro, hydroxy, hydroxymethyl, $COCH_3$, $CH_2CH_2OH$, $CH_2CH_2CH_2OH$ and $CH_2CH_2OCH_2CH_2OH$;
$R^6$ is selected from the group consisting of hydrogen, $C_1$ to $C_8$ alkyl, hydroxy and fluoro;
$R^7$ is selected from the group consisting of hydrogen, $C_1$ to $C_8$ alkyl, fluoro, hydroxy, hydroxymethyl, $COCH_3$, $CH_2CH_2OH$ and $CH_2CH_2CH_2OH$;
$R^9$ is selected from the group consisting of hydrogen, $C_1$ to $C_8$ alkyl, $(CR^5R^6)_aC(O)OR^7$, $(CR^5R^6)_aOR^7$, $(CR^5R^6)_aN(R^5)$ $C(O)R^7$, $(CR^5R^6)_aC(O)N(R^7)_2$, $(CR^5R^6)_aN(R^5)C(O)OR^7$ $(CR^5R^6)_aN(R^5)C(O)N(R^7)_2$, $(CR^5R^6)_aN(R^7)_2$, $(CR^5R^6)_aC$ $(O)N(R^5)(CR^5R^6)_aC(O)OR^7$, $(CR^5R^6)_aC(O)N(R^5)$ $(CR^5R^6)_a$ $C(O)N(R^7)_2$, wherein $N(R^7)_2$ may be taken together to form a heterocyclic ring containing one or more heteroatoms;
$Ar^1$ and $Ar^2$ are independently selected from the group consisting of

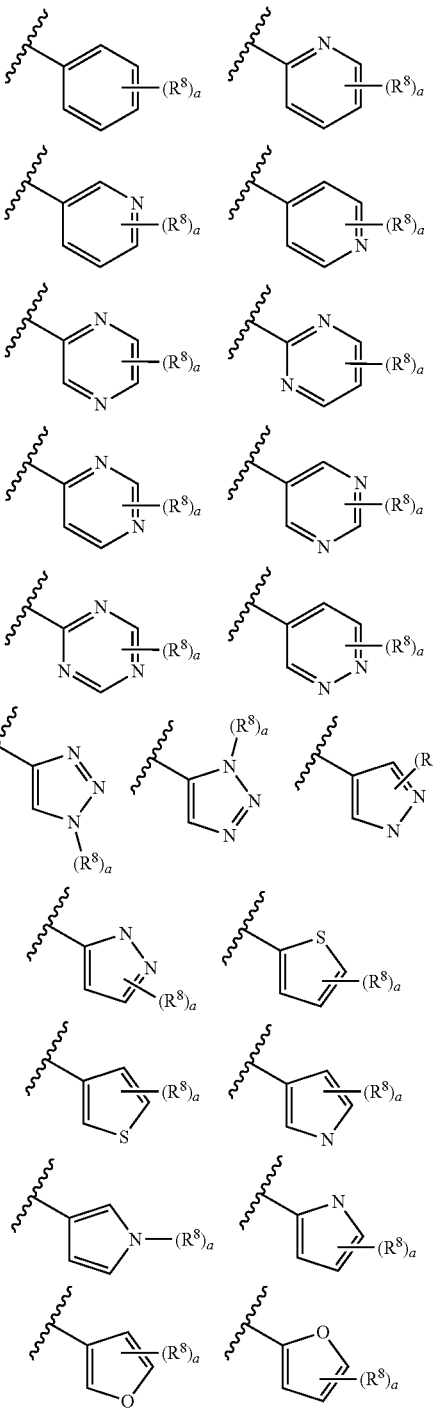

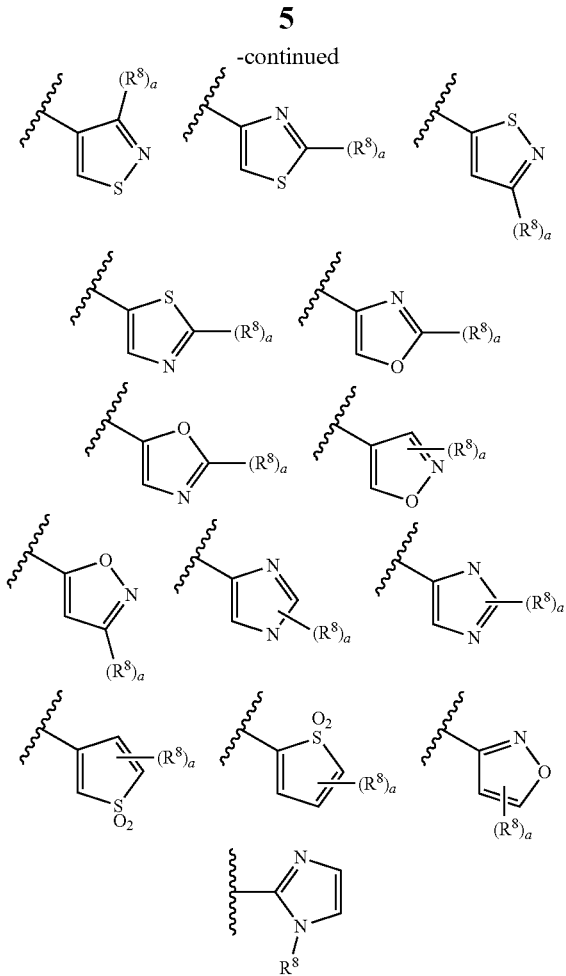

wherein R⁸ is selected from the group consisting of hydrogen, alkyl, e.g. lower alkyl, amino, hydroxyl, alkoxy, e.g. lower alkyloxy. halogen and $CF_3$ and a is 0 or an integer of from 1 to 4.

Most preferably $Ar^1$ is selected from the group consisting of phenyl,

Most preferably $Ar^2$ is selected from the group consisting of
phenyl,
furanyl,
oxazoyl
diazinyl and mono and disubstituted derivatives thereof wherein the substituent may be halogen, e.g. fluoro or chloro, alkyl, e.g. lower alkyl, i.e. methyl or ethyl; alkyloxy, e.g. lower alkyloxy, e.g. methyloxy or t-butyloxy; trifluoromethyl, etc.

For example, $Ar^2$ may be selected from the group consisting of
3-methylfuranyl,
2-fluoro 5-methylphenyl,
4-chloro 5-t-butylphenyl,
3-methoxyphenyl and
5-butyloxazoyl.

Preferably $R^2$ is H.

Most preferably said compound is selected from the group consisting of

N-[dimethyl(oxido)-λ⁴-sulfanylidene]-5-({3-[(3-methyl-2-furoyl)amino]phenyl}ethynyl)nicotinamide, 6-amino-N-[dimethyl(oxido)-λ⁴-sulfanylidene]-5-({3-[(3-methyl-2-furoyl)amino]phenyl}ethynyl)nicotinamide, 5-({3-[(3-methyl-2-furoyl)amino]phenyl}ethynyl)-N-(1-oxidotetrahydro-1H-1λ⁴-thien-1-ylidene)nicotinamide, 6-amino-5-({3-[(3-methyl-2-furoyl)amino]phenyl}ethynyl)-N-(1-oxidotetrahydro-1H-1λ⁴-thien-1-ylidene)nicotinamide, 6-amino-5-({3-[(4-chlorobenzoyl)amino]phenyl}ethynyl)-N-[dimethyl(oxido)-λ⁴-sulfanylidene]nicotinamide, 6-amino-N-[dimethyl(oxido)-λ⁴-sulfanylidene]-5-({3-[(2-fluoro-5-methylbenzoyl)amino]phenyl}ethynyl)nicotinamide, 6-amino-N-[dimethyl(oxido)-λ⁴-sulfanylidene]-5-[(3-{[(1-methyl-1H-imidazol-2-yl)carbonyl]amino}phenyl)ethynyl]nicotinamide, N-[dimethyl(oxido)-λ⁴-sulfanylidene]-5-{[3-({[(2-fluoro-5-methylphenyl)amino]carbonyl}amino)phenyl]ethynyl}nicotinamide, N-[dimethyl(oxido)-λ⁴-sulfanylidene]-5-{[3-({[(2-fluorophenyl)amino]carbonyl}amino)phenyl]ethynyl}nicotinamide, N-[dimethyl(oxido)-λ⁴-sulfanylidene]-5-{[3-({[(3-methylphenyl)amino]carbonyl}amino)phenyl]ethynyl}nicotinamide, N-[dimethyl(oxido)-λ⁴-sulfanylidene]-5-{[3-({[(4-methylphenyl)amino]carbonyl}amino)phenyl]ethynyl}nicotinamide, 6-amino-N-{[2-(3-hydroxypyrrolidin-1-yl)-2-oxoethyl](methyl)oxido-λ⁴-sulfanylidene}-5-({3-[(3-methyl-2-furoyl)amino]phenyl}ethynyl)nicotinamide, N-[(3-{4-[2-(2-hydroxyethoxy)ethyl]piperazin-1-yl}propyl)(methyl)oxido-λ⁴-sulfanylidene]-5-({3-[(3-methyl-2-furoyl)amino]phenyl}ethynyl)nicotinamide, N-[bis(3-hydroxypropyl)(oxido)-λ⁴-sulfanylidene]-5-({3-[(3-methyl-2-furoyl)amino]phenyl}ethynyl)nicotinamide, 6-amino-N-[bis(3-hydroxypropyl)(oxido)-λ⁴-sulfanylidene]-5-({3-[(3-methyl-2-furoyl)amino]phenyl}ethynyl)nicotinamide, N-[bis(3-hydroxypropyl)(oxido)-λ⁴-sulfanylidene]-5-[(3-{[4-chloro-3-(trifluoromethyl)benzoyl]amino}phenyl)ethynyl]nicotinamide, N-[bis(3-hydroxypropyl)(oxido)-λ⁴-sulfanylidene]-5-({3-[(3-methylbenzoyl)amino]phenyl}ethynyl)nicotinamide, N-[bis(3-hydroxypropyl)(oxido)-λ⁴-sulfanylidene]-5-[(3-{[3-(trifluoromethyl)benzoyl]amino}phenyl)ethynyl]nicotinamide, N-[bis(3-hydroxypropyl)(oxido)-λ⁴-sulfanylidene]-5-({3-[(3-chloro-4-fluorobenzoyl)amino]phenyl}ethynyl)nicotinamide, N-[bis(3-hydroxypropyl)(oxido)-λ⁴-sulfanylidene]-5-({3-[(2-fluoro 5-methylbenzoyl)amino]phenyl}ethynyl)nicotinamide, 6-amino-N-[bis(3-hydroxypropyl)(oxido)-λ⁴-sulfanylidene]-5-({3-[(3-methoxybenzoyl)amino]phenyl}ethynyl)nicotinamide, 6-amino-N-[bis(3-hydroxypropyl)(oxido)-λ⁴-sulfanylidene]-5-[(3-{[(3-methylphenyl)amino]carbonyl}phenyl)ethynyl]nicotinamide, methyl 5-(N-{[6-amino-5-({3-[(3-methyl-2-furoyl)amino]phenyl}ethynyl)pyridin-3-yl]carbonyl}-S-methylsulfonimidoyl)pentanoate, 5-(N-{[6-amino-5-({3-[(3-methyl-2-furoyl)amino]phenyl}ethynyl)pyridin-3-yl]carbonyl}-S-m ethylsulfonimidoyl)pentanoic acid, methyl 5-(N-{[6-amino-5-({3-[(2-fluoro-5-methylbenzoyl)amino]phenyl}ethynyl)pyridin-3-yl]carbonyl}-S-methylsulfonimidoyl)pentanoate, methyl 5-(N-{[6-amino-5-({3-[(3-methylbenzoyl)amino]phenyl}ethynyl)pyridin-3-yl]carbonyl}-S-methylsulfonimidoyl)pentanoate methyl 5-[N-({6-amino-5-[(3-{[2-fluoro-5-(trifluoromethyl)benzoyl]amino}phenyl)ethynyl]pyridin-3-yl}carbonyl)-S-methylsulfonimidoyl]pentanoate, methyl 5-[N-({6-amino-5-[(3-{[3-(trifluoromethyl)benzoyl]amino}phenyl)ethynyl]pyridin-3-yl}carbonyl)-S-methylsulfonimidoyl]pentanoate, methyl 5-[N-({6-amino-5-[(3-{[4-chloro-3-(trifluoromethyl)benzoyl]amino}phenyl)ethynyl]pyridin-3-yl}carbonyl)-S-methylsulfonimidoyl]pentanoate, methyl 5-(N-{[6-amino-5-({3-[(3-methoxybenzoyl)amino]phenyl}ethynyl)pyridin-3-yl]carbonyl}-S-methylsulfonimidoyl)pentanoate, methyl 5-(N-{[6-amino-5-({3-[(3,4-dimethoxybenzoyl)amino]phenyl}ethynyl)pyridin-3-yl]carbonyl}-S-methylsulfonimidoyl)pentanoate, (S)-methyl 5-(N-{[6-amino-5-({3-[(3-methyl-2-furoyl)amino]phenyl}ethynyl)pyridin-3-yl]carbonyl}-S-methylsulfonimidoyl)pentanoate, (R)-methyl 5-(N-{[6-amino-5-({3-[(3-methyl-2-furoyl)amino]phenyl}ethynyl)pyridin-3-yl]carbonyl}-S-methylsulfonimidoyl)pentanoate, methyl 5-[N-({6-amino-5-[(3-{[(3-methylphenyl)amino]carbonyl}phenyl)ethynyl]pyridin-3-yl}carbonyl)-S-methylsulfonimidoyl]pentanoate, methyl 5-[N-({6-amino-5-[(3-{[(2-fluoro-5-methylphenyl)amino]carbonyl}phenyl)ethynyl]pyridin-3-yl}carbonyl)-S-methylsulfonimidoyl]pentanoate, methyl 5-[N-({6-amino-5-[(3-{[(5-tert-butylisoxazol-3-yl)amino]carbonyl}phenyl)ethynyl]pyridin-3-yl}carbonyl)-S-methylsulfonimidoyl]pentanoate, methyl 5-{N-[(6-amino-5-{[3-({[(2-fluoro-5-methylphenyl)amino]carbonyl}amino)phenyl]ethynyl}pyridin-3-yl)carbonyl]-S-methylsulfonimidoyl}pentanoate, methyl 5-{N-[(6-amino-5-{[3-({[(3-methylphenyl)amino]carbonyl}amino)phenyl]ethynyl}pyridin-3-yl)carbonyl]-S-methylsulfonimidoyl}pentanoate, N-[(3-hydroxypropyl)(methyl)oxido-$\lambda^4$-sulfanylidene]-5-({3-[(3-methyl-2-furoyl)amino]phenyl}ethynyl)nicotinamide, (R)—N-[(3-hydroxypropyl)(methyl)oxido-$\lambda^4$-sulfanylidene]-5-({3-[(3-methyl-2-furoyl)amino]phenyl}ethynyl)nicotinamide and (S)—N-[(3-hydroxypropyl)(methyl)oxido-$\lambda^4$-sulfanylidene]-5-({3-[(3-methyl-2-furoyl)amino]phenyl}ethynyl)nicotinamide.

6-amino-N-[(3-hydroxypropyl)(methyl)oxido-$\lambda^4$-sulfanylidene]-5-({3-[(3-methyl-2-furoyl)amino]phenyl}ethynyl)nicotinamide Compounds of formula I are useful as kinase inhibitors. As such, compounds of formula I will be useful for treating diseases related to unregulated tyrosine kinase signal transduction, for example, cancer, blood vessel proliferative disorders, fibrotic disorders, and neurodegenerative diseases. In particular, the compounds of the present invention are useful for treatment of mesangial cell proliferative disorders and metabolic diseases, pterigium, arthritis, restenosis, hepatic cirrhosis, atherosclerosis, psoriasis, rosacea, diabetis mellitus, wound healing, and neurodegenerative diseases and preferably ophthalmic diseases, i.e. diabetic retinopathy, age-related macular degeneration, retinopathy of prematurity, etc.

DETAILED DESCRIPTION OF THE INVENTION

The present invention is further directed to pharmaceutical compositions comprising a pharmaceutically effective amount of one or more of the above-described compounds and a pharmaceutically acceptable carrier or excipient, wherein said compositions are effective for treating the above diseases and conditions; especially ophthalmic diseases and conditions. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, rosacea, atherosclerosis, arthritis, and other disorders related to abnormal vasculogenesis and/or angiogenesis, such as exudative age related macular degeneration and diabetic retinopathy. The compositions of the present invention are also useful in treating pterygia, blepharoconjunctivitis, chronic allergic conjunctivitis, recurrent episcleritis, keratoconjunctivitis sicca. In addition the following dermatological indications may be treated: sun burn, eczema, psoriasis contact dermatitis Most preferably, the compounds of the present invention are useful an ophthalmic disease, wherein said ophthalmic disease is selected from the group consisting of pterygia, hyperemia related to an actively inflamed pterygia, recurrent pterygia following excisional surgery, prophylactic therapy to prevent recurrent pterygia post-excision, progressive pterygia approaching the visual axis, chronic low grade hyperemia associated with pterygia, corneal neovascularization, neovascular glaucoma, iris neovascularization, chronic allergic conjunctivitis, ocular rosacea, blepharoconjunctivitis, recurrent episcleritis, keratoconjunctivitis sicca, ocular graft vs host disease, diabetic retinopathy, diabetic macular edema, proliferative diabetic retinopathy, exudative or neovascular age-related macular degeneration, high-risk eyes (i.e. fellow eyes have neovascular age-related macular degeneratuon) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, idiopathic etiologies, presumed ocular histoplasmosis syndrome, and retinopathy of prematurity.

The following defined terms are used throughout this specification:

"Ac" refers to acetyl.
"Me" refers to methyl.
"PDGF" refers to platelet derived growth factor.
"DCM" refers to dichloromethane
"DMF" refers to methylformamide
"BOP" refers to benzotriazol-1-yloxytris(dimethylamino)phosphoniumhexafluorophnosphate
"DCE" refers to 1,2 dichloroethane
"DMAP" refers to 4-dimethylaminopyridine
"EDCI" refers to N-(3-Dimethylaminopropyl)-N'-ethylcarbodiimide
"HMPA" refers to hexamethylphosphoramide
"TBDMSCl" refers to tertiary\butyldimethylsilylchloride
"DIPEA" refers to N,N-diisopropylethylamide
"BOC" refers to ditertiarybutyldicarbonate
"Ph" refers to a phenyl radical or a substituted phenyl radical wherein one or more, but not all, of the hydrogen and/or the carbon atoms may be replaced by a halogen, nitrogen, oxygen, sulfur or phosphorus atom or a radical including a halo, nitrogen, oxygen, sulfur or phosphorus atom, e.g. fluoro, chloro, cyano, nitro, dialkylamino, hydroxyl, phosphate, thiol, etc.
"PTK" refers to protein tyrosine kinase.
"RT" refers to room temperature.
"VEGF" refers to vascular endothelial growth factor.
"VEGFR" refers to vascular endothelial growth factor receptor "Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halo, nitrogen, oxygen, sulfur or phosphorus atom, e.g. fluoro, chloro, cyano, nitro, dialkylamino, hydroxyl, phosphate, thiol, etc.

"Furanyl" refers to a furanyl radical or a substituted furanyl radical wherein one or more, but not all, of the hydrogen and/or the carbon atoms are replaced by a lower alkyl, halogen, nitrogen, oxygen, sulfur or phosphorus atom or a radical including a halo, nitrogen, oxygen, sulfur or phosphorus atom, e.g. fluoro, chloro, cyano, nitro, dialkylamino, hydroxyl, phosphate, thiol, etc.

"Oxazoyl" refers to an oxzazoyl radical or a substituted oxzazoyl radical wherein one or more, but not all, of the hydrogen and/or the carbon atoms are replaced by a lower alkyl, halogen, nitrogen, oxygen, sulfur or phosphorus atom or a radical including a halo, nitrogen, oxygen, sulfur or phosphorus atom, e.g. fluoro, chloro, cyano, nitro, dialkylamino, hydroxyl, phosphate, thiol, etc.

"Diazinyl" refers to a diazinyl radical or a substituted diazinyl radical wherein one or more, but not all, of the hydrogen and/or the carbon atoms are replaced by a lower alkyl, halogen, nitrogen, oxygen, sulfur or phosphorus atom or a radical including a halo, nitrogen, oxygen, sulfur or phosphorus atom, e.g. fluoro, chloro, cyano, nitro, dialkylamino, hydroxyl, phosphate, thiol, etc.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others. All such acid salts and base salts are intended to be pharmaceutically acceptable salts within the scope of the invention and all acid and base salts are considered equivalent to the free forms of the corresponding compounds for purposes of the invention.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. 25 Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkoxy" refers to O-alkyl.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Carbocyclic aryl" refers to an aryl group wherein the ring atoms are carbon

Heteroaryl" or "heterocyclic aryl" refers to an aryl group having from 1 to 3 heteroatoms as ring atoms, the remainder of the ring atoms being carbon. Heteroatoms include oxygen, sulfur, and nitrogen. Thus, heteroaryl groups include furanyl, thienyl, pyridyl, pyrrolyl, N-lower alkyl pyrrolo, pyrimidyl, pyrazinyl, imidazolyl and the like.

"Heterocyclic" refers to cyclic group having at least one enchained heteroatom and includes aromatic and non-aromatic cyclic groups.

The preferred compounds and their structures are set out in Tables 1 through 5, below.

| Example | Structure | Compound Name |
|---|---|---|
| 1 | 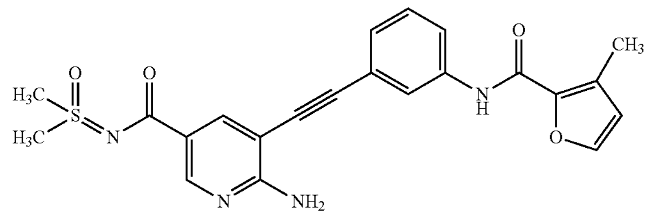 [SMILES: Cc1ccoc1C(=O)Nc1cccc(C#Cc2cc(C(=O)N=S(C)(C)=O)cnc2N)c1] | 6-amino-N-[dimethyl(oxido)-$\lambda^4$-sulfanylidene]-5-({3-[(3-methyl-2-furoyl)amino]phenyl}ethynyl)nicotinamide |
| 2 | 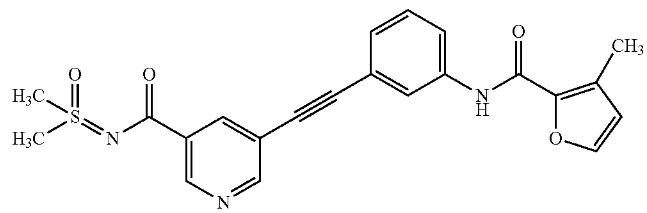 [SMILES: Cc1ccoc1C(=O)Nc1cccc(C#Cc2cncc(C(=O)N=S(C)(C)=O)c2)c1] | N-[dimethyl(oxido)-$\lambda^4$-sulfanylidene]-5-({3-[(3-methyl-2-furoyl)amino]phenyl}ethynyl)nicotinamide |
| 3 | 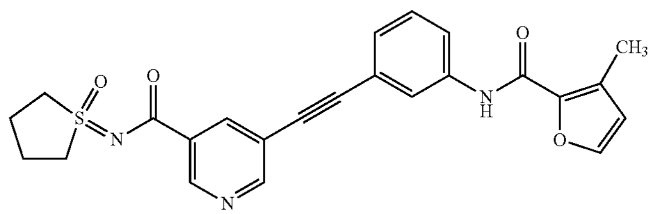 [SMILES: Cc1ccoc1C(=O)Nc1cccc(C#Cc2cncc(C(=O)N=S3(=O)CCCC3)c2)c1] | 5-({3-[(3-methyl-2-furoyl)amino]phenyl}ethynyl)-N-(1-oxidotetrahydro-1H-1$\lambda^4$-thien-1-ylidene)nicotinamide |
| 4 | 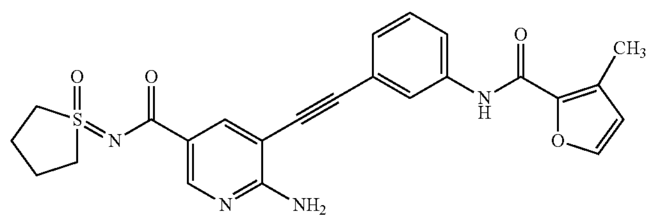 [SMILES: Cc1ccoc1C(=O)Nc1cccc(C#Cc2cc(C(=O)N=S3(=O)CCCC3)cnc2N)c1] | 6-amino-5-({3-[(3-methyl-2-furoyl)amino]phenyl}ethynyl)-N-(1-oxidotetrahydro-1H-1$\lambda^4$-thien-1-ylidene)nicotinamide |
| 5 | 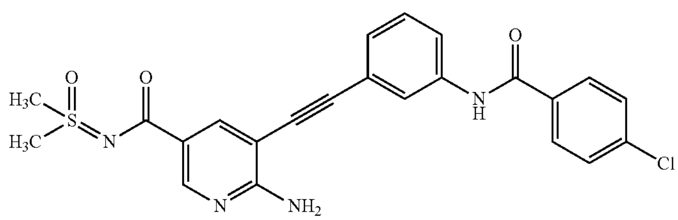 [SMILES: CS(C)(=O)=NC(=O)c1cnc(N)c(C#Cc2cccc(NC(=O)c3ccc(Cl)cc3)c2)c1] | 6-amino-5-({3-[(4-chlorobenzoyl)amino]phenyl}ethynyl)-N-[dimethyl(oxido)-$\lambda^4$-sulfanylidene]nicotinamide |
| 6 | 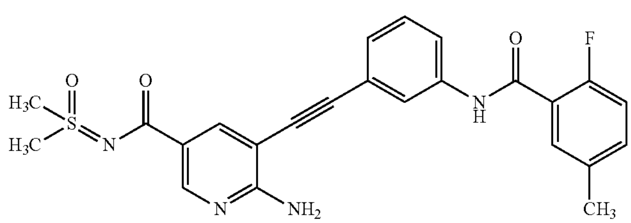 [SMILES: Cc1ccc(F)c(C(=O)Nc2cccc(C#Cc3cc(C(=O)N=S(C)(C)=O)cnc3N)c2)c1] | 6-amino-N-[dimethyl(oxido)-$\lambda^4$-sulfanylidene]-5-({3-[(2-fluoro-5-methylbenzoyl)amino]phenyl}ethynyl)nicotinamide |
| 7 | 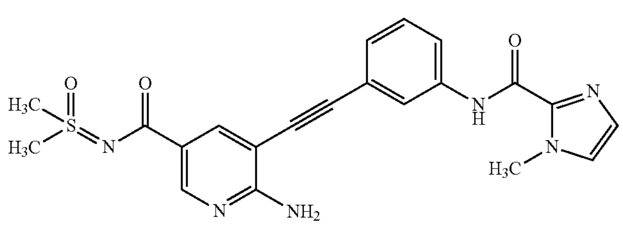 [SMILES: Cn1ccnc1C(=O)Nc1cccc(C#Cc2cc(C(=O)N=S(C)(C)=O)cnc2N)c1] | 6-amino-N-[dimethyl(oxido)-$\lambda^4$-sulfanylidene]-5-[(3-{[(1-methyl-1H-imidazol-2-yl)carbonyl]amino}phenyl)ethynyl]nicotinamide |

-continued

| Example | Structure | Compound Name |
|---|---|---|
| 8 | 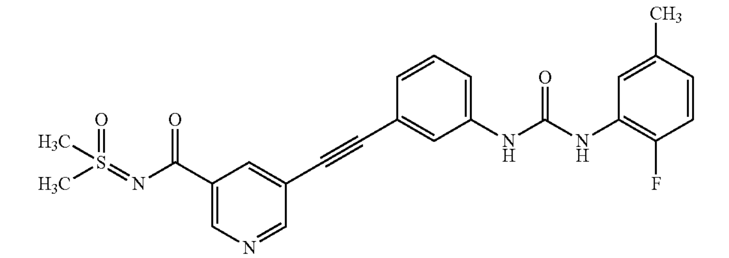 [SMILES: Cc1ccc(F)c(NC(=O)Nc2cccc(C#Cc3cncc(C(=O)N=S(C)(C)=O)c3)c2)c1] | N-[dimethyl(oxido)-λ⁴-sulfanylidene]-5-{[3-({[(2-fluoro-5-methylphenyl)amino]carbonyl}amino)phenyl]ethynyl}nicotinamide |
| 9 | 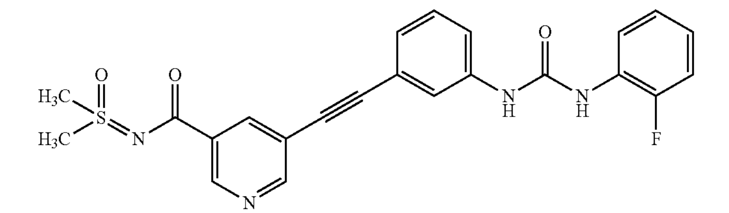 [SMILES: CS(C)(=O)=NC(=O)c1cncc(C#Cc2cccc(NC(=O)Nc3ccccc3F)c2)c1] | N-[dimethyl(oxido)-λ⁴-sulfanylidene]-5-{[3-({[(2-fluorophenyl)amino]carbonyl}amino)phenyl]ethynyl}nicotinamide |
| 10 | 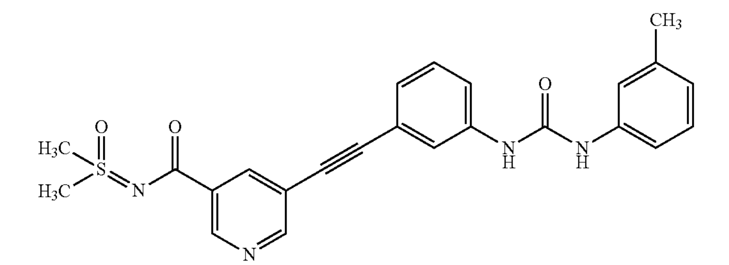 [SMILES: Cc1cccc(NC(=O)Nc2cccc(C#Cc3cncc(C(=O)N=S(C)(C)=O)c3)c2)c1] | N-[dimethyl(oxido)-λ⁴-sulfanylidene]-5-{[3-({[(3-methylphenyl)amino]carbonyl}amino)phenyl]ethynyl}nicotinamide |
| 11 | 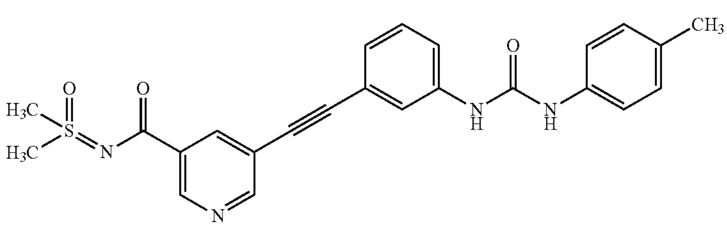 | N-[dimethyl(oxido)-λ⁴-sulfanylidene]-5-{[3-({[(4-methylphenyl)amino]carbonyl}amino)phenyl]ethynyl}nicotinamide |
| 12 | 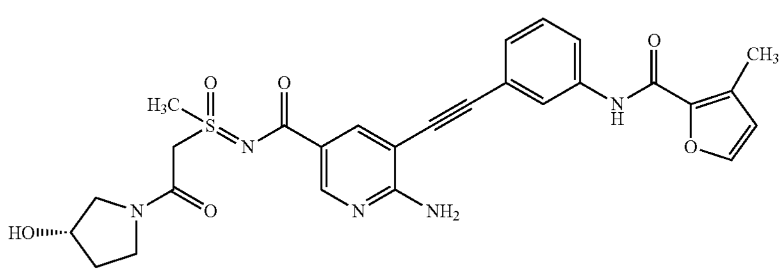 [SMILES: Cc1ccoc1C(=O)Nc1cccc(C#Cc2cc(C(=O)N=S(C)(=O)CC(=O)N3CC[C@H](O)C3)cnc2N)c1] | 6-amino-N-{[2-(3-hydroxypyrrolidin-1-yl)-2-oxoethyl](methyl)oxido-λ⁴-sulfanylidene}-5-({3-[(3-methyl-2-furoyl)amino]phenyl}ethynyl)nicotinamide |
| 13 | 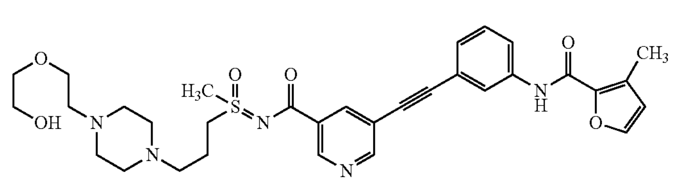 [SMILES: Cc1ccoc1C(=O)Nc1cccc(C#Cc2cncc(C(=O)N=S(C)(=O)CCCN3CCN(CCOCCO)CC3)c2)c1] | N-[(3-{4-[2-(2-hydroxyethoxy)ethyl]piperazin-1-yl}propyl)(methyl)oxido-λ⁴-sulfanylidene]-5-({3-[(3-methyl-2-furoyl)amino]phenyl}ethynyl)nicotinamide |

| Example | Structure | Compound Name |
|---|---|---|
| 14 | 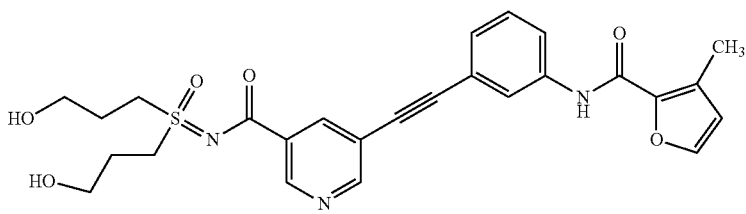 [SMILES: Cc1ccoc1C(=O)Nc1cccc(C#Cc2cncc(C(=O)N=S(=O)(CCCO)CCCO)c2)c1] | N-[bis(3-hydroxypropyl)(oxido)-$\lambda^4$-sulfanylidene]-5-({3-[(3-methyl-2-furoyl)amino]phenyl}ethynyl)nicotinamide |
| 15 | 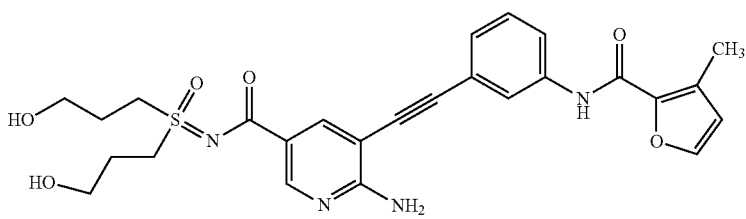 [SMILES: Cc1ccoc1C(=O)Nc1cccc(C#Cc2cc(C(=O)N=S(=O)(CCCO)CCCO)cnc2N)c1] | 6-amino-N-[bis(3-hydroxypropyl)(oxido)-$\lambda^4$-sulfanylidene]-5-({3-[(3-methyl-2-furoyl)amino]phenyl}ethynyl)nicotinamide |
| 16 | 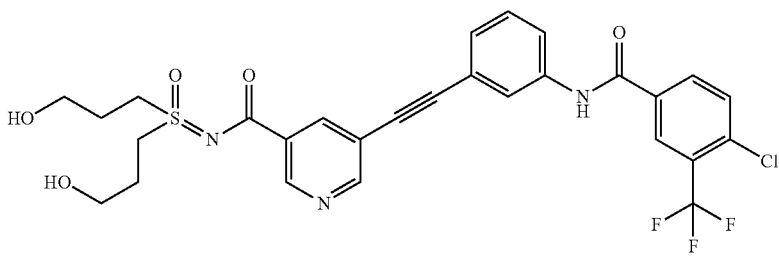 [SMILES: O=C(N=S(=O)(CCCO)CCCO)c1cncc(C#Cc2cccc(NC(=O)c3ccc(Cl)c(C(F)(F)F)c3)c2)c1] | N-[bis(3-hydroxypropyl)(oxido)-$\lambda^4$-sulfanylidene]-5-[(3-{[4-chloro-3-trifluoromethyl)benzoyl]amino}phenyl)ethynyl]nicotinamide |
| 17 | 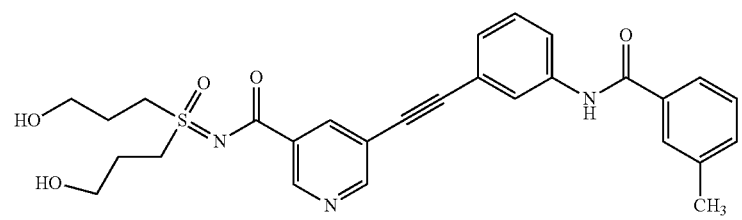 [SMILES: Cc1cccc(C(=O)Nc2cccc(C#Cc3cncc(C(=O)N=S(=O)(CCCO)CCCO)c3)c2)c1] | N-[bis(3-hydroxypropyl)(oxido)-$\lambda^4$-sulfanylidene]-5-({3-[(3-methylbenzoyl)amino]phenyl}ethynyl)nicotinamide |
| 18 | 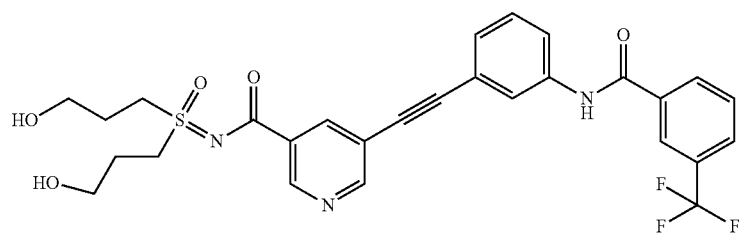 [SMILES: O=C(N=S(=O)(CCCO)CCCO)c1cncc(C#Cc2cccc(NC(=O)c3cccc(C(F)(F)F)c3)c2)c1] | N-[bis(3-hydroxypropyl)(oxido)-$\lambda^4$-sulfanylidene]-5-[(3-{[3-(trifluoromethyl)benzoyl]amino}phenyl)ethynyl]nicotinamide |
| 19 | 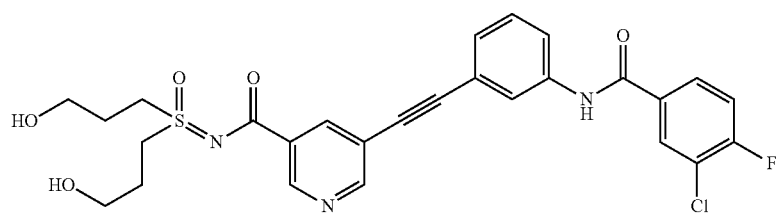 [SMILES: O=C(N=S(=O)(CCCO)CCCO)c1cncc(C#Cc2cccc(NC(=O)c3ccc(F)c(Cl)c3)c2)c1] | N-[bis(3-hydroxypropyl)(oxido)-$\lambda^4$-sulfanylidene]-5-({3-[(3-chloro-4-fluorobenzoyl)amino]phenyl}ethynyl)nicotinamide |

-continued

| Example | Structure | Compound Name |
|---|---|---|
| 20 | 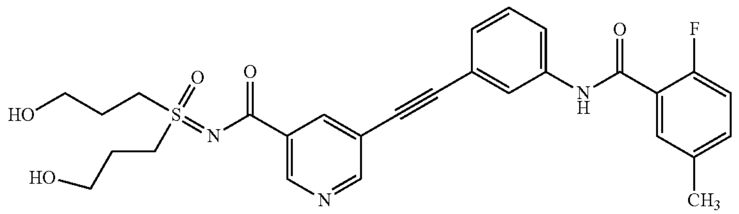 [SMILES: Cc1ccc(F)c(C(=O)Nc2cccc(C#Cc3cncc(C(=O)N=S(=O)(CCCO)CCCO)c3)c2)c1] | N-[bis(3-hydroxypropyl)(oxido)-λ⁴-sulfanylidene]-5-({3-[(2-fluoro-5-methylbenzoyl)amino]phenyl}ethynyl)nicotinamide |
| 21 | 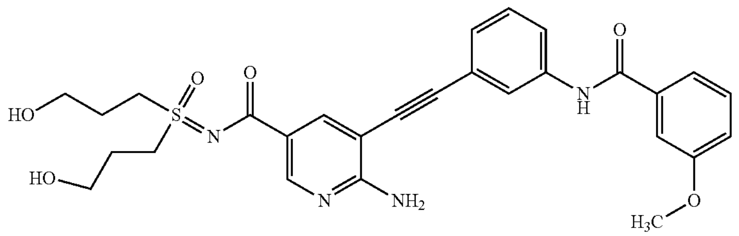 [SMILES: COc1cccc(C(=O)Nc2cccc(C#Cc3cc(C(=O)N=S(=O)(CCCO)CCCO)cnc3N)c2)c1] | 6-amino-N-[bis(3-hydroxypropyl)(oxido)-λ⁴-sulfanylidene]-5-({3-[(3-methoxybenzoyl)amino]phenyl}ethynyl)nicotinamide |
| 22 | 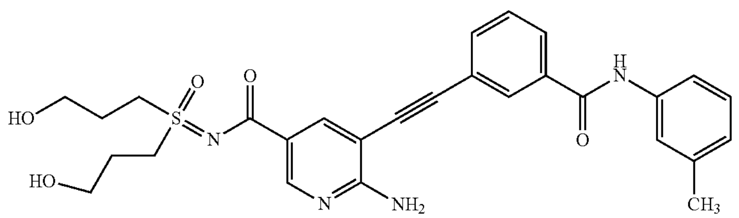 [SMILES: Cc1cccc(NC(=O)c2cccc(C#Cc3cc(C(=O)N=S(=O)(CCCO)CCCO)cnc3N)c2)c1] | 6-amino-N-[bis(3-hydroxypropyl)(oxido)-λ⁴-sulfanylidene]-5-[(3-{[(3-methylphenyl)amino]carbonyl}phenyl)ethynyl]nicotinamide |
| 23 | 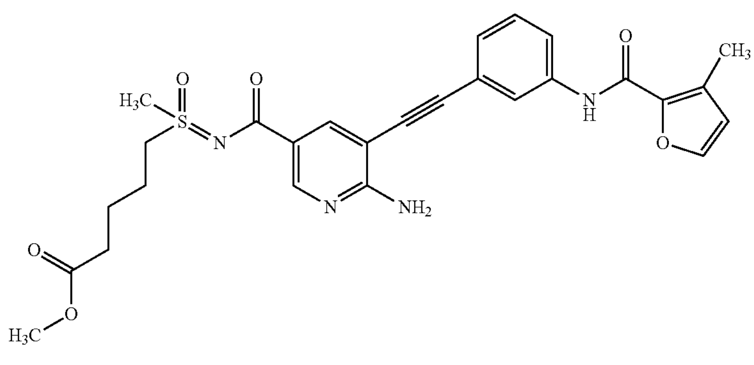 [SMILES: COC(=O)CCCCS(C)(=O)=NC(=O)c1cnc(N)c(C#Cc2cccc(NC(=O)c3occc3C)c2)c1] | methyl 5-(N-{[6-amino-5-({3-[(3-methyl-2-furoyl)amino]phenyl}ethynyl)pyridin-3-yl]carbonyl}-S-methylsulfonimidoyl)pentanoate |
| 24 | 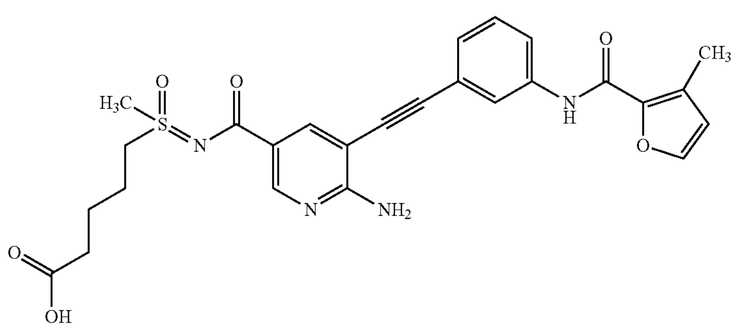 [SMILES: Cc1ccoc1C(=O)Nc1cccc(C#Cc2cc(C(=O)N=S(C)(=O)CCCCC(=O)O)cnc2N)c1] | 5-(N-{[6-amino-5-({3-[(3-methyl-2-furoyl)amino]phenyl}ethynyl)pyridin-3-yl]carbonyl}-S-methylsulfonimidoyl)pentanoic acid |

-continued

| Example | Structure | Compound Name |
|---|---|---|
| 25 | 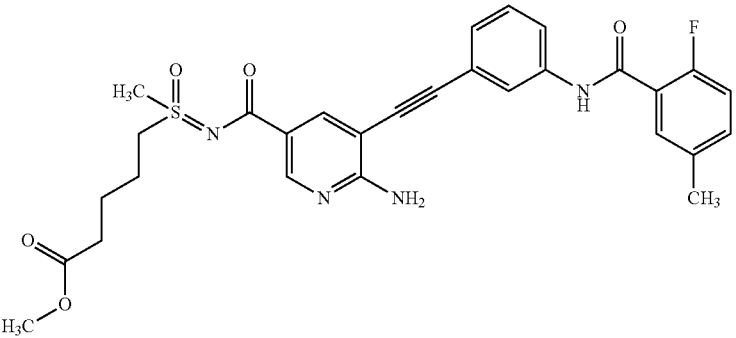 | methyl 5-(N-{[6-amino-5-({3-[(2-fluoro-5-methylbenzoyl)amino]phenyl}ethynyl)pyridin-3-yl]carbonyl}-S-methylsulfonimidoyl)pentanoate |
| 26 | 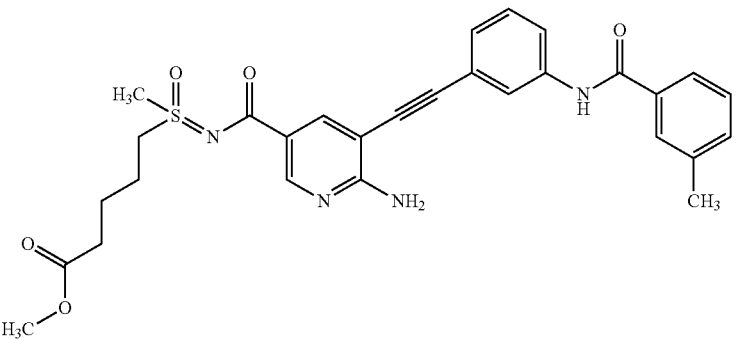 [SMILES: COC(=O)CCCCS(C)(=O)=NC(=O)c1cnc(N)c(C#Cc2cccc(NC(=O)c3cccc(C)c3)c2)c1] | methyl 5-(N-{[6-amino-5-({3-[(3-methylbenzoyl)amino]phenyl}ethynyl)pyridin-3-yl]carbonyl}-S-methylsulfonimidoyl)pentanoate |
| 27 | 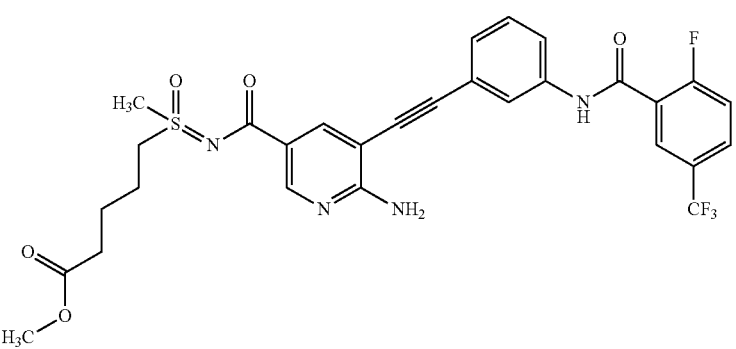 [SMILES: COC(=O)CCCCS(C)(=O)=NC(=O)c1cnc(N)c(C#Cc2cccc(NC(=O)c3cc(C(F)(F)F)ccc3F)c2)c1] | methyl 5-[N-({6-amino-5-[(3-{[2-fluoro-5-(trifluoromethyl)benzoyl]amino}phenyl)ethynyl]pyridin-3-yl}carbonyl)-S-methylsulfonimidoyl]pentanoate |
| 28 | 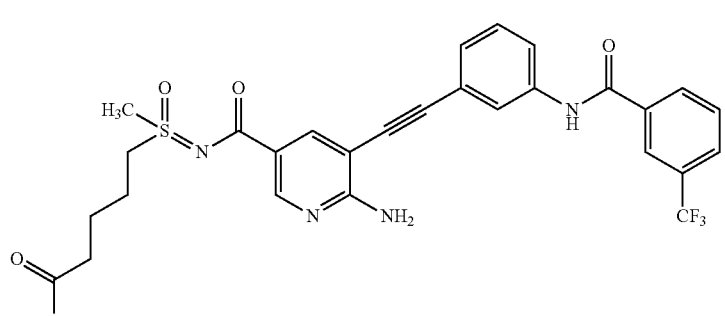 | methyl 5-[N-({6-amino-5-[(3-{[3-(trifluoromethyl)benzoyl]amino}phenyl)ethynyl]pyridin-3-yl}carbonyl)-S-methylsulfonimidoyl]pentanoate |

-continued

| Example | Structure | Compound Name |
|---|---|---|
| 29 | 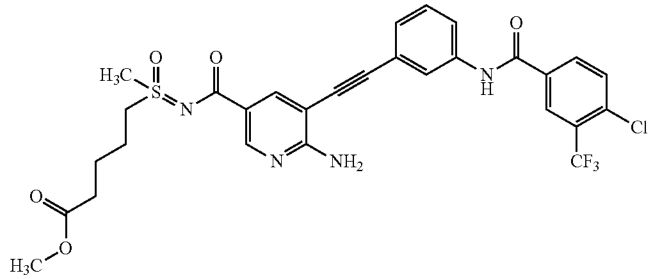 [SMILES: COC(=O)CCCCS(C)(=O)=NC(=O)c1cnc(N)c(C#Cc2cccc(NC(=O)c3ccc(Cl)c(C(F)(F)F)c3)c2)c1] | methyl 5-[N-({6-amino-5-[(3-{[4-chloro-3-(trifluoromethyl)benzoyl]amino}phenyl)ethynyl]pyridin-3-yl}carbonyl)-S-methylsulfonimidoyl]pentanoate |
| 30 | 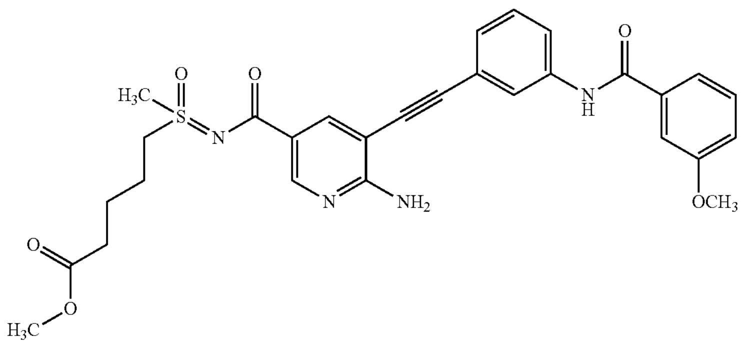 [SMILES: COC(=O)CCCCS(C)(=O)=NC(=O)c1cnc(N)c(C#Cc2cccc(NC(=O)c3cccc(OC)c3)c2)c1] | methyl 5-(N-{[6-amino 5-({3-[(3-methoxybenzoyl)amino]phenyl}ethynyl)pyridin-3-yl]carbonyl}-S-methylsulfonimidoyl)pentanoate |
| 31 | 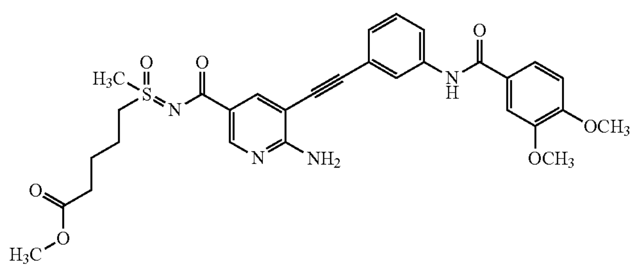 [SMILES: COC(=O)CCCCS(C)(=O)=NC(=O)c1cnc(N)c(C#Cc2cccc(NC(=O)c3ccc(OC)c(OC)c3)c2)c1] | methyl 5-(N-{[6-amino-5-({3-[(3,4-dimethoxybenzoyl)amino]phenyl}ethynyl)pyridin-3-yl]carbonyl}-S-methylsulfonimidoyl)pentanoate |
| 32 | 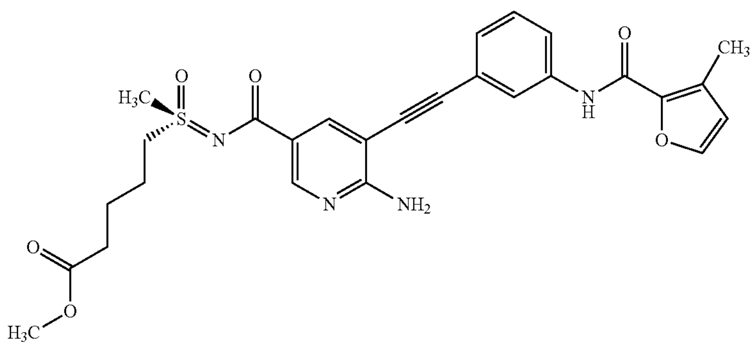 [SMILES: COC(=O)CCCC[S@](C)(=O)=NC(=O)c1cnc(N)c(C#Cc2cccc(NC(=O)c3occc3C)c2)c1] | (S)-methyl 5-(N-{[6-amino-5-({3-[(3-methyl-2-furoyl)amino]phenyl}ethynyl)pyridin-3-yl]carbonyl}-S-methylsulfonimidoyl)pentanoate |
| 33 | 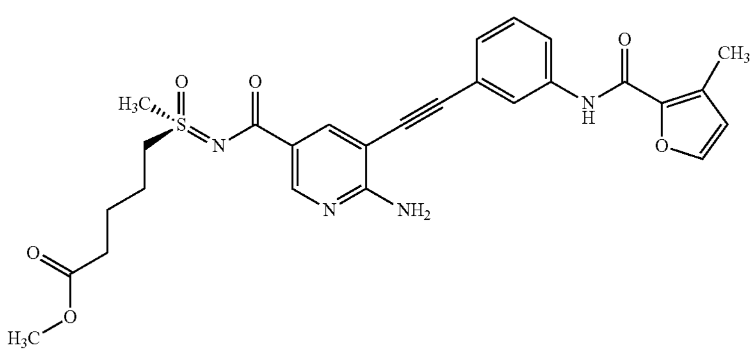 [SMILES: COC(=O)CCCC[S@@](C)(=O)=NC(=O)c1cnc(N)c(C#Cc2cccc(NC(=O)c3occc3C)c2)c1] | (R)-methyl 5-(N-{[6-amino-5-({3-[(3-methyl-2-furoyl)amino]phenyl}ethynyl)pyridin-3-yl]carbonyl}-S-methylsulfonimidoyl)pentanoate |

-continued

| Example | Structure | Compound Name |
|---|---|---|
| 34 | 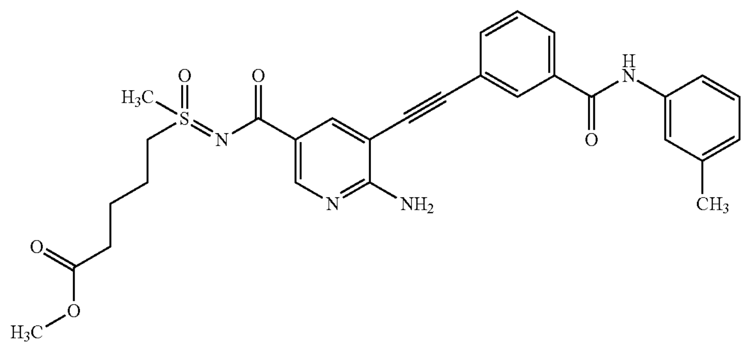 [SMILES: COC(=O)CCCCS(C)(=O)=NC(=O)c1cnc(N)c(C#Cc2cccc(C(=O)Nc3cccc(C)c3)c2)c1] | methyl 5-[N-({6-amino-5-[(3-{[(3-methylphenyl)amino]carbonyl}phenyl)ethynyl]pyridin-3-yl}carbonyl)-S-methylsulfonimidoyl]pentanoate |
| 35 | 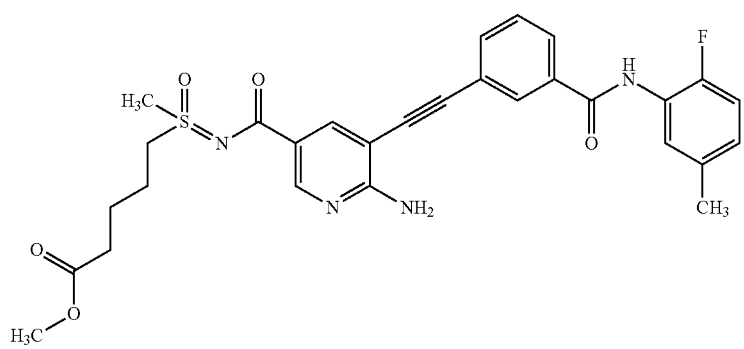 [SMILES: COC(=O)CCCCS(C)(=O)=NC(=O)c1cnc(N)c(C#Cc2cccc(C(=O)Nc3cc(C)ccc3F)c2)c1] | methyl 5-[N-({6-amino-5-[(3-{[(2-fluoro-5-methylphenyl)amino]carbonyl}phenyl)ethynyl]pyridin-3-yl}carbonyl)-S-methylsulfonimidoyl]pentanoate |
| 36 | 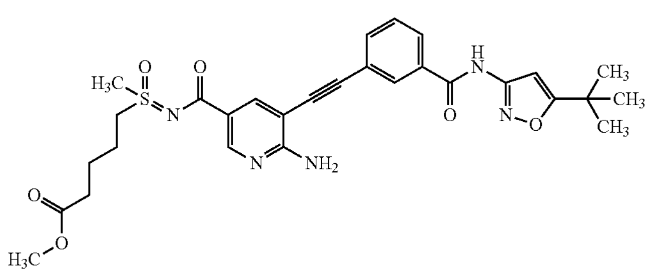 [SMILES: COC(=O)CCCCS(C)(=O)=NC(=O)c1cnc(N)c(C#Cc2cccc(C(=O)Nc3cc(C(C)(C)C)on3)c2)c1] | methyl 5-[N-({6-amino-5-[(3-{[(5-tert-butylisoxazol-3-yl)amino]carbonyl}phenyl)ethynyl]pyridin-3-yl}carbonyl)-S-methylsulfonimidoyl]pentanoate |
| 37 | 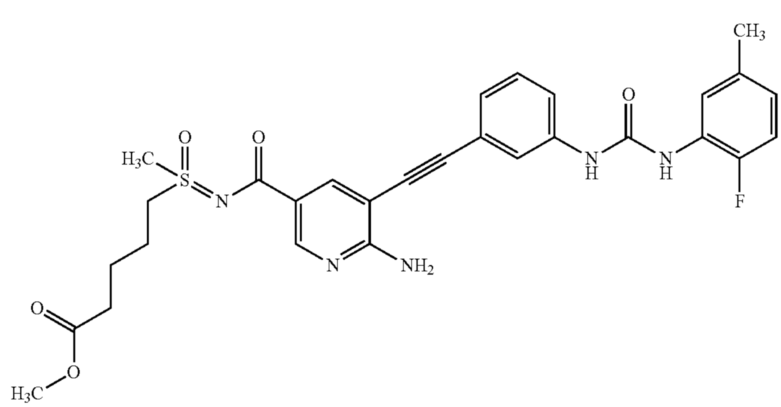 [SMILES: COC(=O)CCCCS(C)(=O)=NC(=O)c1cnc(N)c(C#Cc2cccc(NC(=O)Nc3cc(C)ccc3F)c2)c1] | methyl 5-{N-[(6-amino-5-{[3-({[(2-fluoro-5-methylphenyl)amino]carbonyl}amino)phenyl]ethynyl}pyridin-3-yl)carbonyl]-S-methylsulfonimidoyl}pentanoate |

-continued

| Example | Structure | Compound Name |
|---|---|---|
| 38 | 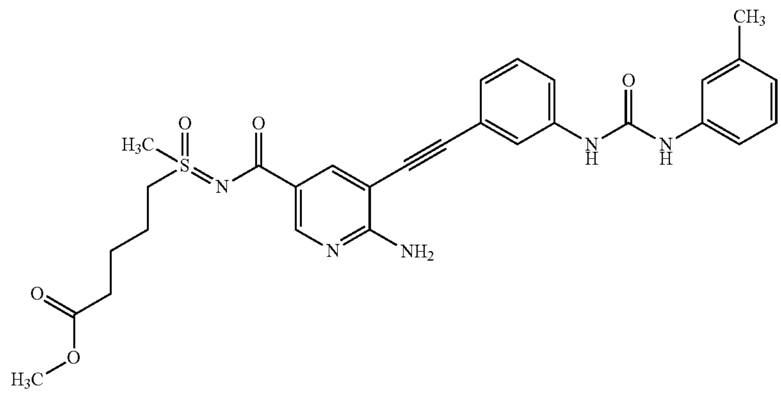 [SMILES: COC(=O)CCCCS(C)(=O)=NC(=O)c1cnc(N)c(C#Cc2cccc(NC(=O)Nc3cccc(C)c3)c2)c1] | methyl 5-{N-[(6-amino-5-{[3-({[(3-methylphenyl)amino]carbonyl}amino)phenyl]ethynyl}pyridin-3-yl)carbonyl]-S-methylsulfonimidoyl}pentanoate |
| 39 | 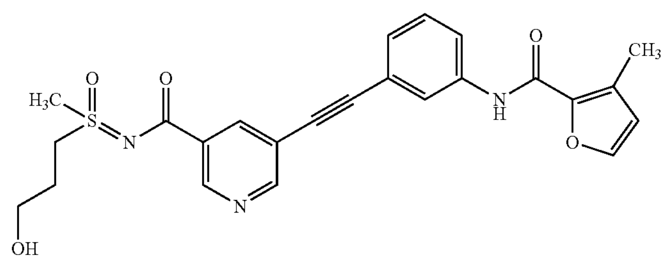 [SMILES: Cc1ccoc1C(=O)Nc1cccc(C#Cc2cncc(C(=O)N=S(C)(=O)CCCO)c2)c1] | N-[(3-hydroxypropyl)(methyl)oxido-$\lambda^4$-sulfanylidene]-5-({3-[(3-methyl-2-furoyl)amino]phenyl}ethynyl)nicotinamide |
| 40 | 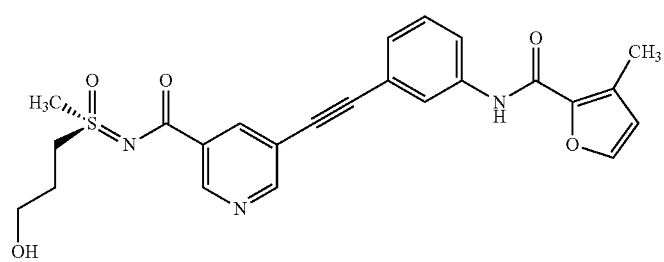 [SMILES: Cc1ccoc1C(=O)Nc1cccc(C#Cc2cncc(C(=O)N=[S@](C)(=O)CCCO)c2)c1] | (R)-N-[(3-hydroxypropyl)(methyl)oxido-$\lambda^4$-sulfanylidene]-5-({3-[(3-methyl-2-furoyl)amino]phenyl}ethynyl)nicotinamide |
| 41 | 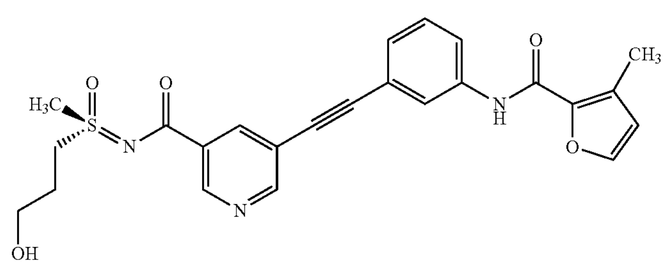 [SMILES: Cc1ccoc1C(=O)Nc1cccc(C#Cc2cncc(C(=O)N=[S@@](C)(=O)CCCO)c2)c1] | (S)-N-[(3-hydroxypropyl)(methyl)oxido-$\lambda^4$-sulfanylidene]-5-({3-[(3-methyl-2-furoyl)amino]phenyl}ethynyl)nicotinamide |
| 42 | 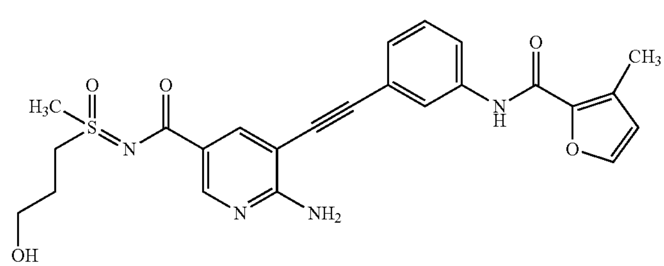 [SMILES: Cc1ccoc1C(=O)Nc1cccc(C#Cc2cc(C(=O)N=S(C)(=O)CCCO)cnc2N)c1] | 6-amino-N-[(3-hydroxypropyl)(methyl)oxido-$\lambda^4$-sulfanylidene]-5-({3-[(3-methyl-2-furoyl)amino]phenyl}ethynyl)nicotinamide |

Routes to said compounds are illustrated by but not limited to the schemes provided below:
Scheme 1
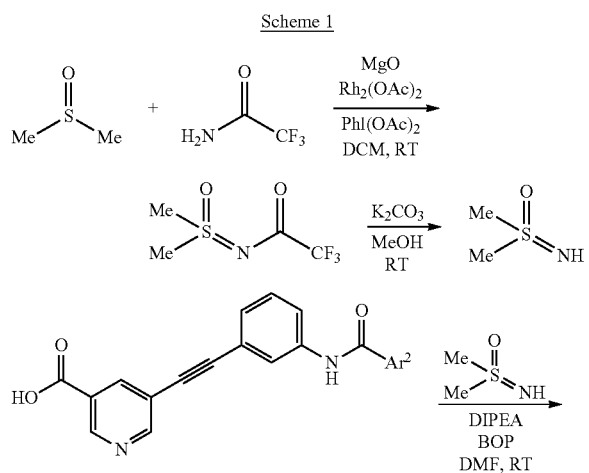
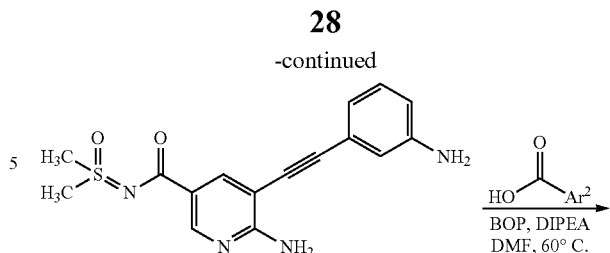
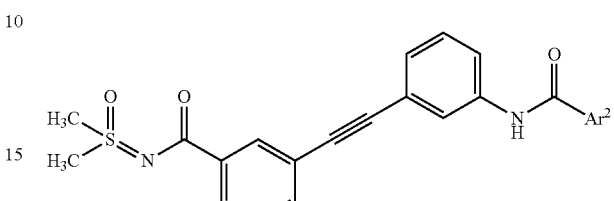
Scheme 3
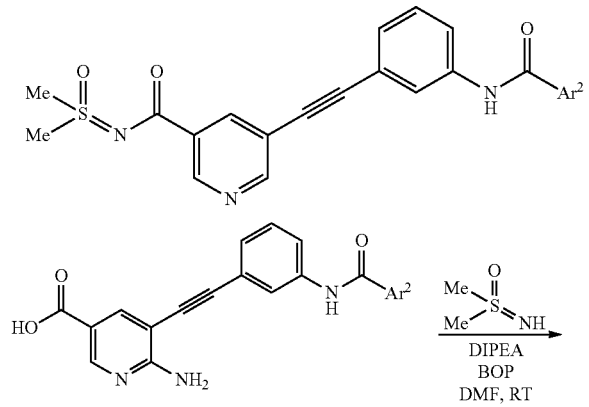
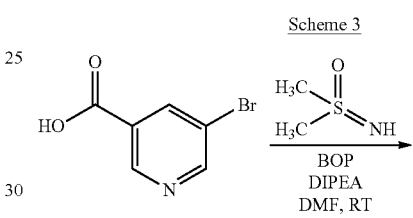
Scheme 2
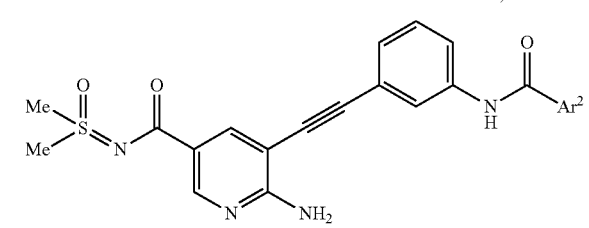
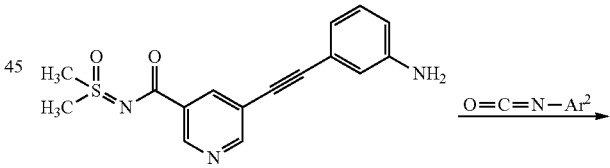
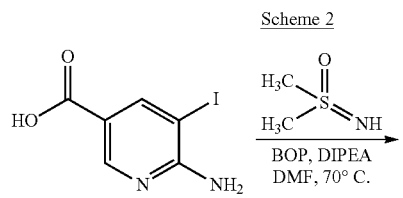
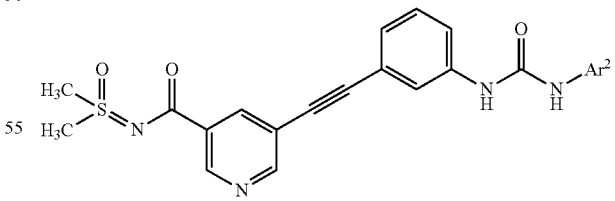
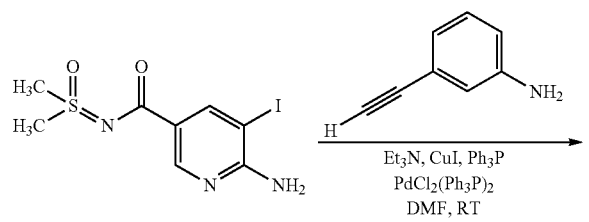
Scheme 4
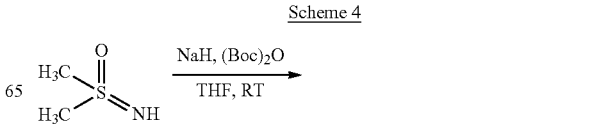

29
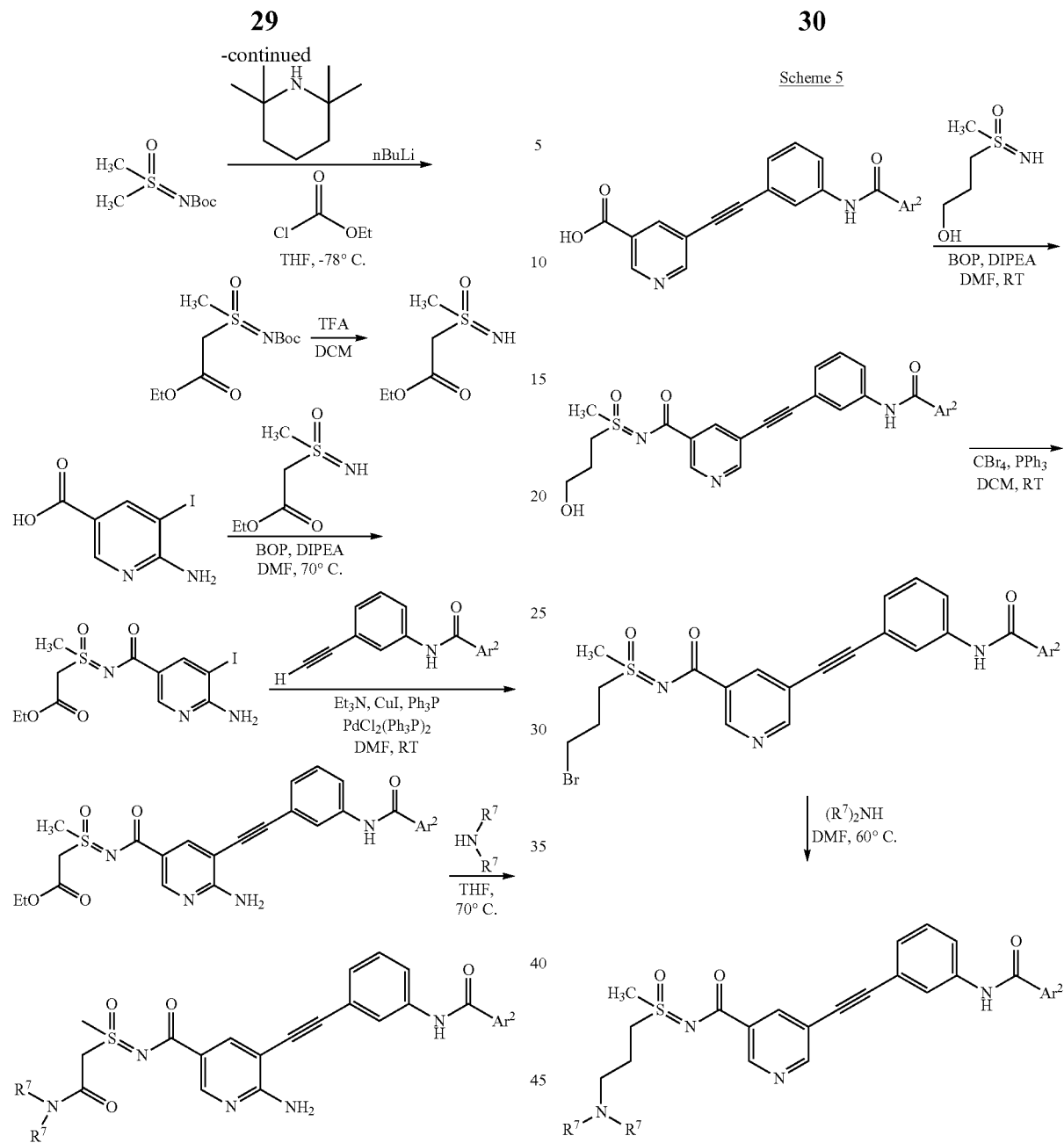
Scheme 5
30
Scheme 6
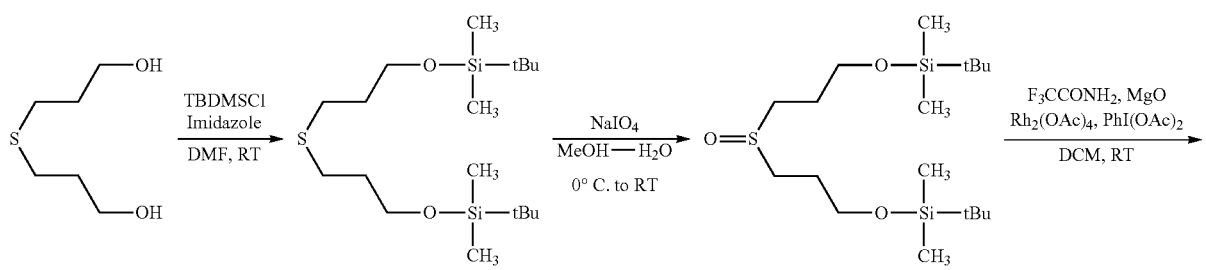

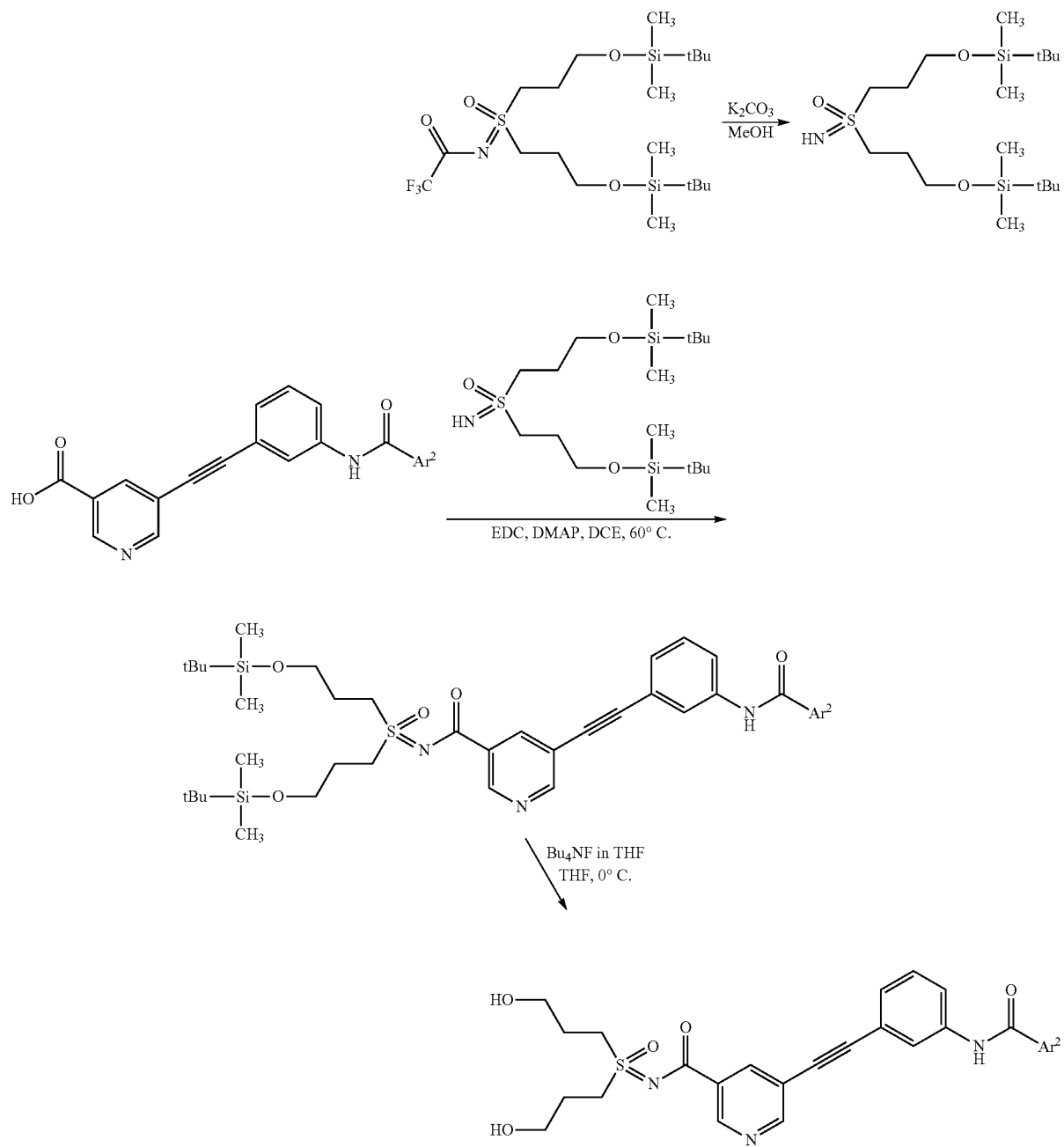
Scheme 7:
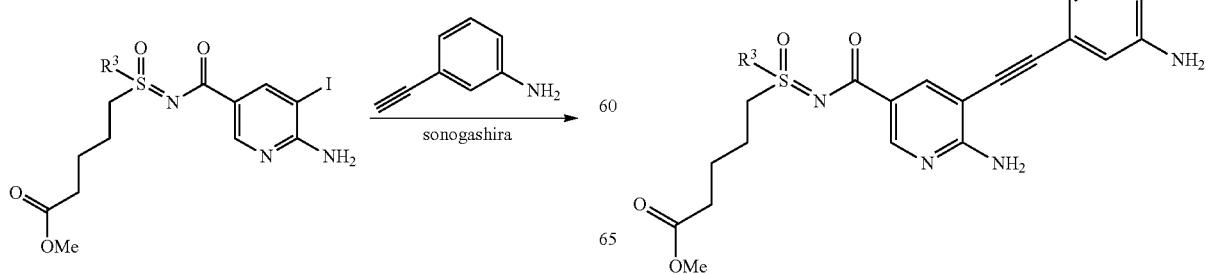

33
-continued
34
-continued
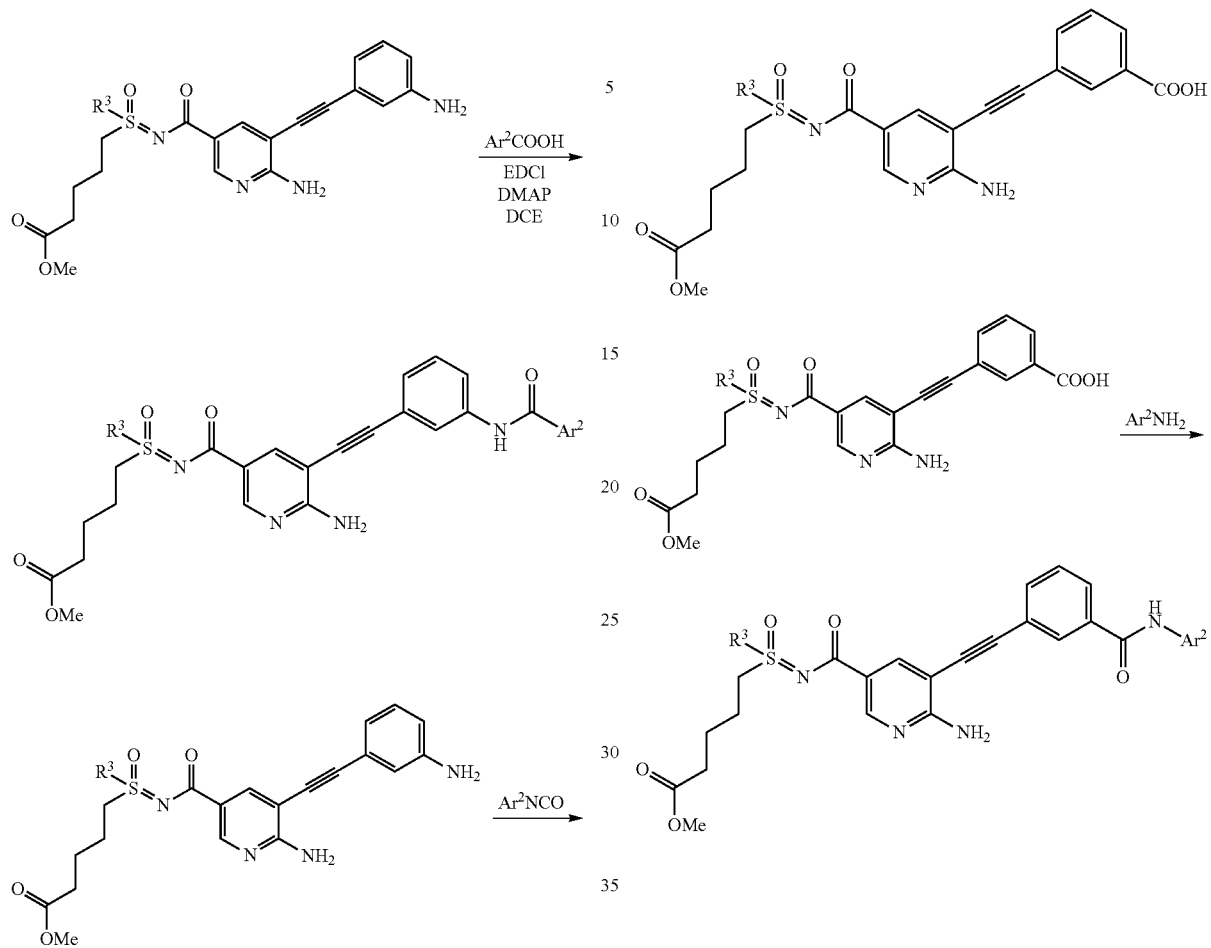
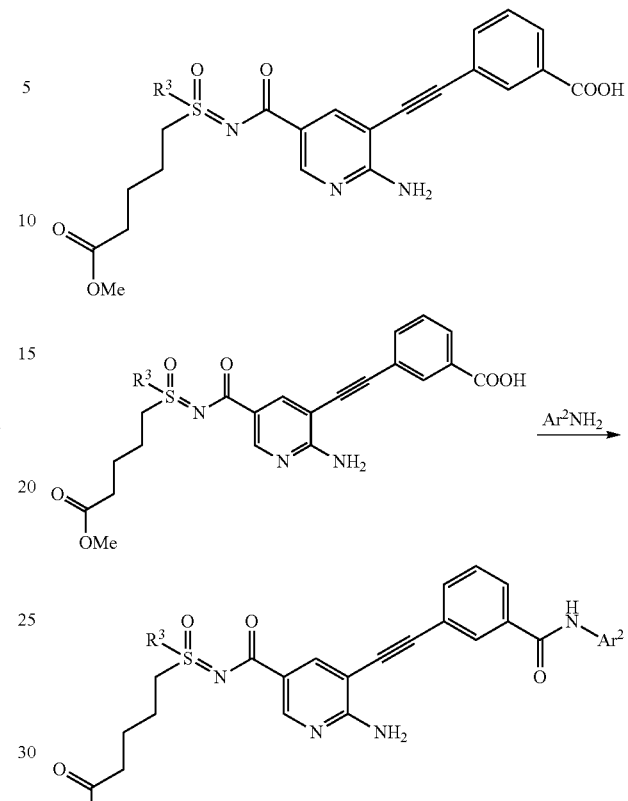
Scheme 8:
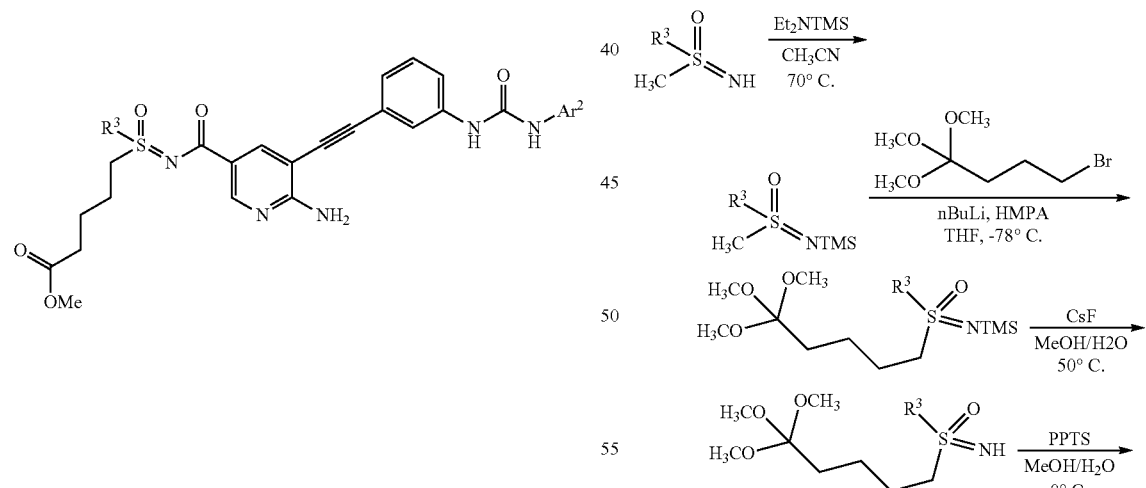
Scheme 9:
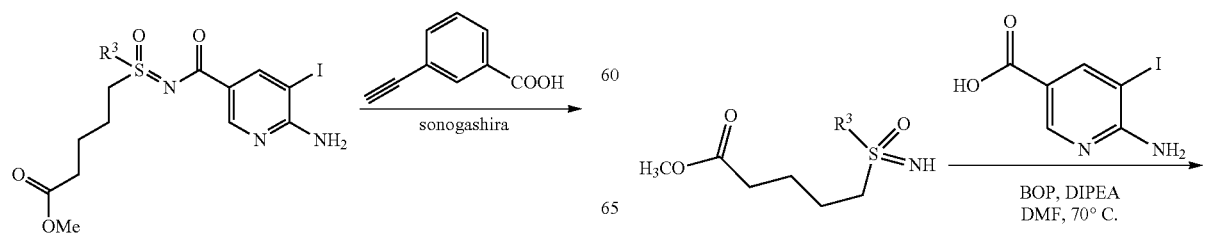

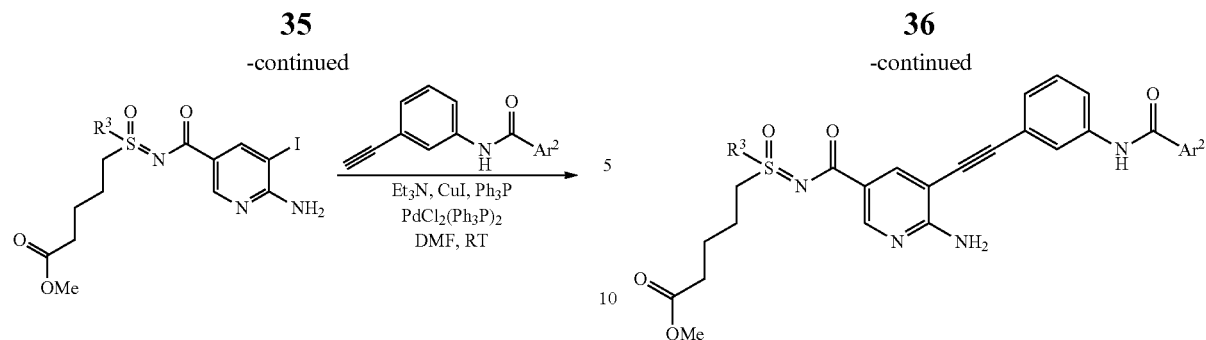
Scheme 10:
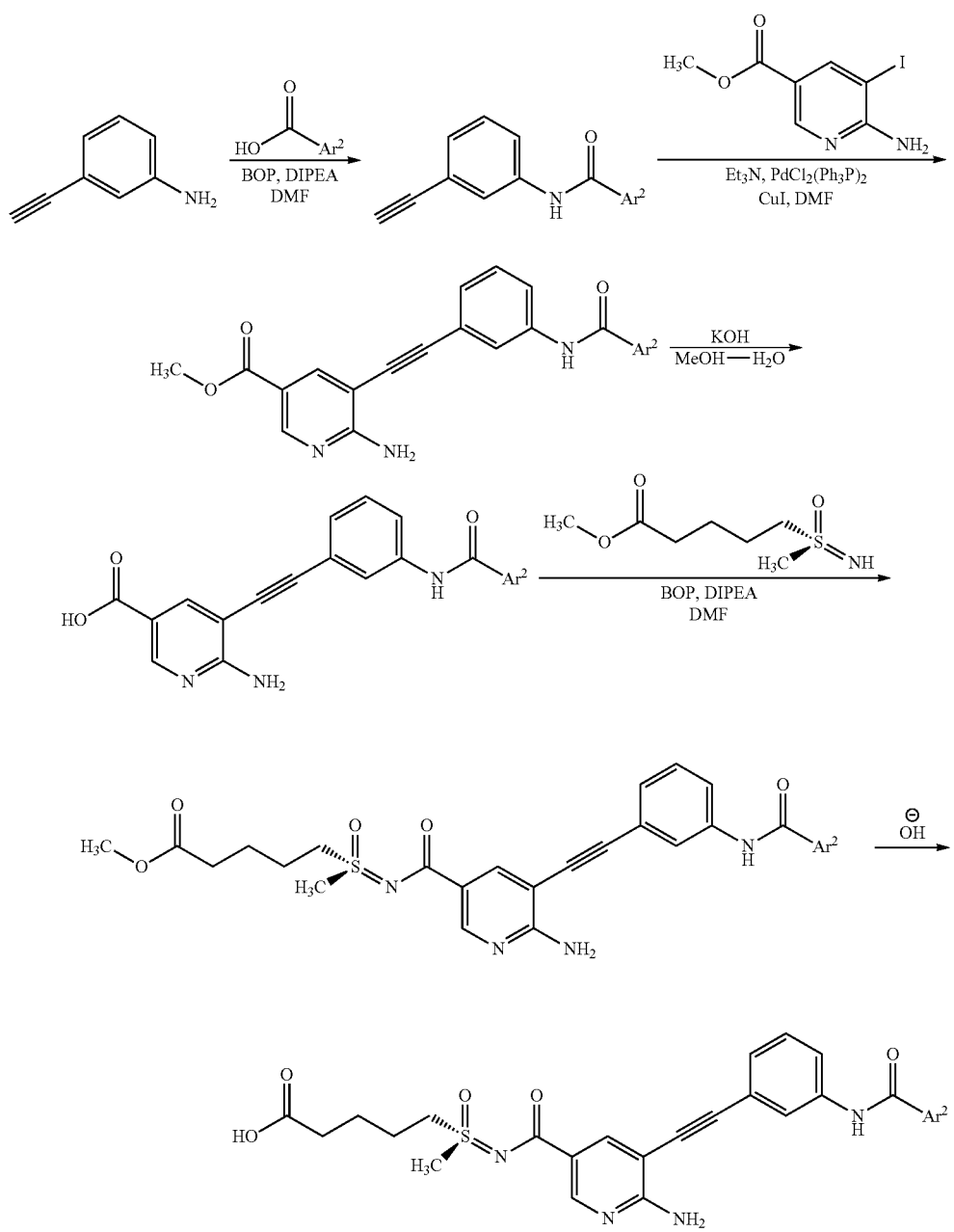

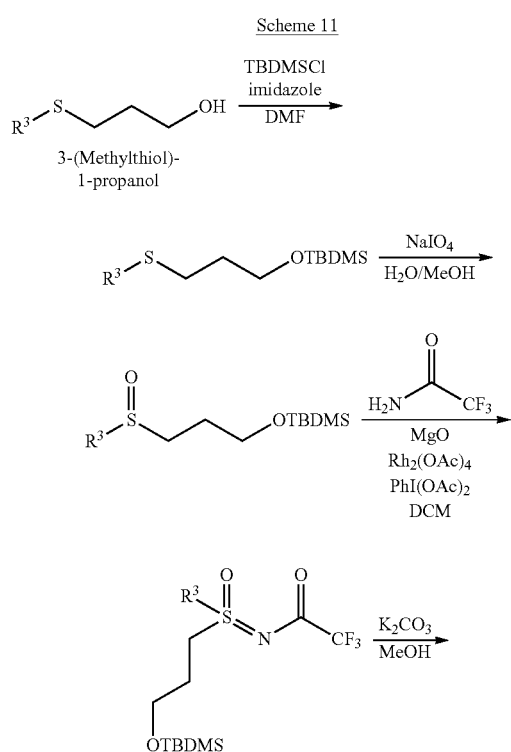
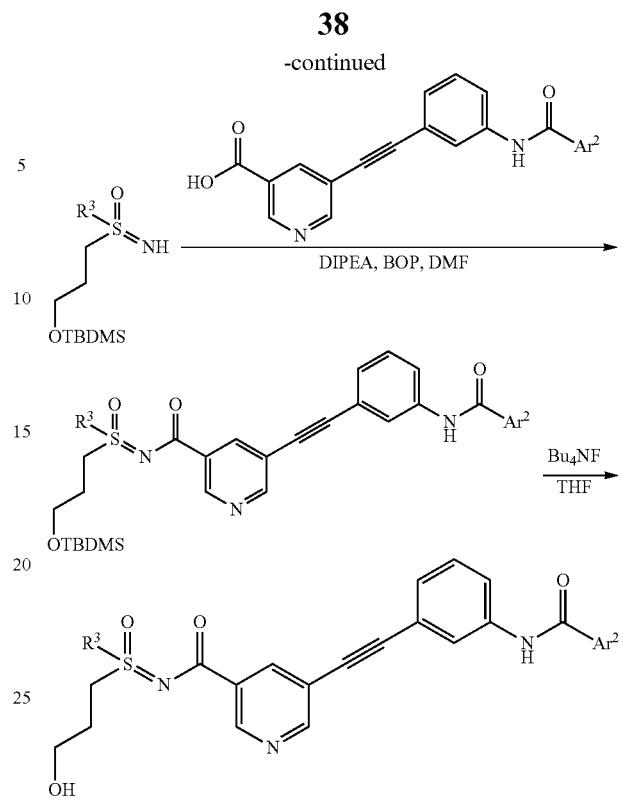

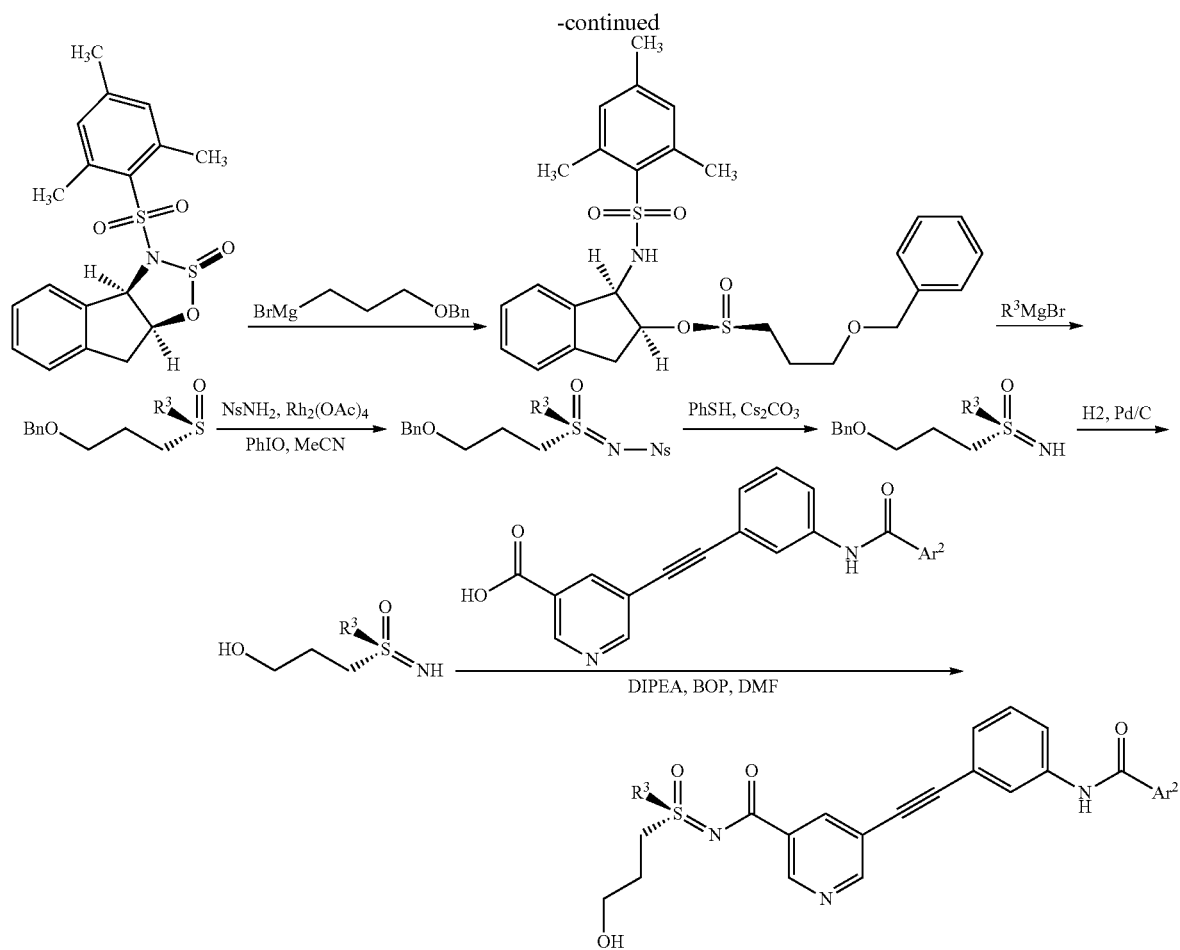
Scheme 13
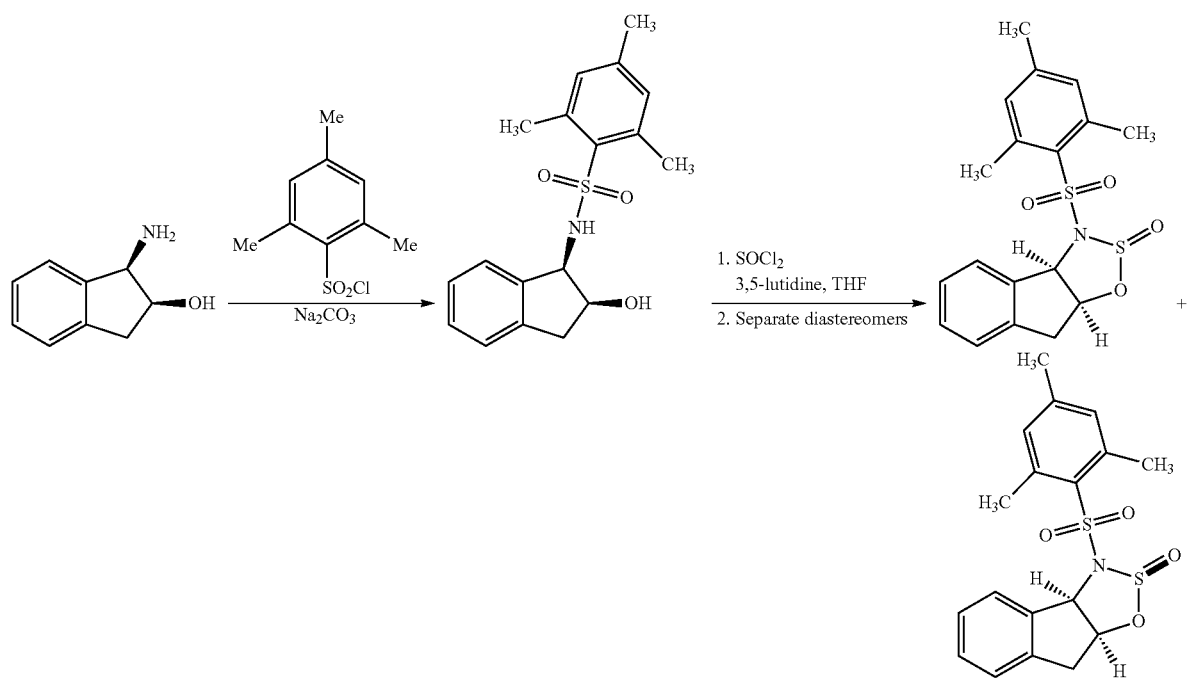

-continued

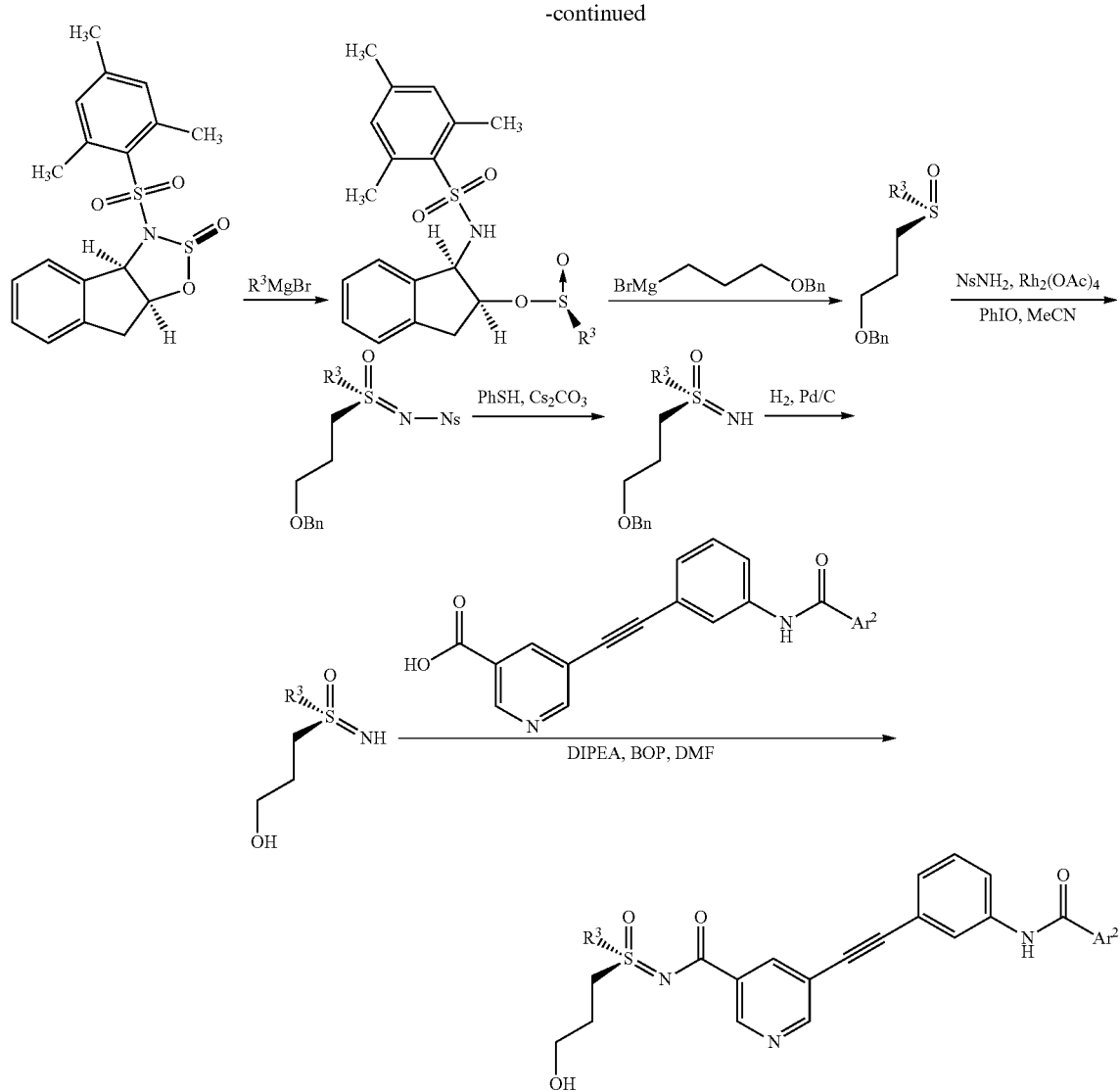

Experimental procedures for the preparation of said examples are illustrated but not limited to the examples provided below.

Preparation 1

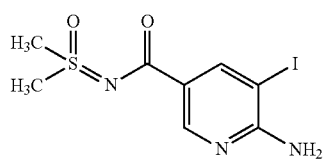

6-Amino-N-[dimethyl(oxido)-λ[1]-sulfanylidene]-5-iodonicotinamide

To a 250 mL round bottom flask containing 5-iodo-6-amino-nicotinic acid (5 g, 18.9 mmol) and dimethylsulfoximine (1.94 g, 1.1 eq) in anhydrous DMF (50 mL) was added diisopropylamine (6.6 mL, 2 eq) and BOP (9.21 g, 1.1 eq) under nitrogen atmosphere. The reaction mixture was heated at 70° C. for 1.5 hours and then partitioned between aq NH₄Cl and EtOAc. The aqueous layer was separated and extracted once with EtOAc. The two organic layers were combined, and washed with saturated aq NaHCO₃/brine (1:1, 1×), brine (1×), and dried with anhydrous Na₂SO₄. The solution layer was decanted, concentrated, and the brown solid residue was treated with EtOAc with stirring at RT for 30 minutes. The solid which formed was colleded by filtration and dried to give the title compound as an offwhite solid (5.31 g, 83%).

Preparation 2

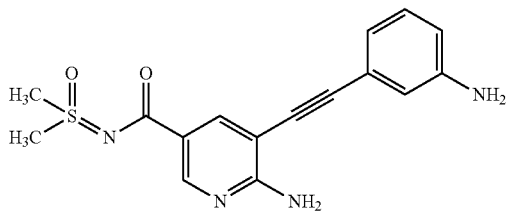 [SMILES: CS(C)(=O)=NC(=O)c1cnc(N)c(C#Cc2cccc(N)c2)c1]

6-Amino-5-[(3-aminophenyl)ethynyl]-N-[dimethyl(oxido)-λ⁴-sulfanylidene]nicotinamide To a 250 mL round bottom flask containing 6-amino-N-[dimethyl(oxido)-λ⁴-sulfanylidene]-5-iodonicotinamide, (6.0 g, 17.8 mmol, 1 eq), bis(triphenylphosphine)palladium (II) dichloride (1.25 g, 0.1 eq), and triphenylphosphine (0.117 g, 0.025 eq) in anhydrous DMF (75 mL) under anhydrous nitrogen atmosphere was added 3-ethynylaniline (2.8 mL, 1.5 eq), triethylamine (10 mL, 4 eq) and copper(I) iodide (0.68 g, 0.2 eq). The reaction mixture was stirred at RT for 15 minutes and the resulting dark brown reaction mixture was partitioned between saturated aq NaHCO₃ and EtOAc. The organic layer was separated, washed with aq NH₄Cl (1×) and brine (1×), followed by drying with anhydrous Na₂SO₄ overnight. The upper solution was decanted and concentrated. The solid residue was treated with EtOAc-hexane (1:4). A yellow solid was obtained when filtered. This solid was treated again with EtOAc-hexane (1:4) with stirring at RT for 30 minutes. The title compound, was obtained as light yellow solid upon filtration and was used directly into next step without further purification.

Example 1

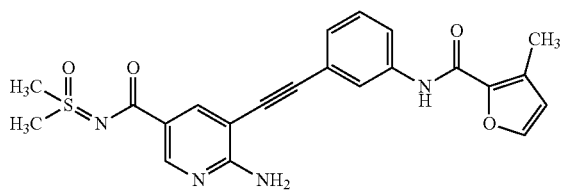 [SMILES: Cc1ccoc1C(=O)Nc1cccc(C#Cc2cc(C(=O)N=S(C)(C)=O)cnc2N)c1]

6-Amino-N-[dimethyl(oxido)-λ⁴-sulfanylidene]-5-({3-[(3-methyl-2-furoyl)amino]phenyl}ethynyl)nicotinamide A solution of 6-amino-5-[(3-aminophenyl)ethynyl]-N-[dimethyl(oxido)-λ⁴-sulfanylidene]nicotinamide (17.8 mmol) in anhydrous DMF (50 mL) under nitrogen atmosphere was treated with 3-methyl-furan-2-carboxylic acid (3.37 g, 1.5 eq), diisopropylamine (12.5 mL, 4.0 equiv.) and BOP (12.2 g, 1.5 equiv.). The reaction mixture was stirred and heated at 60° C. for 1.5 hours. The reaction mixture was partitioned between saturated aq NaHCO₃ and EtOAc. The organic layer was separated, washed with aqueous NH₄Cl (1×) and brine (1×), and dried with anhydrous Na₂SO₄. The upper solution was decanted, concentrated, and subject to a gradient column chromatography [acetone-CHCl₃ 1:30 to 1:4 (with 4% of MeOH in the eluent at a later chromatographic stage)]. It was found that significant amount of the desired product still remained as solid on top of the column in addition to the product eluted out in the fractions. The product fractions were collected, concentrated, and the solid residue obtained was treated with EtOAc with stirring at RT for 30 minutes. The white solid which formed was collected by filtration and dried to give an initial batch of the title compound (2.4 g). The filtrate was combined to the solid which originally resided on the top of the column. This mixture was evaporated under reduced pressure and was then treated with EtOAc and small amount of i-PrOH. The resulting mixture was stirred at RT for 2 hours. The light brown solid which formed was collected by filtration and dried to give a second batch of the title compound (3.5 g). The two batches of solid were combined, treated with water, and stirred at RT for 1 hour and then collected by filtration to give the title compound as a slightly brown solid (4.99 g, 65%).

Example 2

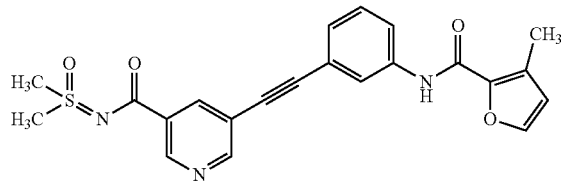 [SMILES: Cc1ccoc1C(=O)Nc1cccc(C#Cc2cncc(C(=O)N=S(C)(C)=O)c2)c1]

N-[Dimethyl(oxido)-λ⁴-sulfanylidene]-5-({3-[(3-methyl-2-furoyl)amino]phenyl}ethynyl)nicotinamide In a manner similar to that described in Example 1, 5-[(3-aminophenyl)ethynyl]-N-[dimethyl(oxido)-λ⁴-sulfanylidene]nicotinamide and 3-methyl-furan-2-carboxylic acid are converted to the title compound.

¹H NMR (DMSO-d₆) δ: 10.21 (s, 1H), 9.08 (d, J=2.0 Hz, 1H), 8.92 (d, J=2.0 Hz, 1H), 8.39 (t, J=2.1 Hz, 1H), 8.13 (t, J=1.6 Hz, 1H), 7.82 (d, J=1.5 Hz, 1H), 7.78-7.81 (m, 1H), 7.39-7.43 (m, 1H), 7.34 (dt, J=7.6, 1.2 Hz, 1H), 6.61 (d, J=1.5 Hz, 1H), 3.52 (s, 6H), 2.35 (s, 3H)

Example 3

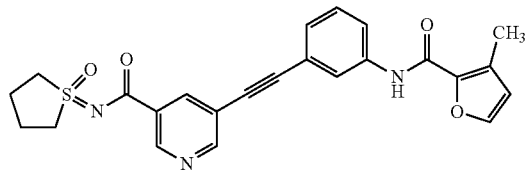 [SMILES: Cc1ccoc1C(=O)Nc1cccc(C#Cc2cncc(C(=O)N=S3(=O)CCCC3)c2)c1]

5-({3-[(3-Methyl-2-furoyl)amino]phenyl}ethynyl)-N-(1-oxidotetrahydro-1H-λ⁴-thien-1-ylidene)nicotinamide In a manner similar to that described in Preparation 1, 5-{3-[(3-Methyl-furan-2-carbonyl)-amino]-phenylethynyl}-nicotinic acid and tetrahydro-1H-λ⁴-thiophen-1-imine 1-oxide are converted to the title compound.

¹H NMR (DMSO-d₆) δ: 10.21 (s, 1H), 9.10 (d, J=2.0 Hz, 1H), 8.93 (d, J=2.0 Hz, 1H), 8.41 (t, J=2.1 Hz, 1H), 8.13 (t, J=1.8 Hz, 1H), 7.82 (d, J=1.5 Hz, 1H), 7.78-7.81 (m, 1H), 7.39-7.43 (m, 1H), 7.34 (d, J=7.6 Hz, 1H), 6.61 (d, J=1.5 Hz, 1H), 3.73 (ddd, J=13.8, 7.1, 7.0 Hz, 2H), 3.48 (dt, J=13.7, 6.8 Hz, 2H), 2.35 (s, 3H), 2.22-2.30 (m, 2H), 2.12-2.20 (m, 2H)

Example 4

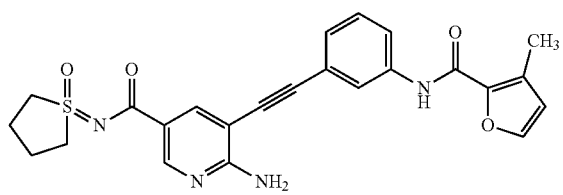 [SMILES: Cc1ccoc1C(=O)Nc1cccc(C#Cc2cc(C(=O)N=S3(=O)CCCC3)cnc2N)c1]

6-Amino-5-({3-[(3-methyl-2-furoyl)amino]phenyl}ethynyl)-N-(1-oxidotetrahydro-1H-1λ⁴-thien-1-ylidene)nicotinamide In a manner similar to that described in Preparation 1, 6-amino-5-{3-[(3-Methyl-furan-2-carbonyl)-amino]-phenylethynyl}-nicotinic acid and tetrahydro-1H-λ⁴-thiophen-1-imine 1-oxide are converted to the title compound.

$^1$H NMR (DMSO-$d_6$) δ: 10.13 (s, 1H), 8.59 (d, J=2.2 Hz, 1H), 8.09 (t, J=1.7 Hz, 1H), 8.07 (d, J=2.2 Hz, 1H), 7.81 (d, J=1.5 Hz, 1H), 7.74 (ddd, J=8.4, 1.5, 1.3 Hz, 1H), 7.40-7.43 (m, 1H), 7.35-7.39 (m, 1H), 7.01 (br. s., 2H), 6.61 (d, J=1.5 Hz, 1H), 3.65 (ddd, J=13.7, 7.2, 7.0 Hz, 2H), 3.40 (dt, J=13.7, 6.8 Hz, 2H), 2.35 (s, 3H), 2.19-2.26 (m, 2H), 2.08-2.17 (m, 2H)

Example 5

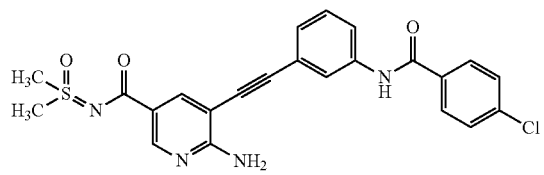 [SMILES: CS(C)(=O)=NC(=O)c1cnc(N)c(C#Cc2cccc(NC(=O)c3ccc(Cl)cc3)c2)c1]

6-Amino-5-({3-[(4-chlorobenzoyl)amino]phenyl}ethynyl)-N-[dimethyl(oxido)-λ⁴-sulfanylidene]nicotinamide In a manner similar to that described in Example 1, 6-amino-5-[(3-aminophenyl)ethynyl]-N-[dimethyl(oxido)-λ⁴-sulfanylidene]nicotinamide and 4-chlorobenzoic acid are converted to the title compound.

$^1$H NMR (DMSO-$d_6$) δ: 10.40 (s, 1H), 8.57 (d, J=2.2 Hz, 1H), 8.05-8.07 (m, 2H), 7.99-8.02 (m, 2H), 7.73-7.76 (m, 1H), 7.61-7.65 (m, 2H), 7.44-7.47 (m, 1H), 7.39-7.43 (m, 1H), 7.00 (br. s., 2H), 3.44 (s, 6H)

Example 6

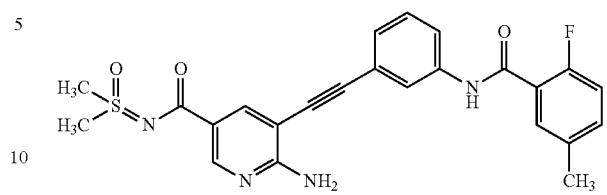

6-amino-N-[dimethyl(oxido))-λ⁴-sulfanylidene]-5-({3-[(2-fluoro-5-methylbenzoyl)amino]phenyl}ethynyl)nicotinamide In a manner similar to that described in Example 1, 6-amino-5-[(3-aminophenyl)ethynyl]-N-[dimethyl(oxido)-λ⁴-sulfanylidene]nicotinamide and 2-fluoro-5-methyl benzoic acid are converted to the title compound.

$^1$H NMR (DMSO-$d_6$) δ: 10.40 (s, 1H), 8.57 (d, J=2.2 Hz, 1H), 8.05-8.07 (m, 2H), 7.99-8.02 (m, 2H), 7.73-7.76 (m, 1H), 7.61-7.65 (m, 2H), 7.44-7.47 (m, 1H), 7.39-7.43 (m, 1H), 7.00 (br. s., 2H), 3.44 (s, 6H), 2.35 (s, 3H).

Example 7

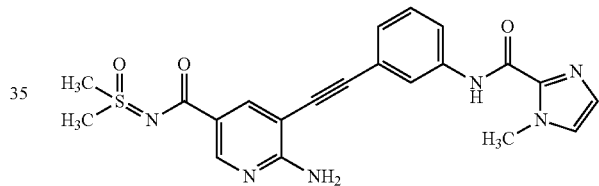

6-Amino-N-[dimethyl(oxido)-λ⁴-sulfanylidene]-5-[(3-{[(1-methyl-1H-imidazol-2-yl)carbonyl]amino}phenyl)ethynyl]nicotinamide In a manner similar to that described in Example 1, 6-amino-5-[(3-aminophenyl)ethynyl]-N-[dimethyl(oxido)-λ⁴-sulfanylidene]nicotinamide and 1-methyl-1H-imidazole-2-carboxylic acid are converted to the title compound.

$^1$H NMR (DMSO-$d_6$) δ: 10.42 (s, 1H), 8.57 (d, J=2.2 Hz, 1H), 8.14 (t, J=1.6 Hz, 1H), 8.05 (d, J=2.2 Hz, 1H), 7.78-7.81 (m, 1H), 7.46 (s, 1H), 7.41-7.44 (m, 1H), 7.36-7.40 (m, 1H), 7.10 (d, J=0.7 Hz, 1H), 6.99 (br. s., 2H), 4.01 (s, 3H), 3.44 (s, 6H)

Preparation 3

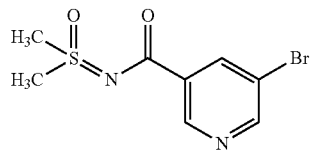

5-Bromo-N-[dimethyl(oxido)-λ⁴-sulfanylidene]nicotinamide

To the mixture of dimethylsulfoximine (4.0 g, 43 mmol, 1 eq) and 5-bromonicotinic acid (9.31 g, 1.05 eq) in anhydrous DMF (85 mL) under nitrogen atmosphere was added diisopropylamine (15 mL, 2.0 eq) and BOP (21.6 g, 1.1 eq). After the reaction was stirred at RT for 15 minutes, it was poured into saturated aq NaHCO$_3$ and extracted with EtOAc. The organic phase was separated, washed sequentially with saturated NaHCO$_3$ (1×), brine (1×), aq NH$_4$Cl (1×), and brine (1×), and finally dried with anhydrous Na$_2$SO$_4$. The upper brown solution was decanted, concentrated, and the brown oily residue was subject to a gradient column chromatography (EtOAc-Hexane 1:4 to 1:1). The corresponding product fractions were collected and concentrated. The solid residue was treated with EtOAc-Hexane (1:7) and the resulting mixture was stirred at RT for 2 hours. The white solid was collected by filtration and dried to give the title compound (8.89 g, 75%).

Preparation 4

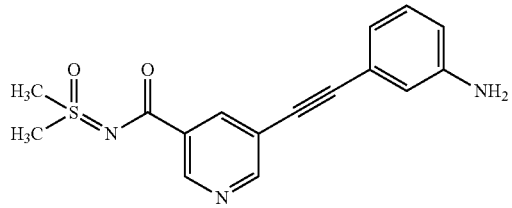 [SMILES: CS(C)(=O)=NC(=O)c1cncc(C#Cc2cccc(N)c2)c1]

5-[(3-Aminophenyl)ethynyl]-N-[dimethyl(oxido)-λ⁴-sulfanylidene]nicotinamide

To a 100 mL round bottom flask containing 5-bromo-N-[dimethyl(oxido)-λ⁴-sulfanylidene]nicotinamide (2.8 g, 10 mmol, 1 eq), bis(triphenylphosphine)palladium(II) dichloride (0.70 g, 0.1 eq), and triphenylphosphine (0.07 g, 0.025 eq) in anhydrous DMF (25 mL) under anhydrous nitrogen atmosphere was added 3-ethynylaniline (1.5 mL, 1.5 eq), triethylamine (5.6 mL, 4 eq) and copper(I) iodide (0.38 g, 0.2 eq). The reaction mixture was stirred at RT for 1.5 hours and then partitioned between saturated aq NaHCO$_3$ and EtOAc. The organic layer was separated, washed sequentially with saturated aq NaHCO$_3$ (1×), aq NH$_4$Cl (1×), and brine (1×), followed by drying with anhydrous Na$_2$SO$_4$. The upper solution was decanted, concentrated, and subject to a gradient column chromatography (EtOAc-hexans 1:4 to 3:1) to give the title compound as a slightly yellow-colored foam (1.72 g, 55%).

Example 8

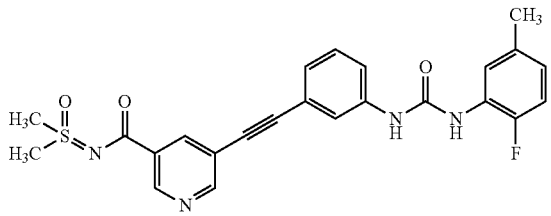 [SMILES: Cc1ccc(F)c(NC(=O)Nc2cccc(C#Cc3cncc(C(=O)N=S(C)(C)=O)c3)c2)c1]

N-[Dimethyl(oxido)-λ⁴-sulfanylidene]-5-{[3-({[(2-fluoro-5-methylphenyl)amino]carbonyl}amino)phenyl]ethynyl}nicotinamide A solution of 5-[(3-aminophenyl)ethynyl]-N-[dimethyl(oxido)-λ⁴-sulfanylidene]nicotinamide, (90 mg, 0.28 mmol, 1 eq) in anhydrous THF (1.5 mL) was treated with 2-fluoro-5-methylphenyl isocyanate (0.05 mL, 1.2 eq) The reaction mixture was then stirred at RT for 1 hour. It was then portioned between saturated aq NaHCO$_3$ and EtOAc. The organic phase was isolated, washed with aq NH$_4$Cl (1×) and brine (1×), and lastly dried with anhydrous Na$_2$SO$_4$. The upper solution was decanted, concentrated, and the resulting yellow solid residue was chromatographed (EtOAc-Hexanes 1:5 to 5:1). Concentration of the product eluting fractions gave the title compound as a white solid (102 mg, 77%).

Example 9

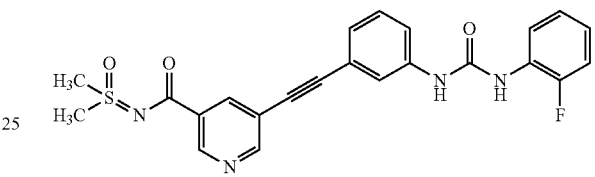

N-[Dimethyl(oxido)-λ⁴-sulfanylidene]-5-{[3-({[(2-fluorophenyl)amino]carbonyl}amino)phenyl]ethynyl}nicotinamide In a manner similar to that described in Example 8, 5-[(3-aminophenyl)ethynyl]-N-[dimethyl(oxido)-λ⁴-sulfanylidene]nicotinamide and 1-fluoro-2-isocyanatobenzene are converted to the title compound.

$^1$H NMR (DMSO-d$_6$) δ: 9.22 (s, 1H), 9.08 (d, J=1.8 Hz, 1H), 8.92 (d, J=2.1 Hz, 1H), 8.61 (d, J=2.1 Hz, 1H), 8.39 (t, J=2.1 Hz, 1H), 8.14 (td, J=8.2, 1.5 Hz, 1H), 7.85-7.87 (m, 1H), 7.36-7.41 (m, 2H), 7.23-7.27 (m, 2H), 7.13-7.17 (m, 1H), 7.01-7.05 (m, 1H), 3.51 (s, 6H)

Example 10

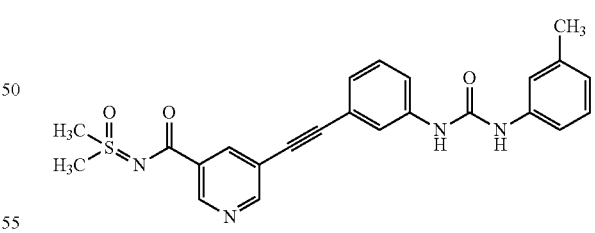

N-[Dimethyl(oxido)-λ⁴-sulfanylidene]-5-{[3-({[(3-methylphenyl)amino]carbonyl}amino)phenyl]ethynyl}nicotinamide In a manner similar to that described in Example 8, 5-[(3-aminophenyl)ethynyl]-N-[dimethyl(oxido)-λ⁴-sulfanylidene]nicotinamide and 1-isocyanato-3-methylbenzene are converted to the title compound.

$^1$H NMR (DMSO-d$_6$) δ: 9.08 (d, J=2.1 Hz, 1H), 8.91 (d, J=2.1 Hz, 1H), 8.82 (s, 1H), 8.67 (s, 1H), 8.38 (t, J=2.1 Hz,

1H), 7.86 (t, J=1.6 Hz, 1H), 7.39-7.41 (m, 1H), 7.35-7.38 (m, 1H), 7.32 (s, 1H), 7.21-7.24 (m, 2H), 7.15-7.18 (m, 1H), 6.81 (d, J=7.3 Hz, 1H), 3.51 (s, 6H), 2.28 (s, 3H)

Example 11

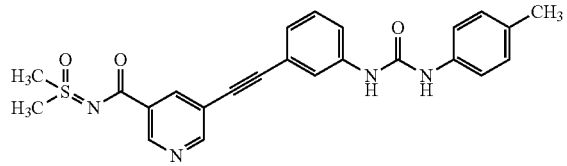

N-[Dimethyl(oxido)-λ⁴-sulfanylidene]-5-{[3-({[(4-methylphenyl)amino]carbonyl}amino)phenyl]ethynyl}nicotinamide In a manner similar to that described in Example 8, 5-[(3-aminophenyl)ethynyl]-N-[dimethyl(oxido)-λ⁴-sulfanylidene]nicotinamide and 1-isocyanato-4-methylbenzene are converted to the title compound.

¹H NMR (DMSO-d₆) δ: 9.08 (d, J=1.8 Hz, 1H), 8.91 (d, J=2.1 Hz, 1H), 8.79 (s, 1H), 8.64 (s, 1H), 8.38 (t, J=1.9 Hz, 1H), 7.84 (t, J=1.6 Hz, 1H), 7.39-7.42 (m, 1H), 7.33-7.38 (m, 3H), 7.22 (ddd, J=7.5, 1.0, 0.9 Hz, 1H), 7.09 (d, J=8.2 Hz, 2H), 3.51 (s, 6H), 2.25 (s, 3H).

Preparation 5

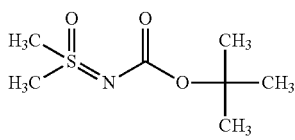

Tert-butyl [dimethyl(oxido)-λ⁴-sulfanylidene]carbamate

To a 100 mL round bottom flask containing a previously prepared crude dimethylsulfoximine (~0.9 g) in anhydrous THF (35 mL) was added di-tert-butyl dicarbonate (4.1 g) and the resulting solution was kept at ambient temperature. Sodium hydride (0.67 g) was carefully added and the reaction mixture was stirred at RT for 5 hours. The reaction was then poured into ice-cooled aq NH₄Cl and was extracted with EtOAc. The organic layer was separated, washed with brine (1×), and dried with Na₂SO₄ overnight. A gradient column chromatography (EtOAc-Hexanes 1:1 to MeOH-EtOAc 1:50) was performed. Concentration of the product eluting fractions provided the title compound as white solid (274 mg).

¹H NMR (DMSO-d₆) δ: 3.27 (s, 6H), 1.37 (s, 9H)

Preparation 6

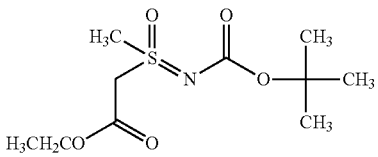

Ethyl [N-(tert-butoxycarbonyl)-S-methylsulfonimidoyl]acetate

A solution of 2,2,6,6-tetramethylpiperidine (0.33 mL, 1.4 eq) in anhydrous THF (1 mL) was cooled to 0° C. To this solution was slowly added n-butyllithium (0.66 mL, 1.2 eq). The resulting reaction mixture was stirred at 0° C. for 10 minutes and then cooled to −78° C. tert-butyl [dimethyl (oxido)-λ⁴-sulfanylidene]carbamate (267 mg, 1.38 mmol, 1 eq) in anhydrous THF (1 mL) was added dropwise and the reaction was first kept at −78° C. for 10 minutes, then warmed to −10° C. within 30 minutes followed by cooling −78° C. Ethyl chloroformate (0.19 mL, 1.4 eq) was added in one portion. The reaction was stirred at −78° C. for 30 minutes and then poured into aq NH₄Cl and extracted with EtOAc. The combined organic extracts were washed with brine and dried over Na₂SO₄. The upper solution layer was decanted and concentrated to give the title compound as a yellow oil (~270 mg).

Preparation 7

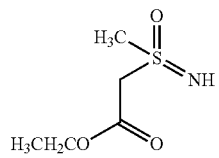

Ethyl(S-methylsulfonimidoyl)acetate

A solution of ethyl [N-(tert-butoxycarbonyl)-S-methylsulfonimidoyl]acetate in dichloromethane (2.5 mL) was cooled to 0° C. followed by a dropwise addition of trifluoroacetic acid (0.79 mL). The reaction was then stirred at RT for 2 hours. The excess TFA was removed under reduced pressure and the oily residue was partitioned between EtOAc and saturated aq NaHCO₃/brine. The organic layer was separated, washed with brine (1×), and dried over Na₂SO₄. The upper solution layer was decanted and concentrated yielding the title compound as a brown oil (49 mg).

Preparation 8

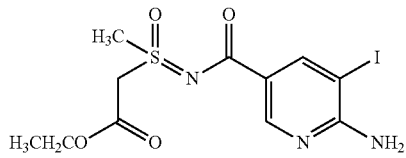

Ethyl {N-[(6-amino-5-iodopyridin-3-yl)carbonyl]-S-methylsulfonimidoyl}acetate

A solution of ethyl(S-methylsulfonimidoyl)acetate was dissolved in anhydrous DMF (1 mL) and treated with 5-iodo-6-amino-nicotinic acid (82 mg, 1.05 eq), diisopropylamine (0.1 mL, 2 eq), and BOP (149 mg, 1.1 eq) with stirring. The reaction mixture was heated to 70° C. for 6 hours and then partitioned between EtOAc and aq NH$_4$Cl. The organic layer was separated, washed with saturated aq NaHCO$_3$ (1×) and brine (1×), and dried over Na$_2$SO$_4$. The organic phase was filtered and concentrated. The residue as purified by gradient column chromatography (EtOAc-Hexane 1:9 to 2:3). Concentration of the product containing fractions provided the title compound as a brown oil (24 mg).

Preparation 9

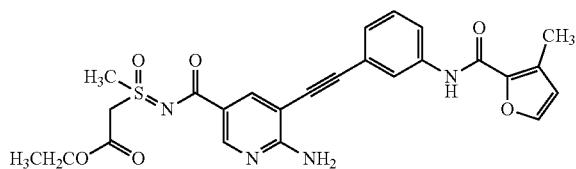

Ethyl(N-{[6-amino-5-({3-[(3-methyl-2-furoyl)amino]phenyl}ethynyl)pyridin-3-yl]carbonyl}-S-methylsulfonimidoyl)acetate A solution of ethyl {N-[(6-amino-5-iodopyridin-3-yl)carbonyl]-S-methylsulfonimidoyl}acetate, (24 mg, 0.06 mmol), 3-methyl-furan-2-carboxylic acid (3-ethynyl-phenyl)-amide (20 mg, 1.5 eq), bis(triphenylphosphine)palladium(II) dichloride (4.1 mg, 0.1 eq), and triphenyl phosphine (0.4 mg, 0.025 eq) in anhydrous DMF (0.5 mL) under a nitrogen atmosphere was added triethylamine (0.05 mL, 5 eq) followed by the addition of copper(I) iodide (2.2 mg, 0.2 eq). The reaction mixture was stirred at RT for 15 minutes and then poured into saturated aq NaHCO$_3$ and extracted with EtOAc (1×). The organic extract was washed with brine (1×) and dried over anhydrous Na$_2$SO$_4$. The organic phase was filtered and concentrated. The residue was purified by chromatography (EtOAc-Hexanes 1:4 to EtOAc). The product containing fractions were combined and concentrated to give the title compound (14 mg, 47%).

$^1$H NMR (DMSO-d$_6$) δ: 10.13 (s, 1H), 8.55 (d, J=2.2 Hz, 1H), 8.07-8.10 (m, 1H), 8.03 (d, J=2.2 Hz, 1H), 7.81 (d, J=1.5 Hz, 1H), 7.71-7.75 (m, 1H), 7.40-7.43 (m, 1H), 7.35-7.39 (m, 1H), 7.06 (br. s., 2H), 6.61 (d, J=1.5 Hz, 1H), 4.94 (d, J=14.4 Hz, 1H), 4.79 (d, J=14.4 Hz, 1H), 4.20 (q, J=7.0 Hz, 2H), 3.54 (s, 3H), 2.35 (s, 3H), 1.21 (t, J=7.1 Hz, 3H).

Example 12

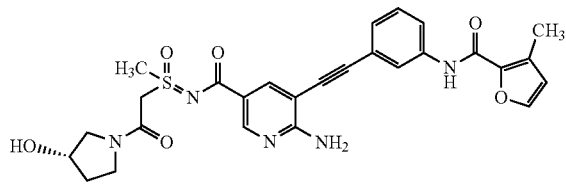 [SMILES: Cc1ccoc1C(=O)Nc1cccc(C#Cc2cc(C(=O)N=S(C)(=O)CC(=O)N3CC[C@H](O)C3)cnc2N)c1]

6-Amino-N-{[2-(3-hydroxypyrrolidin-1-yl)-2-oxoethyl](methyl)oxido-λ$^4$-sulfanylidene}-5-({3-[(3-methyl-2-furoyl)amino]phenyl}ethynyl)nicotinamide To a solution of ethyl(N-{[6-amino-5-({3-[(3-methyl-2-furoyl)amino]phenyl}ethynyl)pyridin-3-yl]carbonyl}-S-methylsulfonimidoyl)acetate (13 mg, 0.025 mmol, 1 eq) in anhydrous THF (1 mL) was added (S)-3-hydroxypyrrolidine (0.021 mL, 10 eq). The reaction was stirred and heated at 70° C. for 2 hours. It was then partitioned between aq NH$_4$Cl and EtOAc. The organic layer was then washed with saturated aq NaHCO$_3$ (1×), brine (1×), and dried over anhydrous Na$_2$SO$_4$. The organic phase was then filtered and concentrated, and the oily residue was subject to purification by gradient column chromatography (EtOAc-Hexane 3:2 to MeOH-EtOAc 1:50). The product containing fractions were combined and concentrated to give the title compound as white solid (7 mg, 50%) as a mixture of two diastereomers.

$^1$H NMR (DMSO-d$_6$) δ: 10.13 (s, 1H), 8.52-8.57 (m, 1H), 8.07-8.10 (m, 1H), 7.99-8.05 (m, 1H), 7.81 (d, J=1.2 Hz, 1H), 7.73 (d, J=8.1 Hz, 1H), 7.39-7.43 (m, 1H), 7.34-7.39 (m, 1H), 7.03 (br. s., 2H), 6.61 (d, J=1.0 Hz, 1H), 4.85-5.12 (m, 2H), 4.61-4.75 (m, 1H), 4.24-4.37 (m, 1H), 3.43-3.80 (m, 7H), 2.35 (s, 3H), 1.74-1.91 (m, 2H)

Preparation 10

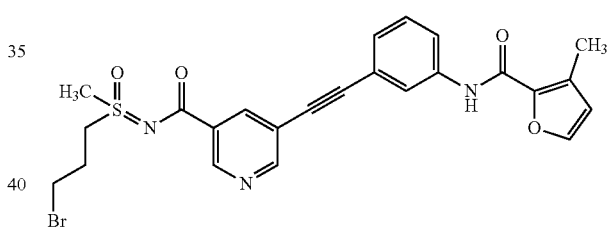

N-[(3-bromopropyl)(methyl)oxido-λ$^4$-sulfanylidene]-5-({3-[(3-methyl-2-furoyl)amino]phenyl}ethynyl)nicotinamide A solution of N-[(3-hydroxypropyl)(methyl)oxido-λ$^4$-sulfanylidene]-5-({3-[(3-methyl-2-furoyl)amino]phenyl}ethynyl)nicotinamide (60 mg, 0.13 mmol) in anhydrous DCM (1 mL) was cooled to 0° C. and treated with carbon tetrabromide (60 mg, 1.4 eq) and triphenylphosphine (48 mg, 1.4 eq). The reaction solution was stirred at RT for about an hour, followed by additional addition of carbon tetrabromide (60 mg) and triphenylphosphine (40 mg). The reaction was stirred for another hour and then poured into saturated aq NaHCO$_3$. The mixture was extracted with DCM, and subsequently washed with aq NH$_4$Cl (1×), brine (1×), and dried with anhydrous Na$_2$SO$_4$. The organic phase was collected, concentrated, and subject to a gradient column chromatography (acetone-hexane 1:10 to 1:1) to give the title compound as white foam (48 mg, 71%).

Example 13

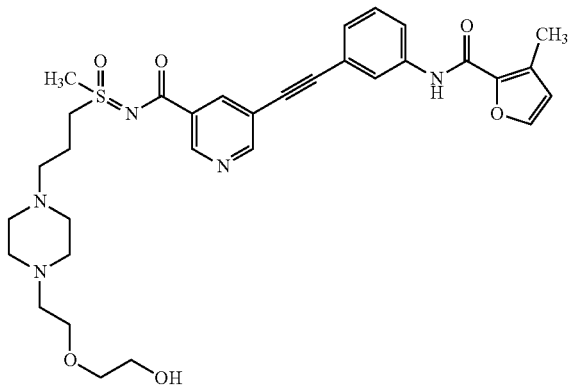 [SMILES: Cc1ccoc1C(=O)Nc1cccc(C#Cc2cncc(C(=O)N=S(C)(=O)CCCN3CCN(CCOCCO)CC3)c2)c1]

N-[(3-{4-[2-(2-hydroxyethoxyl)ethyl]piperazin-1-yl}propyl)(methyl)oxido-λ⁴-sulfanylidene]-5-({3-[(3-methyl-2-furoyl)amino]phenyl}ethynyl)nicotinamide To the solution of N-[(3-bromopropyl)(methyl)oxido-λ⁴-sulfanylidene]-5-({3-[(3-methyl-2-furoyl)amino]phenyl}ethynyl)nicotinamide (46 mg, 0.087 mmol) in anhydrous DMF (1 mL) was dropwise added 1-[2-(2-hydroxyethoxyl)ethyl]piperazine (0.075 mL, 5 eq) and the resulting reaction solution was heated at 60° C. for 40 minutes. It was then partitioned between saturated aq NaHCO₃ and EtOAc. The organic layer was washed with brine (1×) and dried with anhydrous Na₂SO₄. The solution layer was decanted, concentrated, and the oily residue was subject to a gradient column chromatography (MeOH-EtOAc 1:100 to 2:3) to provide the title compound as white foam (42 mg, 78%).

Preparation 11

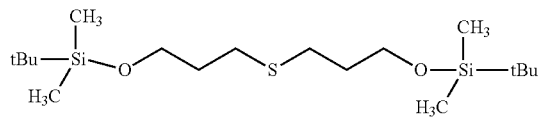

2,2,3,3,13,13,14,14-Octamethyl-4,12-dioxa-8-thia-3,13-disilapentadecane

To a solution of 3,3'-thiodipropanol (5 g, 32.6 mmol, 1 eq) and tert-butyldimethylsilyl chloride (13.18 g, 2.6 eq) in anhydrous DMF (25 mL) at 0° C. was added imidazole (11.21 g, 5 eq). After the reaction was stirred at room temperature for one hour, it was partitioned between ethyl acetate and water. The organic layer was isolated, washed once more with water, then brine, and lastly dried with anhydrous sodium sulfate. The upper clear solution was decanted, concentrated, and the oily residue was subject to a column chromatography (EtOC-Hex: from 1:9 to 4:1). Concentration of the product eluting fractions provided the title compound as a clear oil (12.32 g).

¹H NMR (DMSO-d₆) δ: 3.64 (t, J=6.2 Hz, 4H), 2.49-2.53 (m, 4H), 1.65-1.71 (m, 4H), 0.86 (s, 18H), 0.03 (s, 12H)

Preparation 12

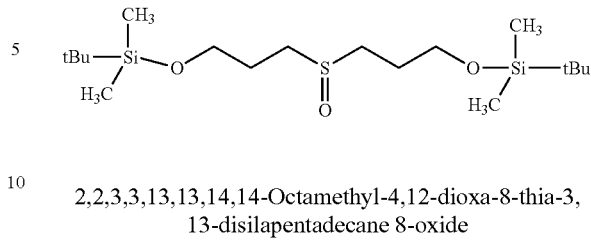

2,2,3,3,13,13,14,14-Octamethyl-4,12-dioxa-8-thia-3,13-disilapentadecane 8-oxide

A solution of sodium (meta)periodate (7.751 g, 1.1 eq) in water (40 mL) was slowly poured into a solution of 2,2,3,3,13,13,14,14-octamethyl-4,12-dioxa-8-thia-3,13-disilapentadecane (12.32 g, 1 eq) in methanol (150 mL) at 0° C. and the reaction mixture was stirred at room temperature for 2 hours. The reaction mixture was then filtered through a pad of celite and silica gel which was washed with methanol. The filtrate was concentrated under reduced pressure at a temperature below 25° C. The residue was diluted with brine and extracted a couple of times with chloroform. All organic solvents were combined, dried with anhydrous sodium sulfate, and concentrated to give the title compound as a clear oil (12.84 g).

¹H NMR (DMSO-d₆) δ: 3.69 (t, J=6.2 Hz, 4H), 2.59-2.83 (m, 4H), 1.80 (tdd, J=6.8, 6.7, 6.4 Hz, 4H), 0.86 (s, 18H), 0.04 (s, 12H)

Preparation 13

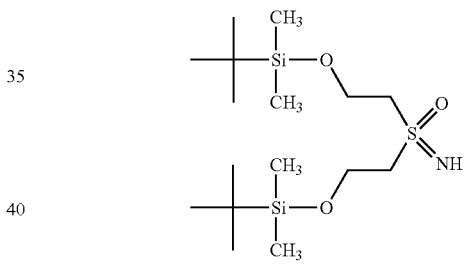

8-Imino-2,2,3,3,13,13,14,14-Octamethyl-4,12-dioxa-8λ⁴-thia-3,13-disilapentadecane 8-oxide To a solution of 2,2,3,3,13,13,14,14-octamethyl-4,12-dioxa-8-thia-3,13-disilapentadecane 8-oxide in anhydrous dichloromethane (150 mL) was added trifluoroacetamide (7.60 g, 2 eq), magnesium oxide (5.256 g. 4 eq), rhodium acetate dimer (432 mg, 0.03 eq), and (diacetoxyiodo)benzene (15.75 g, 1.5 eq) under nitrogen atmosphere at room temperature. The greenish reaction mixture was stirred at room temperature for 18 hours. Then additional amount of trifluoroacetamide (3.0 g), rhodium acetate dimer (300 mg), (diacetoxyiodo)benzene (5.0 g), and anhydrous DCM (100 mL) was added. The mixture was stirred at room temperature for another 3 hours and then filtered through a pad of celite and silica gel. The pad was washed first with DCM followed by MeOH-DCM (1:5). The filtrate was concentrated and the brown oil was taken up into methanol (200 mL). Potassium carbonate (22.53 g, 5 eq) was added to the newly formed solution. After the mixture was stirred at room temp for 2 hours, it was filtered through a pad of celite and silica gel. The pad was washed first with DCM-EtOAC (1:1) followed by a later 10% (v/v) addition of MeOH with stirring of the sediment on top of the pad. The filtrate was concentrated and the residue mixture was treated with DCM-EtOAc (2:3) with stirring at room temp for 30 minutes. The mixture was filtered again through a pad of celite and silica gel. This filtration and concentration circle may be repeated a couple of times such that most of the solid by-product was removed and a reddish oil was obtained. Purification by a gradient column chromatography (EtOAc-HEX 1:20 to 1:1) provided the title compound as a redish oil (9.538 g) with a total yield of 72% for 4 steps.

$^1$H NMR (DMSO-d$_6$) δ: 3.67 (t, J=6.3 Hz, 4H), 3.65 (s, 1H), 2.99 (t, J=7.9 Hz, 4H), 1.82-1.88 (m, 4H), 0.86 (s, 18H), 0.04 (s, 12H)

Preparation 14

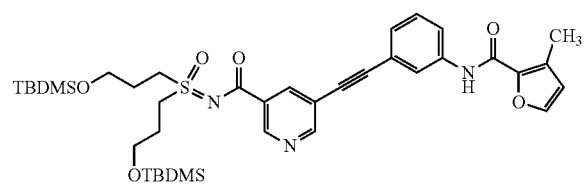 [SMILES: Cc1ccoc1C(=O)Nc1cccc(C#Cc2cncc(C(=O)N=S(=O)(CCCO[Si](C)(C)C(C)(C)C)CCCO[Si](C)(C)C(C)(C)C)c2)c1]

N-[Bis(3-{[tert-butyl(dimethyl)silyl]oxy}propyl)(oxido)-λ$^4$-sulfanylidene]-5-({3-[(3-methyl-2-furoyl)amino]phenyl}ethynyl)nicotinamide A solution of 8-imino-2,2,3,3,13,13,14,14-octamethyl-4,12-dioxa-8λ$^4$-thia-3,13-disilapentadecane 8-oxide (1.227 g, 3 mmol, 1 eq), 5-{3-[(3-Methyl-furan-2-carbonyl)-amino]-phenylethynyl}-nicotinic acid (1.053 g, 1 eq), DMAP (73.5 mg, 0.2 eq), and EDCI (690 mg, 1.2 eq) in anhydrous DCE (30 mL) was heated at 60° C. for 3 hours. The reaction mixture was then diluted with DCM, washed sequentially with aqueous NH$_4$Cl, saturated aqueous NaHCO$_3$, and brine, and lastly dried with anhydrous sodium sulfate. The upper clear solution was decanted, concentrated, and the oily residue was subject to a gradient column chromatography (EtOAc-Hex 1:100 to 1:3) to give the title compound as a white foam (1.53 g).

$^1$H NMR (DMSO-d$_6$) δ: 10.20 (s, 1H), 9.07 (d, J=2.1 Hz, 1H), 8.92 (d, J=2.1 Hz, 1H), 8.37 (t, J=2.1 Hz, 1H), 8.14 (t, J=1.8 Hz, 1H), 7.81 (d, J=1.5 Hz, 1H), 7.77-7.79 (m, 1H), 7.41 (t, J=7.9 Hz, 1H), 7.31-7.34 (m, 1H), 6.61 (d, J=1.2 Hz, 1H), 3.70-3.76 (m, 6H), 3.63-3.69 (m, 2H), 2.35 (s, 3H), 1.93-2.05 (m, 4H), 0.86 (s, 18H), 0.04 (s, 12H)

Example 14

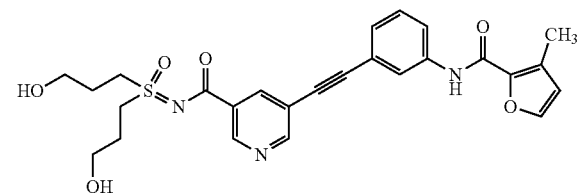 [SMILES: Cc1ccoc1C(=O)Nc1cccc(C#Cc2cncc(C(=O)N=S(=O)(CCCO)CCCO)c2)c1]

N-[Bis(3-hydroxypropyl)(oxido)-λ$^4$-sulfanylidene]-5-({3-[(3-methyl-2-furoyl)amino]phenyl}ethynyl)nicotinamide To a solution of N-[bis(3-{[tert-butyl(dimethyl)silyl]oxy}propyl)(oxido)-λ$^4$-sulfanylidene]-5-({3-[(3-methyl-2-furoyl)amino]phenyl}ethynyl)nicotinamide (1.48 g, 2.0 mmol, 1 eq) in anhydrous THF (40 mL) at 0° C. was added dropwise tetrabutylammonium fluoride (8.23 mL, 1.0 M in anhyd. THF, 4.1 eq) and the reaction was stirred at that temp for 3 hours. The reaction was then concentrated at room temperature and partitioned between saturated aqueous NaHCO$_3$ and ethyl acetate. The organic layer was washed with aqueous NH$_4$Cl, brine, lastly dried with anhydrous Na$_2$SO$_4$. The organic layer was decanted, concentrated, and the oily residue was subject to a gradient column chromatography (EtOAc-Hex 1:1 to MeOH-EtOAc 1:25). Concentration of the product eluting fractions gave the title compound as a white foam (574 mg).

$^1$H NMR (DMSO-d$_6$) δ: 10.20 (s, 1H), 9.09 (d, J=1.8 Hz, 1H), 8.92 (d, J=2.1 Hz, 1H), 8.38 (t, J=2.1 Hz, 1H), 8.12 (t, J=1.6 Hz, 1H), 7.82 (d, J=1.5 Hz, 1H), 7.79-7.81 (m, 1H), 7.39-7.43 (m, 1H), 7.34 (dt, J=7.9, 1.2 Hz, 1H), 6.61 (d, J=1.5 Hz, 1H), 4.76 (t, J=5.3 Hz, 2H), 3.69-3.75 (m, 2H), 3.62-3.68 (m, 2H), 3.54 (q, J=6.1 Hz, 4H), 2.35 (s, 3H), 1.88-2.00 (m, 4H)

Preparation 15

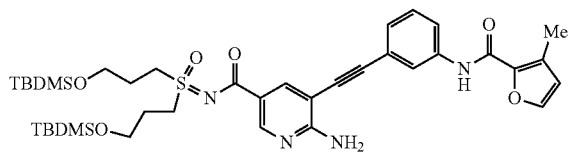 [SMILES: Cc1ccoc1C(=O)Nc1cccc(C#Cc2cc(C(=O)N=S(=O)(CCCO[Si](C)(C)C(C)(C)C)CCCO[Si](C)(C)C(C)(C)C)cnc2N)c1]

6-Amino-N-[bis(3-{[tert-butyl(dimethyl)silyl]oxy}propyl)(oxido)-λ$^4$-sulfanylidene]-5-({3-[(3-methyl-2-furoyl)amino]phenyl}ethynyl)nicotinamide In a manner similar to that described in Preparation 14, a mixture of 8-imino-2,2,3,3,13,13,14,14-octamethyl-4,12-dioxa-8λ$^4$-thia-3,13-disilapentadecane 8-oxide and 6-amino-5-{3-[(3-methyl-furan-2-carbonyl)-amino]-phenylethynyl}-nicotinic acid were converted to the title compound Example 15

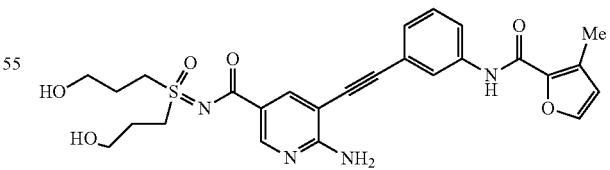

6-amino-N-[bis(3-hydroxypropyl)(oxido)-λ$^4$-sulfanylidene]-5-({3-[(3-methyl-2-furoyl)amino]phenyl}ethynyl)nicotinamide In a manner similar to that described in Example 14, 6-amino-N-[bis(3-{[tert-butyl(dimethyl)silyl]oxy}propyl)

(oxido)-λ⁴-sulfanylidene]-5-({3-[(3-methyl-2-furoyl)amino]phenyl}ethynyl)nicotinamide was converted to the title compound.

¹H NMR (DMSO-d₆) δ: 10.13 (s, 1H), 8.58 (d, J=2.3 Hz, 1H), 8.07 (t, J=1.8 Hz, 1H), 8.04 (d, J=2.1 Hz, 1H), 7.81 (d, J=1.5 Hz, 1H), 7.73-7.76 (m, 1H), 7.40-7.43 (m, 1H), 7.35-7.39 (m, 1H), 6.99 (br. s., 2H), 6.60 (d, J=1.5 Hz, 1H), 4.74 (t, J=5.4 Hz, 2H), 3.61-3.67 (m, 2H), 3.55-3.60 (m, 2H), 3.53 (q, J=6.1 Hz, 4H), 2.35 (s, 3H), 1.85-1.96 (m, 4H)

Preparation 16

Methyl 5-((3-(4-chloro-3-(trifluoromethyl)benzamido)phenyl)ethynyl)nicotinate

In a manner similar to that described in Example 1, methyl 5-((3-aminophenyl)ethynyl)nicotinate and 4-chloro-3-(trifluoromethyl)benzoic acid are converted to the title compound.

Preparation 17

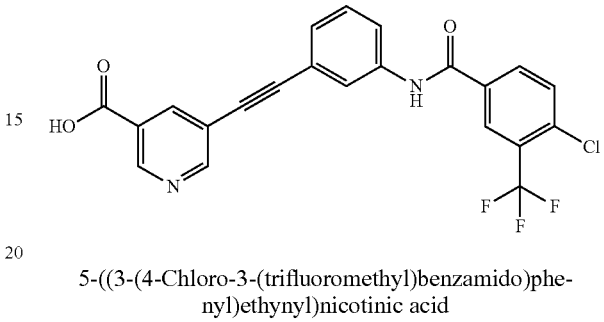

5-((3-(4-Chloro-3-(trifluoromethyl)benzamido)phenyl)ethynyl)nicotinic acid

In a manner similar to that described in Preparation 42, methyl 5-((3-(4-chloro-3-(trifluoromethyl)benzamido)phenyl)ethynyl)nicotinate is converted to the title compound.

Preparation 18

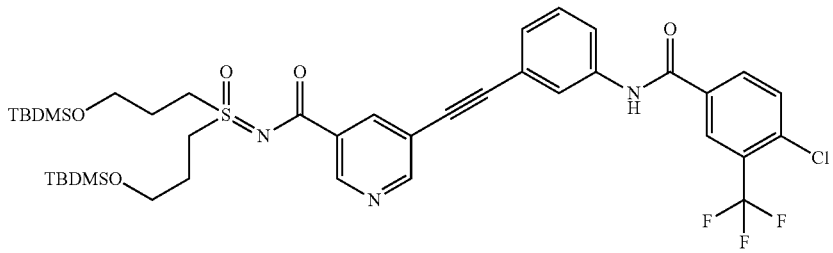 [SMILES: CC(C)(C)[Si](C)(C)OCCCS(=O)(CCCO[Si](C)(C)C(C)(C)C)=NC(=O)c1cncc(C#Cc2cccc(NC(=O)c3ccc(Cl)c(C(F)(F)F)c3)c2)c1]

N-[Bis(3-{[tert-butyl(dimethyl)silyl]oxy}propyl)(oxido)-λ⁴-sulfanylidene]-5-[(3-{[4-chloro-3-(trifluoromethyl)benzoyl]amino}phenyl)ethynyl]nicotinamide In a manner similar to that described in Preparation 14, a mixture of 8-imino-2,2,3,3,13,13,14,14-octamethyl-4,12-dioxa-8λ⁴-thia-3,13-disilapentadecane 8-oxide and 5-((3-(4-chloro-3-(trifluoromethyl)benzamido)phenyl)ethynyl)nicotinic acid were converted to the title compound Example 16

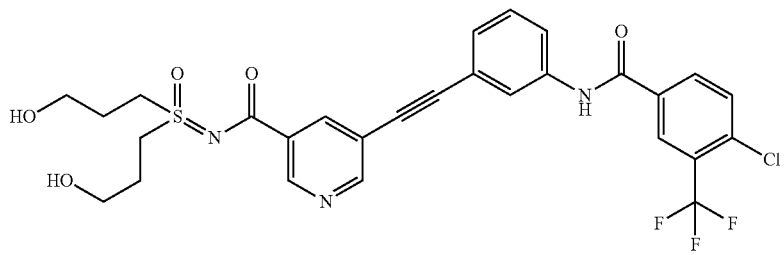 [SMILES: O=C(N=S(=O)(CCCO)CCCO)c1cncc(C#Cc2cccc(NC(=O)c3ccc(Cl)c(C(F)(F)F)c3)c2)c1]

N-[Bis(3-hydroxypropyl)(oxido)-λ⁴-sulfanylidene]-5-[(3-{[4-chloro-3-(trifluoromethyl)benzoyl]amino}phenyl)ethynyl]nicotinamide In a manner similar to that described in Example 14, N-[bis(3-{[tert-butyl(dimethyl)silyl]oxy}propyl)(oxido)-λ⁴-sulfanylidene]-5-[(3-{[4-chloro-3-(trifluoromethyl)benzoyl]amino}phenyl)ethynyl]nicotinamide was converted to the title compound.

¹H NMR (DMSO-d₆) δ: 10.65 (s, 1H), 9.10 (d, J=2.1 Hz, 1H), 8.93 (d, J=2.1 Hz, 1H), 8.41 (d, J=1.8 Hz, 1H), 8.39 (t, J=2.1 Hz, 1H), 8.28 (dd, J=8.2, 1.8 Hz, 1H), 8.08 (t, J=1.6 Hz, 1H), 7.95 (d, J=8.2 Hz, 1H), 7.80-7.83 (m, 1H), 7.48 (t, J=7.9 Hz, 1H), 7.41 (dt, J=7.6, 1.2 Hz, 1H), 4.76 (t, J=5.3 Hz, 2H), 3.69-3.75 (m, 2H), 3.62-3.68 (m, 2H), 3.54 (q, J=6.1 Hz, 4H), 1.89-2.00 (m, 4H)

Preparation 19

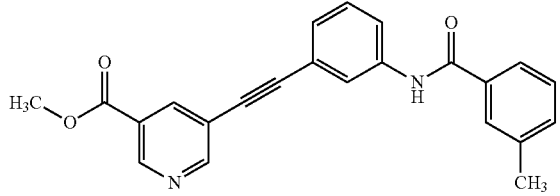 [SMILES: COC(=O)c1cncc(C#Cc2cccc(NC(=O)c3cccc(C)c3)c2)c1]

Methyl 5-((3-(3-methylbenzamido)phenyl)ethynyl)nicotinate

In a manner similar to that described in Example 1, methyl 5-((3-aminophenyl)ethynyl)nicotinate and 3-methylbenzoic acid are converted to the title compound.

Preparation 20

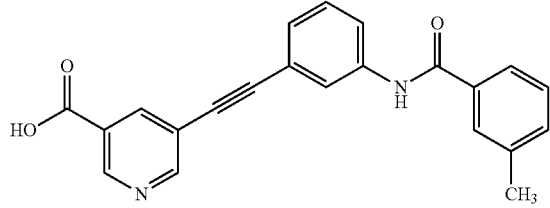 [SMILES: Cc1cccc(C(=O)Nc2cccc(C#Cc3cncc(C(=O)O)c3)c2)c1]

5-((3-(3-Methylbenzamido)phenyl)ethynyl)nicotinic acid

In a manner similar to that described in Preparation 42, methyl 5-((3-(3-methylbenzamido)phenyl)ethynyl)nicotinate is converted to the title compound.

Preparation 21

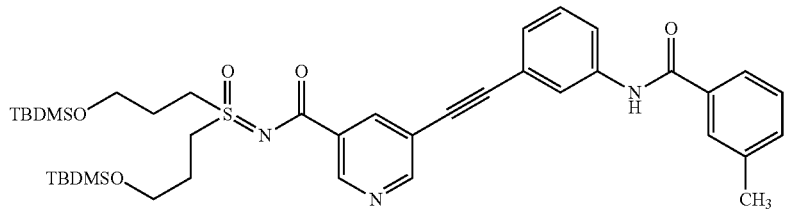 [SMILES: Cc1cccc(C(=O)Nc2cccc(C#Cc3cncc(C(=O)N=S(=O)(CCCO[Si](C)(C)C(C)(C)C)CCCO[Si](C)(C)C(C)(C)C)c3)c2)c1]

N-[Bis(3-{[tert-butyl(dimethyl)silyl]oxy}propyl)(oxido)-λ⁴-sulfanylidene]-5-({3-[(3-methylbenzoyl)amino]phenyl}ethynyl)nicotinamide In a manner similar to that described in Preparation 14, a mixture of 8-imino-2,2,3,3,13,13,14,14-octamethyl-4,12-dioxa-8λ⁴-thia-3,13-disilapentadecane 8-oxide and 5-((3-(3-methylbenzamido)phenyl)ethynyl)nicotinic acid were converted to the title compound

Example 17

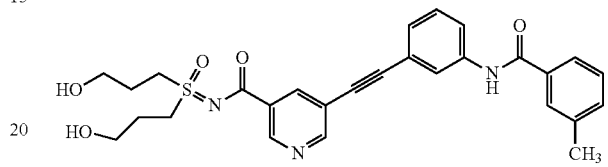

N-[Bis(3-hydroxypropyl)(oxido)-λ⁴-sulfanylidene]-5-({3-[(3-methylbenzoyl)amino]phenyl}ethynyl)nicotinamide In a manner similar to that described in Example 14, N-[bis(3-{[tert-butyl(dimethyl)silyl]oxy}propyl)(oxido)-λ⁴-sulfanylidene]-5-({3-[(3-methylbenzoyl)amino]phenyl}ethynyl)nicotinamide was converted to the title compound.

¹H NMR (DMSO-d₆) δ: 10.34 (s, 1H), 9.10 (d, J=1.8 Hz, 1H), 8.92 (d, J=2.1 Hz, 1H), 8.38 (t, J=2.1 Hz, 1H), 8.11 (t, J=1.8 Hz, 1H), 7.82-7.84 (m, 1H), 7.79 (s, 1H), 7.76 (ddd, J=6.0, 2.1, 1.9 Hz, 1H), 7.42-7.47 (m, 3H), 7.37 (dt, J=7.6, 1.2 Hz, 1H), 4.76 (t, J=5.3 Hz, 2H), 3.69-3.75 (m, 2H), 3.62-3.68 (m, 2H), 3.54 (q, J=5.9 Hz, 4H), 2.41 (s, 3H), 1.89-2.00 (m, 4H)

Preparation 22

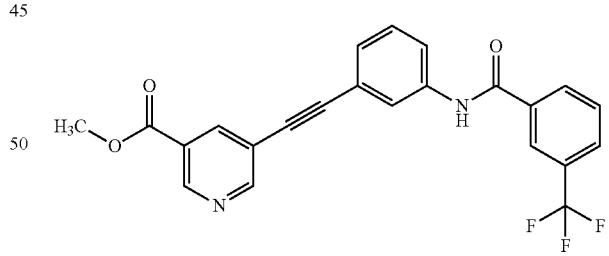

Methyl 5-((3-(3-(trifluoromethyl)benzamido)phenyl)ethynyl)nicotinate

In a manner similar to that described in Example 1, methyl 5-((3-aminophenyl)ethynyl)nicotinate and 3-(trifluoromethyl)benzoic acid are converted to the title compound.

Preparation 23

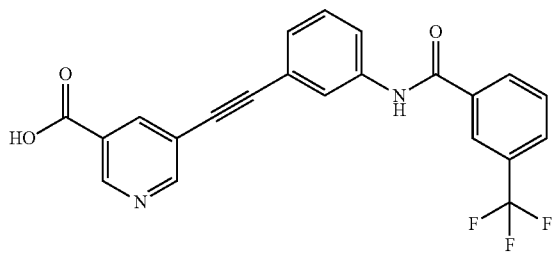 [SMILES: O=C(O)c1cncc(C#Cc2cccc(NC(=O)c3cccc(C(F)(F)F)c3)c2)c1]

5-((3-(3-(Trifluoromethyl)benzamido)phenyl)ethynyl)nicotinic acid

In a manner similar to that described in Preparation 42, methyl 5-((3-(3-(trifluoromethyl)benzamido)phenyl)ethynyl)nicotinate is converted to the title compound.

Preparation 24

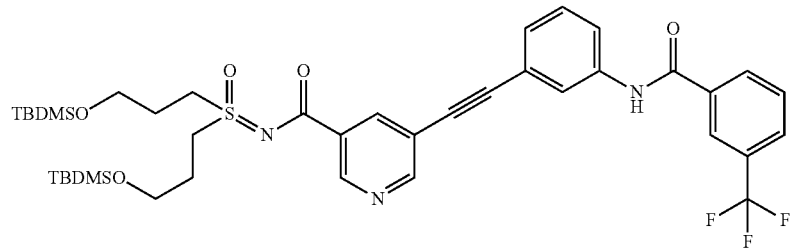 [SMILES: CC(C)(C)[Si](C)(C)OCCCS(=O)(CCCO[Si](C)(C)C(C)(C)C)=NC(=O)c1cncc(C#Cc2cccc(NC(=O)c3cccc(C(F)(F)F)c3)c2)c1]

N-[Bis(3-{[tert-butyl(dimethyl)silyl]oxy}propyl)(oxido)-$\lambda^4$-sulfanylidene]-5-[(3-{[3-(trifluoromethyl)benzoyl]amino}phenyl)ethynyl]nicotinamide In a manner similar to that described in Preparation 14, a mixture of 8-imino-2,2,3,3,13,13,14,14-octamethyl-4,12-dioxa-8$\lambda^4$-thia-3,13-disilapentadecane 8-oxide and 5-((3-(3-(trifluoromethyl)benzamido)phenyl)ethynyl)nicotinic acid were converted to the title compound.

Example 18

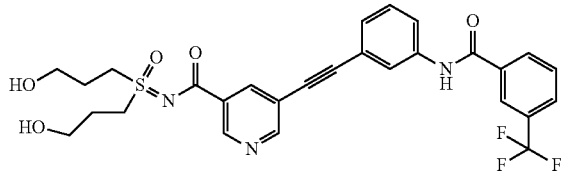 [SMILES: O=C(N=S(=O)(CCCO)CCCO)c1cncc(C#Cc2cccc(NC(=O)c3cccc(C(F)(F)F)c3)c2)c1]

N-[Bis(3-hydroxypropyl)(oxido)-$\lambda^4$-sulfanylidene]-5-[(3-{[3-(trifluoromethyl)benzoyl]amino}phenyl)ethynyl]nicotinamide In a manner similar to that described in Example 14, N-[bis(3-{[tert-butyl(dimethyl)silyl]oxy}propyl)(oxido)-$\lambda^4$-sulfanylidene]-5-[(3-{[3-(trifluoromethyl)benzoyl]amino}phenyl)ethynyl]nicotinamide was converted to the title compound.

$^1$H NMR (DMSO-$d_6$) δ: 10.60 (s, 1H), 9.10 (d, J=2.1 Hz, 1H), 8.93 (d, J=2.1 Hz, 1H), 8.39 (t, J=2.1 Hz, 1H), 8.32 (s, 1H), 8.28 (d, J=7.9 Hz, 1H), 8.10 (t, J=1.6 Hz, 1H), 7.99 (d, J=7.6 Hz, 1H), 7.83-7.85 (m, 1H), 7.81 (t, J=7.9 Hz, 1H), 7.48 (t, J=7.9 Hz, 1H), 7.39-7.42 (m, 1H), 4.76 (t, J=5.3 Hz, 2H), 3.69-3.75 (m, 2H), 3.62-3.68 (m, 2H), 3.54 (q, J=5.9 Hz, 4H), 1.88-2.00 (m, 4H)

Preparation 25

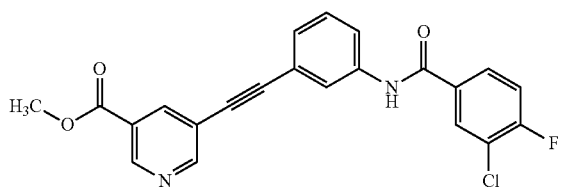 [SMILES: COC(=O)c1cncc(C#Cc2cccc(NC(=O)c3ccc(F)c(Cl)c3)c2)c1]

Methyl 5-((3-(3-chloro-4-fluorobenzamido)phenyl)ethynyl)nicotinate

In a manner similar to that described in Example 1, methyl 5-((3-aminophenyl)ethynyl)nicotinate and 3-chloro-4-fluorobenzoic acid are converted to the title compound.

Preparation 26

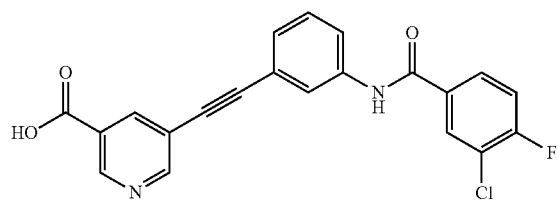 [SMILES: O=C(O)c1cncc(C#Cc2cccc(NC(=O)c3ccc(F)c(Cl)c3)c2)c1]

5-((3-(3-Chloro-4-fluorobenzamido)phenyl)ethynyl)nicotinic acid

In a manner similar to that described in Preparation 42, methyl 5-((3-(3-chloro-4-fluorobenzamido)phenyl)ethynyl)nicotinate is converted to the title compound.

Preparation 27

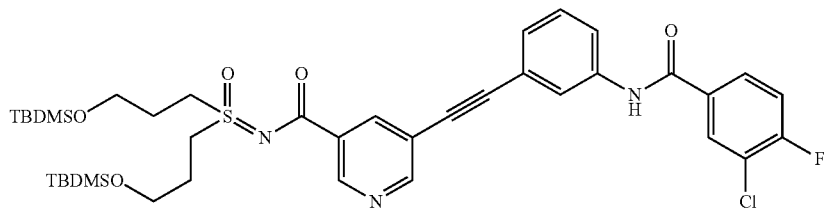 [SMILES: CC(C)(C)[Si](C)(C)OCCCS(=O)(CCCO[Si](C)(C)C(C)(C)C)=NC(=O)c1cncc(C#Cc2cccc(NC(=O)c3ccc(F)c(Cl)c3)c2)c1]

N-[Bis(3-{[tert-butyl(dimethyl)silyl]oxy}propyl)
(oxido)-λ⁴-sulfanylidene]-5-({3-[(3-chloro-4-fluo-
robenzoyl)amino]phenyl}ethynyl)nicotinamide In a manner similar to that described in Preparation 14, a mixture of 8-imino-2,2,3,3,13,13,14,14-octamethyl-4,12-dioxa-8λ⁴-thia-3,13-disilapentadecane 8-oxide and 5-((3-(3-chloro-4-fluorobenzamido)phenyl)ethynyl)nicotinic acid were converted to the title compound Example 19

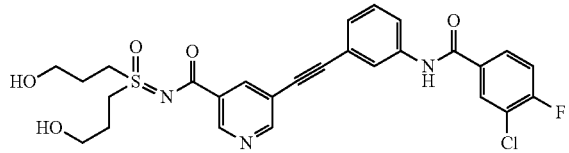 [SMILES: O=C(N=S(=O)(CCCO)CCCO)c1cncc(C#Cc2cccc(NC(=O)c3ccc(F)c(Cl)c3)c2)c1]

N-[Bis(3-hydroxypropyl)(oxido)-λ⁴-sulfanylidene]-
5-({3-[(3-chloro-4-fluorobenzoyl)amino]
phenyl}ethynyl)nicotinamide In a manner similar to that described in Example 14, N-[bis (3-{[tert-butyl(dimethyl)silyl]oxy}propyl)(oxido)-λ⁴-sulfanylidene]-5-({3-[(3-chloro-4-fluorobenzoyl)amino] phenyl}ethynyl)nicotinamide was converted to the title compound.

¹H NMR (DMSO-d₆) δ: 10.48 (s, 1H), 9.10 (d, J=2.1 Hz, 1H), 8.92 (d, J=2.1 Hz, 1H), 8.38 (t, J=2.1 Hz, 1H), 8.22 (dd, J=7.0, 2.3 Hz, 1H), 8.08 (t, J=1.8 Hz, 1H), 8.01 (ddd, J=8.8, 4.7, 2.3 Hz, 1H), 7.80-7.82 (m, 1H), 7.62 (t, J=8.8 Hz, 1H), 7.47 (t, J=7.9 Hz, 1H), 7.39 (dt, J=7.6, 1.2 Hz, 1H), 4.76 (t, J=5.3 Hz, 2H), 3.69-3.75 (m, 2H), 3.62-3.68 (m, 2H), 3.54 (q, J=5.9 Hz, 4H), 1.88-2.00 (m, 4H).

Preparation 28

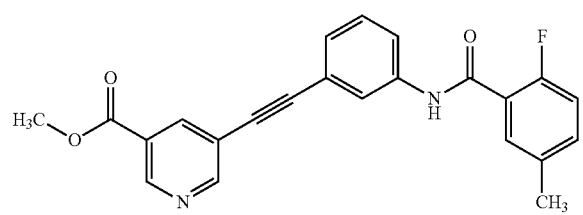 [SMILES: COC(=O)c1cncc(C#Cc2cccc(NC(=O)c3cc(C)ccc3F)c2)c1]

Methyl 5-((3-(2-fluoro-5-methylbenzamido)phenyl)
ethynyl)nicotinate

In a manner similar to that described in Example 1, methyl 5-((3-aminophenyl)ethynyl)nicotinate and 2-fluoro-5-methylbenzoic acid are converted to the title compound.

Preparation 29

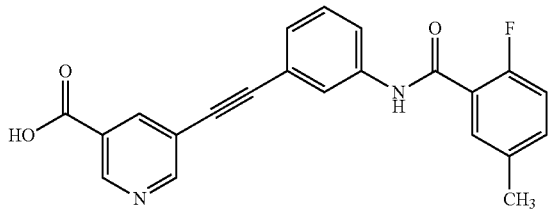 [SMILES: Cc1ccc(F)c(C(=O)Nc2cccc(C#Cc3cncc(C(=O)O)c3)c2)c1]

5-((3-(2-Fluoro-5-methylbenzamido)phenyl)ethynyl)
nicotinic acid

In a manner similar to that described in Preparation 42, methyl 5-((3-(2-fluoro-5-methylbenzamido)phenyl)ethynyl) nicotinate is converted to the title compound.

Preparation 30

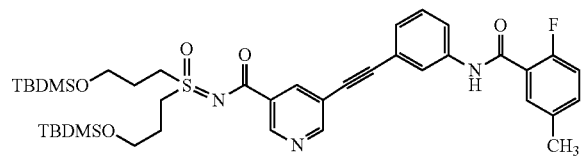 [SMILES: Cc1ccc(F)c(C(=O)Nc2cccc(C#Cc3cncc(C(=O)N=S(=O)(CCCO[Si](C)(C)C(C)(C)C)CCCO[Si](C)(C)C(C)(C)C)c3)c2)c1]

N-[Bis(3-{[tert-butyl(dimethyl)silyl]oxy}propyl)
(oxido)-λ⁴-sulfanylidene]-5-({3-[(2-fluoro-5-methyl-
benzoyl)amino]phenyl}ethynyl)nicotinamide In a manner similar to that described in Preparation 14, a mixture of 8-imino-2,2,3,3,13,13,14,14-octamethyl-4,12-dioxa-8λ⁴-thia-3,13-disilapentadecane 8-oxide and 5-((3-(2-fluoro-5-methylbenzamido)phenyl)ethynyl)nicotinic acid were converted to the title compound

Example 20

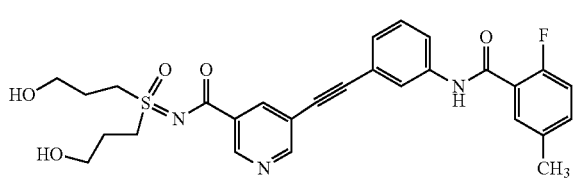 [SMILES: Cc1ccc(F)c(C(=O)Nc2cccc(C#Cc3cncc(C(=O)N=S(=O)(CCCO)CCCO)c3)c2)c1]

N-[Bis(3-hydroxypropyl)(oxido)-λ⁴-sulfanylidene]-5-({3-[(2-fluoro-5-methylbenzoyl)amino]phenyl}ethynyl)nicotinamide In a manner similar to that described in Example 14, N-[bis(3-{[tert-butyl(dimethyl)silyl]oxy}propyl)(oxido)-λ⁴-sulfanylidene]-5-({3-[(2-fluoro-5-methylbenzoyl)amino]phenyl}ethynyl)nicotinamide was converted to the title compound.

¹H NMR (DMSO-d$_6$) δ: 10.53 (s, 1H), 9.09 (d, J=1.8 Hz, 1H), 8.93 (d, J=2.1 Hz, 1H), 8.38 (t, J=2.1 Hz, 1H), 8.06 (s, 1H), 7.73 (d, J=7.9 Hz, 1H), 7.49 (dd, J=6.7, 1.8 Hz, 1H), 7.45 (t, J=7.9 Hz, 1H), 7.37-7.41 (m, 2H), 7.25 (dd, J=9.8, 8.7 Hz, 1H), 4.76 (t, J=5.3 Hz, 2H), 3.69-3.75 (m, 2H), 3.61-3.67 (m, 2H), 3.54 (q, J=5.9 Hz, 4H), 2.35 (s, 3H), 1.88-2.00 (m, 4H)

Preparation 31

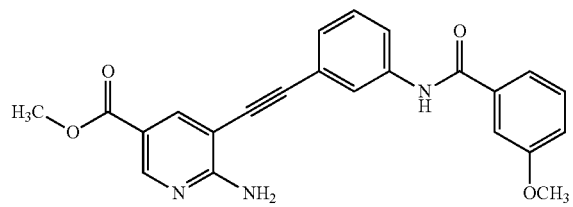 [SMILES: COC(=O)c1cnc(N)c(C#Cc2cccc(NC(=O)c3cccc(OC)c3)c2)c1]

Methyl 6-amino-5-((3-(3-methoxybenzamido)phenyl)ethynyl)nicotinate

In a manner similar to that described in Example 1, methyl 6-amino-5-((3-aminophenyl)ethynyl)nicotinate and 3-methoxybenzoic acid are converted to the title compound.

Preparation 32

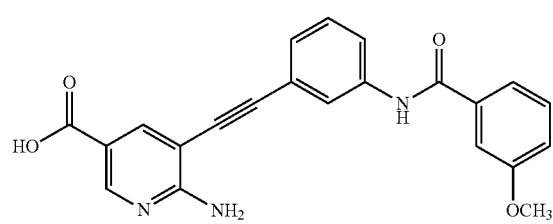 [SMILES: COc1cccc(C(=O)Nc2cccc(C#Cc3cc(C(=O)O)cnc3N)c2)c1]

6-Amino-5-((3-(3-methoxybenzamido)phenyl)ethynyl)nicotinic acid

In a manner similar to that described in Preparation 42, methyl 6-amino-5-((3-(3-methoxybenzamido)phenyl)ethynyl)nicotinate is converted to the title compound.

Preparation 33

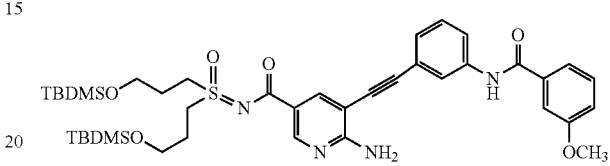

6-Amino-N-[bis(3-{[tert-butyl(dimethyl)silyl]oxy}propyl)(oxido)-λ⁴-sulfanylidene]-5-({3-[(3-methoxybenzoyl)amino]phenyl}ethynyl)nicotinamide In a manner similar to that described in Preparation 14, a mixture of 8-imino-2,2,3,3,13,13,14,14-octamethyl-4,12-dioxa-8λ⁴-thia-3,13-disilapentadecane 8-oxide and 6-amino-5-((3-(3-methoxybenzamido)phenyl)ethynyl)nicotinic acid were converted to the title compound

Example 21

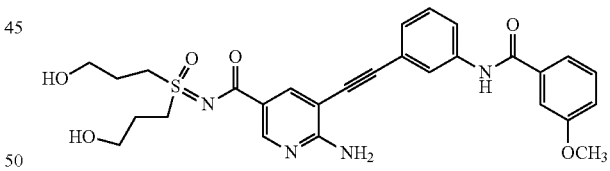

6-Amino-N-[bis(3-hydroxypropyl)(oxido)-λ⁴-sulfanylidene]-5-({3-[(3-methoxybenzoyl)amino]phenyl}ethynyl)nicotinamide In a manner similar to that described in Example 14, 6-amino-N-[bis(3-{[tert-butyl(dimethyl)silyl]oxy}propyl)(oxido)-λ⁴-sulfanylidene]-5-({3-[(3-methoxybenzoyl)amino]phenyl}ethynyl)nicotinamide was converted to the title compound.

¹H NMR (DMSO-d$_6$) δ: 10.68 (br. s., 1H), 8.56 (d, J=2.3 Hz, 1H), 8.04 (d, J=2.1 Hz, 1H), 7.99 (br. s., 1H), 7.68 (d, J=6.5 Hz, 1H), 7.58-7.63 (m, 2H), 7.34 (t, J=7.3 Hz, 1H), 7.21-7.30 (m, 2H), 7.03 (d, J=5.6 Hz, 1H), 6.93 (br. s., 2H), 5.03 (br. s., 2H), 3.82 (s, 3H), 3.61-3.68 (m, 2H), 3.54-3.60 (m, 2H), 3.52 (t, J=6.2 Hz, 4H), 1.85-1.96 (m, 4H)

Preparation 34

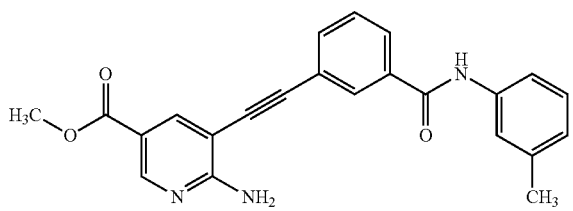 [SMILES: COC(=O)c1cnc(N)c(C#Cc2cccc(C(=O)Nc3cccc(C)c3)c2)c1]

Methyl 6-amino-5-((3-(m-tolylcarbamoyl)phenyl)ethynyl)nicotinate

In a manner similar to that described in Example 1, 3-((2-amino-5-(methoxycarbonyl)pyridin-3-yl)ethynyl)benzoic acid and m-toluidine are converted to the title compound.

Preparation 35

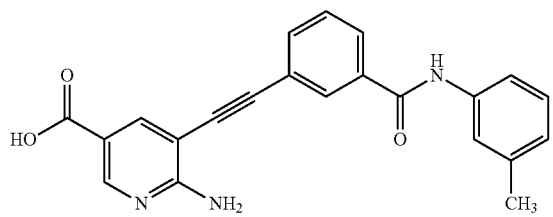 [SMILES: Cc1cccc(NC(=O)c2cccc(C#Cc3cc(C(=O)O)cnc3N)c2)c1]

6-Amino-5-((3-(m-tolylcarbamoyl)phenyl)ethynyl)nicotinic acid

In a manner similar to that described in Preparation 42, methyl 6-amino-5-((3-(m-tolylcarbamoyl)phenyl)ethynyl)nicotinate is converted to the title compound.

Preparation 36

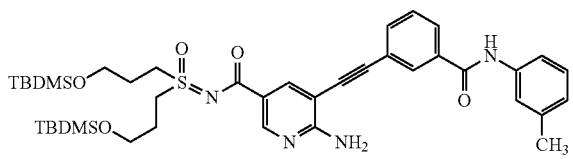 [SMILES: Cc1cccc(NC(=O)c2cccc(C#Cc3cc(C(=O)N=S(=O)(CCCO[Si](C)(C)C(C)(C)C)CCCO[Si](C)(C)C(C)(C)C)cnc3N)c2)c1]

6-Amino-N-[bis(3-{[tert-butyl(dimethyl)silyl]oxy}propyl)(oxido)-λ$^4$-sulfanylidene]-5-[(3-{[(3-methylphenyl)amino]carbonyl}phenyl)ethynyl]nicotinamide In a manner similar to that described in Preparation 14, a mixture of 8-imino-2,2,3,3,13,13,14,14-octamethyl-4,12-dioxa-8λ$^4$-thia-3,13-disilapentadecane 8-oxide and 6-amino-5-((3-(m-tolylcarbamoyl)phenyl)ethynyl)nicotinic acid were converted to the title compound.

Example 22

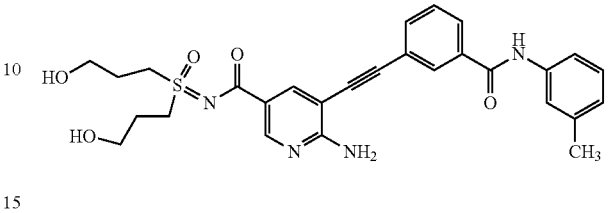

6-Amino-N-[bis(3-hydroxypropyl)(oxido)-λ$^4$-sulfanylidene]-5-[(3-{[(3-methylphenyl)amino]carbonyl}phenyl)ethynyl]nicotinamide In a manner similar to that described in Example 14, 6-amino-N-[bis(3-{[tert-butyl(dimethyl)silyl]oxy}propyl)(oxido)-λ$^4$-sulfanylidene]-5-[(3-{[(3-methylphenyl)amino]carbonyl}phenyl)ethynyl]nicotinamide was converted to the title compound.
$^1$H NMR (DMSO-d$_6$) δ: 10.25 (s, 1H), 8.59 (d, J=2.1 Hz, 1H), 8.26 (t, J=1.5 Hz, 1H), 8.08 (d, J=2.3 Hz, 1H), 7.93 (ddt, J=7.9, 1.0, 0.8 Hz, 1H), 7.89 (ddd, J=7.8, 1.3, 1.2 Hz, 1H), 7.63 (s, 1H), 7.56-7.59 (m, 2H), 7.24 (t, J=7.9 Hz, 1H), 7.09 (br. s., 2H), 6.94 (d, J=7.6 Hz, 1H), 4.74 (t, J=5.3 Hz, 2H), 3.64 (ddd, J=14.1, 10.6, 5.3 Hz, 2H), 3.55-3.60 (m, 2H), 3.53 (q, J=5.9 Hz, 4H), 2.32 (s, 3H), 1.85-1.96 (m, 4H)

Preparation 37

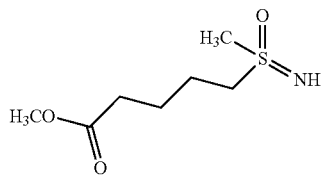

Methyl 5-(S-methylsulfonimidoyl)pentanoate

To a solution of dimethylsulfoximine (4 g, 43 mmol, 1 eq) in anhydrous acetonitrile (10 mL) was added dropwise N,N-diethyltrimethylsilylamine (12.6 mL, 1.5 eq). The reaction solution was stirred and heated at 70° C. for 1 hour. It was then concentrated and dried in vacuo yielding brown oil 5.86 g. The residual TMS-protected dimethylsulfoximine (5.86 g, 35.5 mmol) was dissolved in anhydrous THF (40 mL) and cooled to −78° C. The resulting solution was treated dropwise with n-Butyllithium (14.6 mL, 1.025 eq) and the resulting reaction mixture was stirred at −78° C. for 10 minutes. The reaction flask was lifted out of the bath with stirring for 15 minutes followed by an addition of hexamethyl phosphoramide (11.75 mL, 1.9 eq). The reaction solution was cooled back to −78° C. It was then added dropwise into a solution of trimethyl 4-bromo-orthobutyrate (15.4 g, 1.5 eq) at −78° C. with vigorous stirring. One hour later, the reaction was warmed to RT and stirred for 2.5 hours. The reaction was quenched by pouring into ice cold water which was maintained at pH about 6 with addition of 2 N aq HCl. The aqueous was extracted with EtOAc. The organic layer was isolated, washed with brine (1×), and dried with anhydrous Na₂SO₄. The upper solution was decanted and concentrated yielding brown oil which was used without purification.

The brown oil, obtained in the above step, was dissolved in MeOH—H₂O (10:1, 22 mL). To this solution was added cesium fluoride (0.81 g, 0.15 eq). The resulting reaction mixture was stirred and heated at 50° C. for 3 hours. It was then evaporated under reduced pressure to remove the MeOH. The oily residue was partitioned between cold brine and EtOAc. Mass spectrometry revealed that the desired product remained mostly in the aqueous. Thus, the EtOAc layer was extracted with H₂O (1×). The water layer was then combined to the brine layer, and this aqueous was extracted with i-PrOH—CHCl₃ (1:4, 2×). The organic layers were combined, dried with anhydrous Na₂SO₄, and concentrated under reduced pressure leading to brown oil in amount of 3.2 g. The crude brown oil was dissolved in MeOH—H₂O (40:1, 70 mL). It was then cooled to 0° C. followed by an addition of catalytic amount of pyridinium toluene-4-sulfonate. After the reaction was stirred at 0° C. for 2 hours, it was concentrated under reduced pressure to give the title compound as a brown oil (2.32 g), which was used without further purification.

Preparation 38

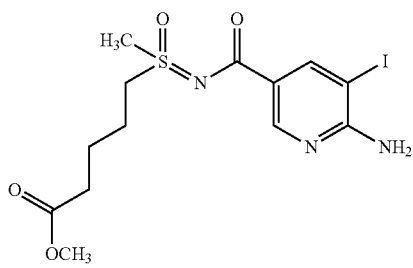 [SMILES: COC(=O)CCCCS(C)(=O)=NC(=O)c1cnc(N)c(I)c1]

Methyl 5-{N-[(6-amino-5-iodopyridin-3-yl)carbonyl]-S-methylsulfonimidoyl}pentanoate A solution of methyl 5-(S-methylsulfonimidoyl)pentanoate (2.32 g) was dissolved in anhydrous DMF (30 mL) and to this solution was added 5-iodo-6-amino-nicotinic acid (3.17 g, ~1 eq), diisopropylethylamine (4.2 mL, 2 eq), and BOP (5.85 g, 1.1 eq). The reaction mixture was heated at 70° C. for 1 hour and then partitioned between EtOAc and aq NH₄Cl. The organic layer was separated, washed sequentially with aq NH₄Cl (1×), saturated aq NaHCO₃ (1×), brine (1×), and dried with anhydrous Na₂SO₄ overnight. The upper solution layer was decanted, concentrated, and the brown oily reside was subject to column chromatography (acetone-CHCl₃ 1:100 to MeOH-acetone-CHCl₃ 1:2:50). Concentration of the product eluting fractions provided the title compound as a slight yellow colored foam (2.65 g).

¹H NMR (DMSO-d₆) δ: 8.52 (d, J=2.1 Hz, 1H), 8.31 (d, J=1.9 Hz, 1H), 6.72 (br. s., 2H), 3.52-3.63 (m, 5H), 3.38 (s, 3H), 2.39 (t, J=7.2 Hz, 2H), 1.61-1.86 (m, 4H)

Example 23

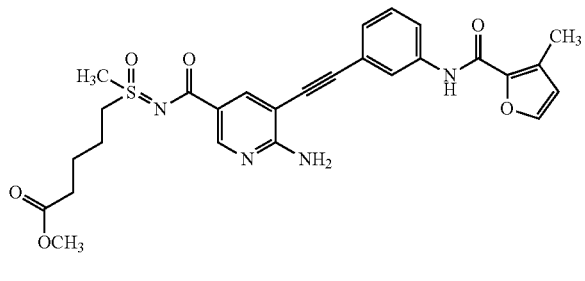 [SMILES: COC(=O)CCCCS(C)(=O)=NC(=O)c1cnc(N)c(C#Cc2cccc(NC(=O)c3occc3C)c2)c1]

Methyl 5-(N-{[6-amino-5-({3-[(3-methyl-2-furoyl)amino]phenyl}ethynyl)pyridin-3-yl]carbonyl}-S-methylsulfonimidoyl)pentanoate The solution of methyl 5-{N-[(6-amino-5-iodopyridin-3-yl)carbonyl]-S-methylsulfonimidoyl}pentanoate, (565 mg, 1.28 mmol) in anhydrous DMF (7 mL) was degassed with anhydrous nitrogen and then to the solution was added 3-methyl-furan-2-carboxylic acid (3-ethynyl-phenyl)-amide (376.5 mg, 1.3 eq), bis(triphenylphosphine)palladium(II) dichloride (90.3 mg, 0.1 eq), triphenyl phosphine (8.4 mg, 0.025 eq), triethylamine (0.75 mL, 4 eq) and lastly copper(I) iodide (50 mg, 0.2 eq) under anhydrous nitrogen atmosphere. The reaction mixture was stirred at RT for about 15 minutes and then partitioned between saturated aq NaHCO₃ and EtOAc. The organic layer was washed one more time with saturated aq NaHCO₃, then with aq NH₄Cl (1×), brine (1×), and dried with anhydrous Na₂SO₄ overnight. The upper solution layer was decanted and concentrated. The oily residue was subject to gradient column chromatography. Concentration of the product eluting fractions gave the title compound as white foam (480 mg, 70%).

¹H NMR (DMSO-d₆) δ: 10.12 (s, 1H), 8.57 (d, J=2.3 Hz, 1H), 8.08 (t, J=1.8 Hz, 1H), 8.04 (d, J=2.2 Hz, 1H), 7.81 (dd, J=1.7, 0.4 Hz, 1H), 7.72-7.75 (m, 1H), 7.40-7.42 (m, 1H), 7.34-7.39 (m, 1H), 6.98 (br. s., 2H), 6.60 (dd, J=1.7, 0.4 Hz, 1H), 3.51-3.65 (m, 5H), 3.40 (s, 3H), 2.40 (t, J=7.4 Hz, 2H), 2.35 (s, 3H), 1.75-1.88 (m, 2H), 1.66-1.72 (m, 2H)

Example 24

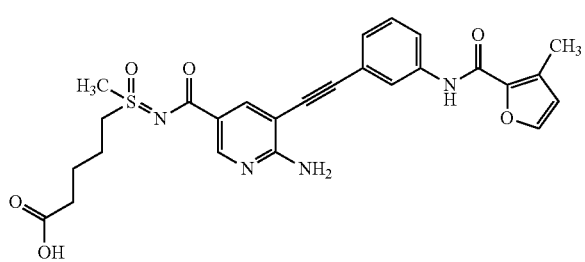 [SMILES: Cc1ccoc1C(=O)Nc1cccc(C#Cc2cc(C(=O)N=S(C)(=O)CCCCC(=O)O)cnc2N)c1]

5-(N-{[6-amino-5-({3-[(3-methyl-2-furoyl)amino]phenyl}ethynyl)pyridin-3-yl]carbonyl}-S-methylsulfonimidoyl)pentanoic acid To the solution of methyl 5-(N-{[6-amino-5-({3-[(3-methyl-2-furoyl)amino]phenyl}ethynyl)pyridin-3-yl]carbonyl}-S-methylsulfonimidoyl)pentanoate (367 mg, 0.68 mmol) in THF (13 mL) at 0° C. was added dropwise 1N aq KOH (3.42 mL, 5 eq). The reaction was stirred at 0° C. for 20 minutes and then at RT for 4 hours. It was then cooled back to 0° C. and 2N aq HCl was dropwise added to adjust the pH to about 5-6. The mixture was then evaporated at RT to remove the most of the THF. The oily residue was then partitioned between aq NH₄Cl and CHCl₃. The chloroform layer was isolated, followed by a wash with brine (1×) and then dried with anhydrous Na₂SO₄ overnight. The upper clear solution was decanted, concentrated, and subject to a gradient column chromatography (MeOH-DCM 1:500 to 1:9). The corresponding product fractions were collected, concentrated, and treated with EtOAc with stirring. The title compound was obtained upon filtration as white solid (238 mg, 67%).

¹H NMR (DMSO-d₆) δ: 12.10 (br. s., 1H), 10.13 (s, 1H), 8.57 (d, J=2.3 Hz, 1H), 8.08 (t, J=1.6 Hz, 1H), 8.04 (d, J=2.1 Hz, 1H), 7.81 (d, J=1.8 Hz, 1H), 7.73-7.76 (m, 1H), 7.40-7.43 (m, 1H), 7.35-7.39 (m, 1H), 6.98 (br. s., 2H), 6.60 (d, J=1.5 Hz, 1H), 3.53-3.64 (m, 2H), 3.40 (s, 3H), 2.35 (s, 3H), 2.27 (t, J=6.9 Hz, 2H), 1.76-1.86 (m, 2H), 1.62-1.68 (m, 2H)

Preparation 39

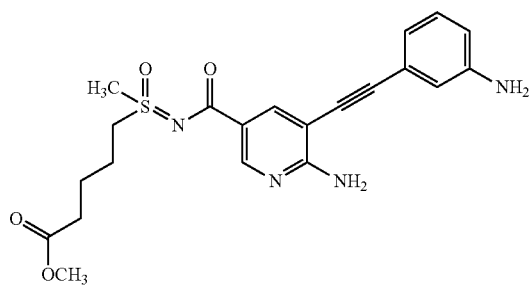 [SMILES: COC(=O)CCCCS(C)(=O)=NC(=O)c1cnc(N)c(C#Cc2cccc(N)c2)c1]

Methyl 5-[N-({6-amino-5-[(3-aminophenyl)ethynyl]pyridin-3-yl}carbonyl)-S-methylsulfonimidoyl]pentanoate To the reaction vessel containing methyl 5-{N-[(6-amino-5-iodopyridin-3-yl)carbonyl]-S-methylsulfonimidoyl}pentanoate (2.0 g, 4.56 mmol, 1 eq), 3-ethynylaniline (0.715 mL, 1.5 eq), and bis(triphenylphosphine)palladium(II) dichloride (320 mg, 0.1 eq) in anhydrous DMF (10 mL) under anhydrous nitrogen atmosphere was added triethylamine (2.54 mL, 4 eq) and copper(I) iodide (173 mg, 0.2 eq). The reaction mixture was stirred at RT for 15 minutes and then partitioned between saturated aq NaHCO₃ and EtOAc. The organic layer was separated, washed with aq NH₄Cl (1×) and brine (1×), followed by drying with anhydrous Na₂SO₄. The upper clear liquid was decanted, concentrated, and the brown oily residue was subject twice to a gradient column chromatography (EtOAc-Hex from 1:3 to MeOH-EtOAc-Hex 1:30:6). Concentration of the product eluting fractions provided the title compound as a white foam (1.32 g, 68%).

¹H NMR (DMSO-d₆) δ: 8.54 (d, J=2.2 Hz, 1H), 7.99 (d, J=2.2 Hz, 1H), 7.04 (t, J=8.0 Hz, 1H), 6.85 (s, 2H), 6.78-6.81 (m, 2H), 6.58-6.61 (m, 1H), 5.20 (s, 2H), 3.52-3.64 (m, 5H), 3.40 (s, 3H), 2.40 (t, J=7.3 Hz, 2H), 1.75-1.87 (m, 2H), 1.65-1.73 (m, 2H)

Example 25

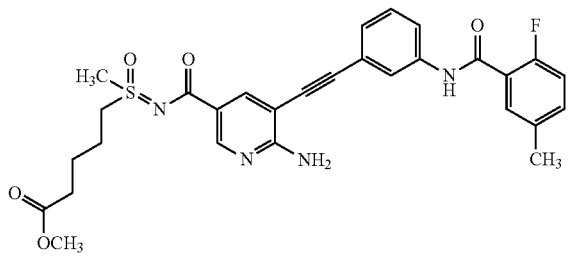

Methyl 5-(N-{[6-amino-5-({3-[(2-fluoro-5-methylbenzoyl)amino]phenyl}ethynyl)pyridin-3-yl]carbonyl}-S-methylsulfonimidoyl)pentanoate To the mixture of methyl 5-[N-({6-amino-5-[(3-aminophenyl)ethynyl]pyridin-3-yl}carbonyl)-S-methylsulfonimidoyl]pentanoate, (85.6 mg, 0.2 mmol, 1 eq) and 2-fluoro-5-methylbenzoic acid (32.7 mg, 1.05 eq) in dichloroethane (2 mL) at 60° C. was added catalytic amount of DMAP (5 mg, 0.2 eq) and EDCI (46.1 mg, 1.2 eq). The reaction was stirred at that temperature for 4 h and then cooled to room temperature. It was then partitioned between EtOAc and saturated aq NaHCO₃. The organic layer was further washed with aq NH₄Cl, brine and then dried with anhydrous sodium sulfate. The organic layer was decanted, concentrated, and the residue was subject to a gradient column chromatography (EtOAc-Hex 1:4 to neat EtOAc). The product containing fractions were concentrated to give the title compound as a white foam (92 mg).

¹H NMR (DMSO-d₆) δ: 10.46 (s, 1H), 8.57 (d, J=2.1 Hz, 1H), 8.04 (d, J=2.1 Hz, 1H), 8.01 (s, 1H), 7.68 (d, J=8.1 Hz, 1H), 7.46-7.49 (m, 1H), 7.43-7.46 (m, 1H), 7.36-7.42 (m, 2H), 7.24 (t, J=9.2 Hz, 1H), 7.00 (br. s., 2H), 3.53-3.64 (m, 5H), 3.40 (s, 3H), 2.40 (t, J=7.3 Hz, 2H), 2.35 (s, 3H), 1.75-1.86 (m, 2H), 1.66-1.72 (m, 2H)

Example 26

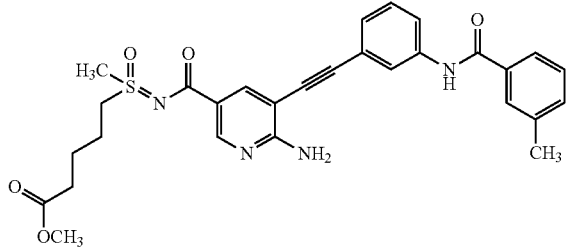 [SMILES: COC(=O)CCCCS(C)(=O)=NC(=O)c1cnc(N)c(C#Cc2cccc(NC(=O)c3cccc(C)c3)c2)c1]

Methyl 5-(N-{[6-amino-5-({3-[(3-methylbenzoyl)amino]phenyl}ethynyl)pyridin-3-yl]carbonyl}-S-methylsulfonimidoyl)pentanoate In a manner similar to that described in Example 25, methyl 5-[N-({6-amino-5-[(3-aminophenyl)ethynyl]pyridin-3-yl}carbonyl)-S-methylsulfonimidoyl]pentanoate and 3-methylbenzoic acid were coupled to give the title compound as a white foam (82 mg).

¹H NMR (DMSO-d₆) δ: 10.29 (s, 1H), 8.57 (d, J=2.2 Hz, 1H), 8.01-8.10 (m, 2H), 7.72-7.82 (m, 3H), 7.35-7.47 (m, 4H), 6.99 (br. s., 2H), 3.52-3.66 (m, 5H), 3.40 (s, 3H), 2.36-2.44 (m, 5H), 1.74-1.87 (m, 2H), 1.65-1.73 (m, 2H)

Example 27

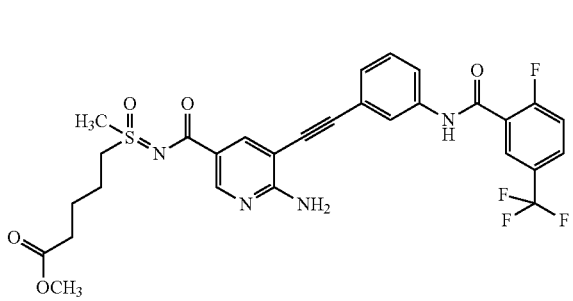 [SMILES: COC(=O)CCCCS(C)(=O)=NC(=O)c1cnc(N)c(C#Cc2cccc(NC(=O)c3cc(C(F)(F)F)ccc3F)c2)c1]

Methyl 5-[N-({6-amino-5-[(3-{[2-fluoro-5-(trifluoromethyl)benzoyl]amino}phenyl)ethynyl]pyridin-3-yl}carbonyl)-S-methylsulfonimidoyl]pentanoate In a manner similar to that described in Example 25, methyl 5-[N-({6-amino-5-[(3-aminophenyl)ethynyl]pyridin-3-yl}carbonyl)-S-methylsulfonimidoyl]pentanoate and 2-fluoro-5-(trifluoromethyl)benzoic acid were coupled to give the title compound as a white foam (74 mg).

¹H NMR (DMSO-d₆) δ: 10.70 (s, 1H), 8.57 (d, J=2.2 Hz, 1H), 8.09 (dd, J=6.1, 2.0 Hz, 1H), 8.05 (d, J=2.1 Hz, 1H), 8.00 (br. s., 2H), 7.68 (d, J=8.1 Hz, 1H), 7.64 (t, J=9.0 Hz, 1H), 7.47-7.49 (m, 1H), 7.41-7.45 (m, 1H), 7.02 (br. s., 2H), 3.53-3.64 (m, 5H), 3.40 (s, 3H), 2.40 (t, J=7.3 Hz, 2H), 1.76-1.86 (m, 2H), 1.65-1.72 (m, 2H)

Example 28

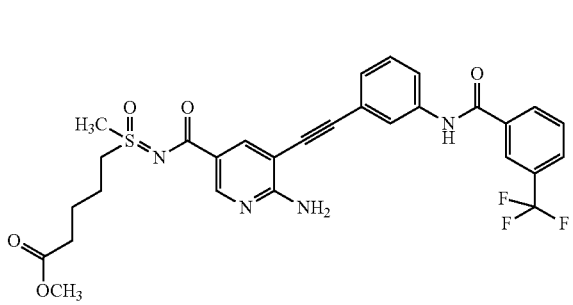

Methyl 5-[N-({6-amino-5-[(3-{[3-(trifluoromethyl)benzoyl]amino}phenyl)ethynyl]pyridin-3-yl}carbonyl)-S-methylsulfonimidoyl]pentanoate In a manner similar to that described in Example 25, methyl 5-[N-({6-amino-5-[(3-aminophenyl)ethynyl]pyridin-3-yl}carbonyl)-S-methylsulfonimidoyl]pentanoate and 3-(trifluoromethyl)benzoic acid were coupled to give the title compound as a white foam (78 mg).

¹H NMR (DMSO-d₆) δ: 10.56 (s, 1H), 8.57 (d, J=2.2 Hz, 1H), 8.32 (s, 1H), 8.28 (d, J=7.8 Hz, 1H), 8.06 (s, 1H), 8.05 (d, J=2.1 Hz, 1H), 7.99 (d, J=7.8 Hz, 1H), 7.81 (t, J=7.8 Hz, 1H), 7.78 (d, J=8.2 Hz, 1H), 7.46-7.49 (m, 1H), 7.42-7.45 (m, 1H), 7.01 (br. s., 2H), 3.53-3.64 (m, 5H), 3.41 (s, 3H), 2.40 (t, J=7.3 Hz, 2H), 1.75-1.87 (m, 2H), 1.66-1.73 (m, 2H)

Example 29

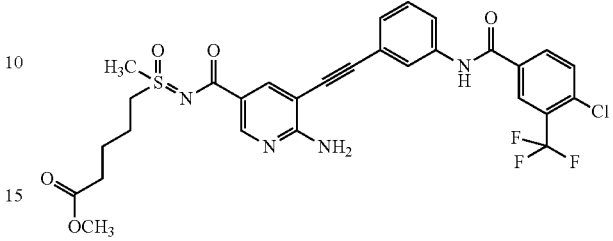

Methyl 5-[N-({6-amino-5-[(3-{[4-chloro-3-(trifluoromethyl)benzoyl]amino}phenyl)ethynyl]pyridin-3-yl}carbonyl)-S-methylsulfonimidoyl]pentanoate In a manner similar to that described in Example 25, methyl 5-[N-({6-amino-5-[(3-aminophenyl)ethynyl]pyridin-3-yl}carbonyl)-S-methylsulfonimidoyl]pentanoate and 4-chloro-3-(trifluoromethyl)benzoic acid were coupled to give the title compound as a white solid (74 mg).

¹H NMR (DMSO-d₆) δ: 10.61 (s, 1H), 8.57 (d, J=2.1 Hz, 1H), 8.41 (d, J=1.5 Hz, 1H), 8.28 (dd, J=8.4, 1.6 Hz, 1H), 8.03-8.06 (m, 2H), 7.95 (d, J=8.2 Hz, 1H), 7.76 (d, J=7.9 Hz, 1H), 7.47-7.49 (m, 1H), 7.42-7.45 (m, 1H), 7.01 (br. s., 2H), 3.53-3.64 (m, 5H), 3.40 (s, 3H), 2.40 (t, J=7.3 Hz, 2H), 1.75-1.87 (m, 2H), 1.69 (qd, J=7.4, 7.2 Hz, 2H)

Example 30

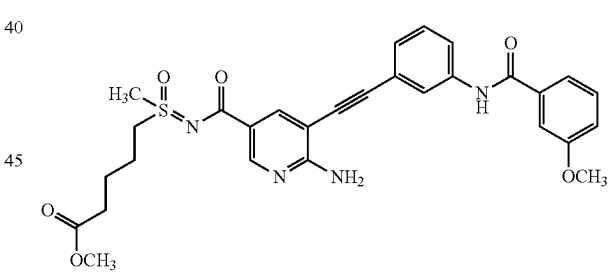

Methyl 5-(N-{[6-amino-5-({3-[(3-methoxybenzoyl)amino]phenyl}ethynyl)pyridin-3-yl]carbonyl}-S-methylsulfonimidoyl)pentanoate In a manner similar to that described in Example 25, methyl 5-[N-({6-amino-5-[(3-aminophenyl)ethynyl]pyridin-3-yl}carbonyl)-S-methylsulfonimidoyl]pentanoate and 3-methoxybenzoic acid were coupled to give the title compound as a white solid (75 mg).

¹H NMR (DMSO-d₆) δ: 10.30 (s, 1H), 8.57 (d, J=2.2 Hz, 1H), 8.03-8.07 (m, 2H), 7.77 (d, J=7.9 Hz, 1H), 7.55 (d, J=7.8 Hz, 1H), 7.50 (s, 1H), 7.46 (dd, J=15.1, 7.3 Hz, 2H), 7.39-7.42 (m, 1H), 7.18 (dd, J=8.1, 2.0 Hz, 1H), 7.00 (br. s., 2H), 3.85 (s, 3H), 3.53-3.64 (m, 5H), 3.40 (s, 3H), 2.40 (t, J=7.3 Hz, 2H), 1.75-1.86 (m, 2H), 1.66-1.72 (m, 2H)

Example 31

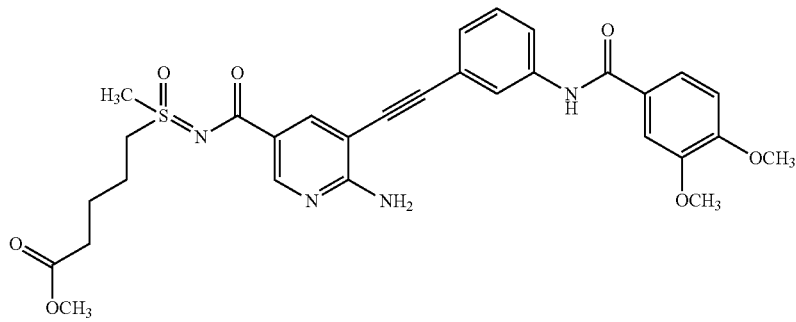 [SMILES: COC(=O)CCCCS(C)(=O)=NC(=O)c1cnc(N)c(C#Cc2cccc(NC(=O)c3ccc(OC)c(OC)c3)c2)c1]

Methyl 5-(N-{[6-amino-5-({3-[(3,4-dimethoxybenzoyl)amino]phenyl}ethynyl)pyridin-3-yl]carbonyl}-S-methylsulfonimidoyl)pentanoate In a manner similar to that described in Example 25, methyl 5-[N-({6-amino-5-[(3-aminophenyl)ethynyl]pyridin-3-yl}carbonyl)-S-methylsulfonimidoyl]pentanoate and 3,4-dimethoxybenzoic acid were coupled to give the title compound as a white foam (102 mg).

$^1$H NMR (DMSO-$d_6$) δ: 10.15 (s, 1H), 8.57 (d, J=2.3 Hz, 1H), 8.03-8.05 (m, 2H), 7.77 (ddd, J=7.8, 1.8, 1.6 Hz, 1H), 7.64 (dd, J=8.4, 1.9 Hz, 1H), 7.55 (d, J=1.8 Hz, 1H), 7.38-7.44 (m, 2H), 7.10 (d, J=8.5 Hz, 1H), 7.00 (br. s., 2H), 3.85 (s, 3H), 3.84 (s, 3H), 3.53-3.64 (m, 5H), 3.40 (s, 3H), 2.40 (t, J=7.3 Hz, 2H), 1.75-1.86 (m, 2H), 1.66-1.72 (m, 2H)

Preparation 40

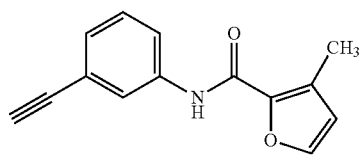 [SMILES: C#Cc1cccc(NC(=O)c2occc2C)c1]

3-Methyl-furan-2-carboxylic acid (3-ethynyl-phenyl)-amide

To the solution of 3-ethynylaniline (1.2 mL, 11.2 mmol, 1.0 eq) in anhydrous DMF (25 mL) was added 3-methyl-furan-2-carboxylic acid (1.84 g, 1.3 eq), diisopropylethyl amine (7.85 mL, 4.0 eq), and BOP (6.72 g, 1.35 eq). After the reaction solution was heated at 60° C. for two hours, it was cooled to room temperature, diluted with EtOAc, washed sequentially with aqueous NH$_4$Cl, water, brine, and lastly dried with anhydrous sodium sulfate. The clear solution was decanted, concentrated, and the yellow oily residue was subject to column chromatography (EtOAc-Hex from 1:100 to 1:10). The product eluting fractions were concentrated to give the title compound as a yellow oil.

Preparation 41

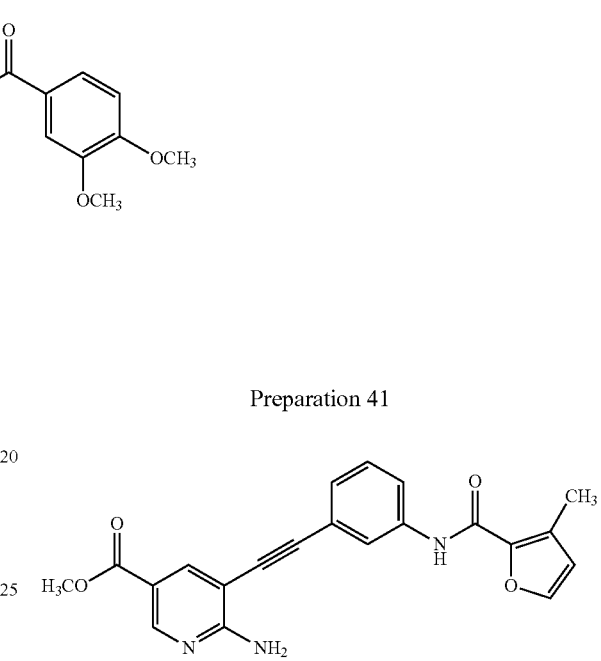

Methyl 6-amino-5-({3-[(3-methyl-2-furoyl)amino]phenyl}ethynyl)nicotinate

To the solution of 3-methyl-furan-2-carboxylic acid (3-ethynyl-phenyl)-amide (~1.3 eq) in anhydrous DMF (25 mL) was added 2-amino-3-iodo-5-nicotinic methyl ester (2.4 g, 8.63 mmol, 1 eq). The resulting solution was first degassed several times with dry nitrogen and then treated sequentially with triethylamine (4.82 mL, 4 eq), copper(I) iodide (329 mg, 0.2 eq), and bis(triphenylphosphine)palladium(II) dichloride (605 mg, 0.1 eq). The reaction mixture was stirred at RT for 10 minutes and then partitioned between saturated aq NaHCO$_3$ and CHCl$_3$. The organic layer was separated, washed with aq NH$_4$Cl (1×) and brine (1×), followed by drying with anhydrous Na$_2$SO$_4$. The upper clear liquid was decanted, concentrated, and the solid residue was treated with EtOAc-Hex (1:1). After the mixture was stirred at room temperature for 2 hours, it was filtered and the brown solid obtained was subject to a gradient column chromatography (from CHCl$_3$ to MeOH—CHCl$_3$ 1:20). The product containing fractions were concentrated to give the title compound as a white solid (1.82 g).

$^1$H NMR (DMSO-$d_6$) δ: 10.13 (s, 1H), 8.53 (d, J=2.3 Hz, 1H), 8.10 (t, J=1.7 Hz, 1H), 8.02 (d, J=2.2 Hz, 1H), 7.81 (d, J=1.5 Hz, 1H), 7.72-7.75 (m, 1H), 7.41-7.43 (m, 1H), 7.35-7.39 (m, 1H), 7.24 (br. s., 2H), 6.61 (d, J=1.5 Hz, 1H), 3.80 (s, 3H), 2.35 (s, 3H)

Preparation 42

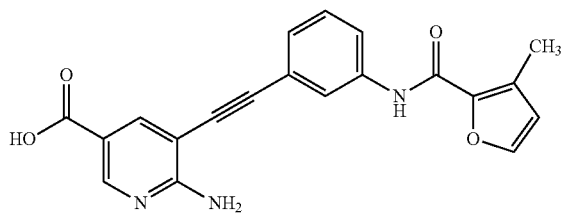 [SMILES: Cc1ccoc1C(=O)Nc1cccc(C#Cc2cc(C(=O)O)cnc2N)c1]

6-Amino-5-({3-[(3-methyl-2-furoyl)amino]phenyl}ethynyl)nicotinic acid

To a solution of methyl 6-amino-5-({3-[(3-methyl-2-furoyl)amino]phenyl}ethynyl)nicotinate, (1.82 g, 4.85 mmol, 1 eq) in MeOH—H₂O (100 mL, 3:1) at RT was added potassium hydroxide (2.72 g, 10 eq) with stirring. The mixture was heated at 65° C. for 2 hours and a brown solution was observed at this time. The reaction mixture was concentrated to remove most of the methanol. The resulting solution was cooled to 0° C. and concentrated HCl was added until the pH was around 3 at which time a white precipitates formed. The solid which had formed was collected by filtration, rinsed with water, and dried to give the title compound as a white solid (1.75 g).

¹H NMR (DMSO-d₆) δ: 12.62 (br. s., 1H), 10.13 (s, 1H), 8.51 (d, J=2.2 Hz, 1H), 8.09 (s, 1H), 7.99 (d, J=2.2 Hz, 1H), 7.81 (d, J=1.6 Hz, 1H), 7.74 (dt, J=7.7, 1.8 Hz, 1H), 7.33-7.44 (m, 2H), 7.13 (br. s., 2H), 6.60 (d, J=1.6 Hz, 1H), 2.35 (s, 3H)

Example 32

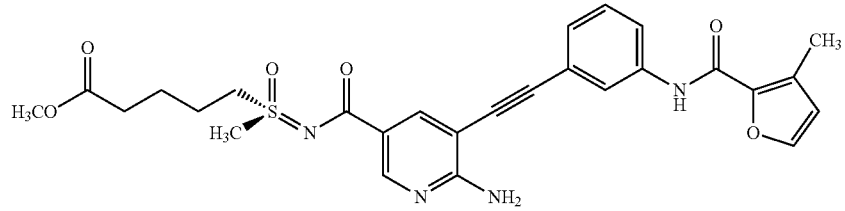 [SMILES: COC(=O)CCCC[S@](C)(=O)=NC(=O)c1cnc(N)c(C#Cc2cccc(NC(=O)c3occc3C)c2)c1]

(S)-Methyl 5-(N-{[6-amino-5-({3-[(3,4-dimethoxybenzoyl)amino]phenyl}ethynyl)pyridin-3-yl]carbonyl}-S-methylsulfonimidoyl)pentanoate To the solution of (S)-methyl 5-(S-methylsulfonimidoyl)pentanoate, (130 mg, 0.672 mmol, 1.2 eq) in anhydrous DMF (3 mL) was added 6-amino-5-({3-[(3-methyl-2-furoyl)amino]phenyl}ethynyl)nicotinic acid, (200 mg, 0.554 mmol, 1.0 eq), diisopropylethyl amine (0.2 mL, 2.0 eq), and BOP (270 mg, 1.1 eq). After the reaction solution was heated at 60° C. for three hours, it was cooled to room temperature, diluted with EtOAc, washed with aqueous NH₄Cl, water, brine, and lastly dried with anhydrous sodium sulfate. The clear solution was decanted, concentrated, and the brown oily residue was subject to column chromatography (EtOAc-Hex from 1:4 to 6:1). The corresponding product fractions were collected, concentrated under reduced pressure, and the residue was triturated with EtOAc-Hex (1:9). The solid which formed by scratching was collected by filtration and dried to give the title compound as a white solid (155 mg).

¹H NMR (DMSO-d₆) δ: 10.13 (s, 1H), 8.57 (d, J=2.2 Hz, 1H), 8.08 (t, J=1.6 Hz, 1H), 8.04 (d, J=2.2 Hz, 1H), 7.81 (d, J=1.6 Hz, 1H), 7.74 (dt, J=7.7, 1.8 Hz, 1H), 7.33-7.44 (m, 2H), 6.98 (br. s., 2H), 6.60 (d, J=1.6 Hz, 1H), 3.49-3.68 (m, 5H), 3.41 (s, 3H), 2.40 (t, J=7.2 Hz, 2H), 2.35 (s, 3H), 1.62-1.89 (m, 4H)

Example 33

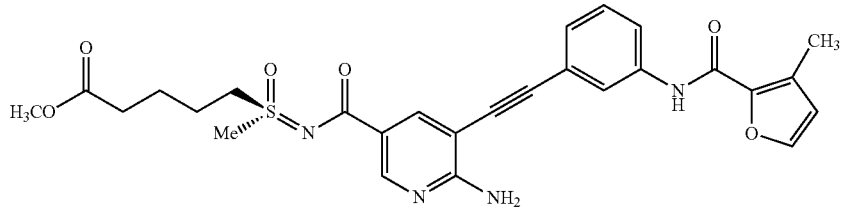 [SMILES: COC(=O)CCCC[S@@](C)(=O)=NC(=O)c1cnc(N)c(C#Cc2cccc(NC(=O)c3occc3C)c2)c1]

(R)-Methyl 5-(N-{[6-amino-5-({3-[(3-methyl-2-furoyl)amino]phenyl}ethynyl)pyridin-3-yl]carbonyl}-S-methylsulfonimidoyl)pentanoate In a manner similar to that described in Example 32, (R)-methyl 5-(S-methylsulfonimidoyl)pentanoate and 6-amino-5-({3-[(3-methyl-2-furoyl)amino]phenyl}ethynyl)nicotinic acid, were reacted to give the title compound.

¹H NMR (DMSO-d₆) δ: 10.13 (s, 1H), 8.57 (d, J=2.2 Hz, 1H), 8.08 (t, J=1.6 Hz, 1H), 8.04 (d, J=2.2 Hz, 1H), 7.81 (d, J=1.6 Hz, 1H), 7.74 (dt, J=7.7, 1.8 Hz, 1H), 7.33-7.44 (m, 2H), 6.98 (br. s., 2H), 6.60 (d, J=1.6 Hz, 1H), 3.49-3.68 (m, 5H), 3.41 (s, 3H), 2.40 (t, J=7.2 Hz, 2H), 2.35 (s, 3H), 1.62-1.89 (m, 4H)

Preparation 43

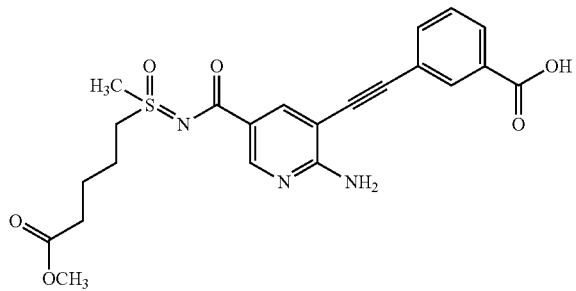 [SMILES: COC(=O)CCCCS(C)(=O)=NC(=O)c1cnc(N)c(C#Cc2cccc(C(=O)O)c2)c1]

3-{[2-Amino-5-({[(5-methoxy-5-oxopentyl)(methyl) oxido-λ⁴-sulfanylidene]amino}carbonyl)pyridin-3-yl]ethynyl}benzoic acid To the nitrogen degassed solution of methyl 5-{N-[(6-amino-5-iodopyridin-3-yl)carbonyl]-S-methylsulfonimidoyl}pentanoate, (1.119 g, 1.0 eq) and 3-ethynylbenzoic acid (0.47 g, 1.2 eq) in anhydrous DMF (10 mL) was added triethylamine (1.42 mL, 4 eq), copper(I) iodide (97 mg, 0.2 eq), and bis(triphenylphosphine)palladium(II) dichloride (179 mg, 0.1 eq). The reaction mixture was stirred at RT for 30 minutes and then partitioned between i-PrOH—CHCl₃ (1:5) and aq NH₄Cl. The pH of the aqueous layer was adjusted to 3 using 10% aq KHSO₄. The aqueous layer was isolated and extracted once more with i-PrOH—CHCl₃ (1:5). All organic layers were combined, washed with brine, and dried with anhydrous Na₂SO₄. The organic phase was decanted, concentrated, and the brown oily residue was subject to a gradient column chromatography [from CHCl₃ to MeOH—CHCl₃ (1:9)]. The product containing fractions were collected, concentrated, and the solid residue was triturated with i-PrOH. The solid which formed was collected by filtration to give the title compound as a lightly yellow solid (853 mg).

¹H NMR (DMSO-d₆) δ: 13.19 (br. s., 1H), 8.57 (br. s., 1H), 8.26 (s, 1H), 8.07 (d, J=2.1 Hz, 1H), 7.92 (dd, J=11.5, 8.0 Hz, 2H), 7.51-7.59 (m, 1H), 7.10 (br. s., 2H), 3.49-3.68 (m, 5H), 3.40 (s, 3H), 2.40 (t, J=7.1 Hz, 2H), 1.61-1.90 (m, 4H)

Example 34

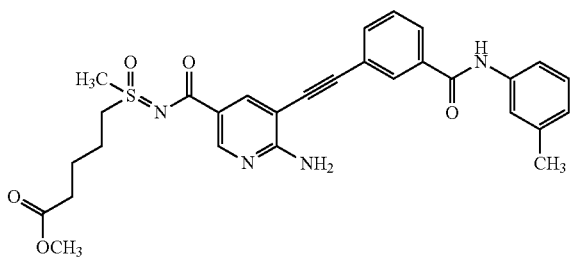 [SMILES: COC(=O)CCCCS(C)(=O)=NC(=O)c1cnc(N)c(C#Cc2cccc(C(=O)Nc3cccc(C)c3)c2)c1]

Methyl 5-[N-({6-amino-5-[(3-{[(3-methylphenyl) amino]carbonyl}phenyl)ethynyl]pyridin-3-yl}carbonyl)-S-methylsulfonimidoyl]pentanoate To the mixture of 3-{[2-amino-5-({[(5-methoxy-5-oxopentyl)(methyl)oxido-λ⁴-sulfanylidene]amino}carbonyl)pyridin-3-yl]ethynyl}benzoic acid (80 mg, 0.175 mmol, 1 eq) and m-toluidine (37.4 mg, 2.0 eq) in dichloroethane (1.5 mL) at 50° C. was added catalytic amount of DMAP (4.3 mg, 0.2 eq) and EDCI (40.3 mg, 1.2 eq). The reaction was stirred at that temperature for 3 h. It was then partitioned between EtOAc and saturated aq NaHCO₃. The organic layer was further washed with aq NH₄Cl, brine and then dried with anhydrous sodium sulfate. The organic solution was decanted, concentrated, and the residue was subject to a gradient column chromatography (EtOAc-Hex 1:7 to neat EtOAc). Concentration of the product containing fractions gave the title compound as a white foam after dried in vacuo (72 mg).

¹H NMR (DMSO-d₆) δ: 10.25 (s, 1H), 8.58 (d, J=2.3 Hz, 1H), 8.26 (t, J=1.5 Hz, 1H), 8.08 (d, J=2.3 Hz, 1H), 7.93 (dt, J=7.9, 1.3 Hz, 1H), 7.89 (dt, J=7.7, 1.2 Hz, 1H), 7.63 (s, 1H), 7.56-7.60 (m, 2H), 7.24 (t, J=7.8 Hz, 1H), 7.09 (br. s., 2H), 6.94 (d, J=7.6 Hz, 1H), 3.54-3.64 (m, 5H), 3.41 (s, 3H), 2.40 (t, J=7.3 Hz, 2H), 2.32 (s, 3H), 1.75-1.87 (m, 2H), 1.66-1.72 (m, 2H)

Example 35

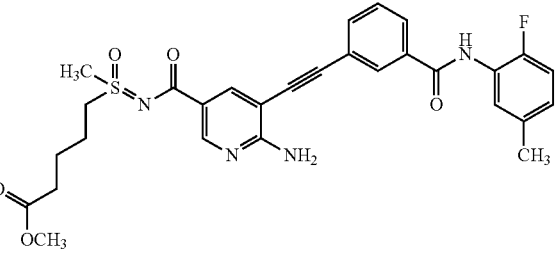

Methyl 5-[N-({6-amino-5-[(3-{[(2-fluoro-5-methylphenyl)amino]carbonyl}phenyl)ethynyl]pyridin-3-yl}carbonyl)-S-methylsulfonimidoyl]pentanoate In a manner similar to that described in Example 34, 3-{[2-amino-5-({[(5-methoxy-5-oxopentyl)(methyl)oxido-λ⁴-sulfanylidene]amino}carbonyl)pyridin-3-yl]ethynyl}benzoic acid and 2-fluoro-5-methylaniline were reacted to give the title compound as a clear oil (89 mg).

¹H NMR (DMSO-d₆) δ: 10.14 (s, 1H), 8.58 (d, J=2.2 Hz, 1H), 8.27 (t, J=1.6 Hz, 1H), 8.07 (d, J=2.2 Hz, 1H), 7.95 (dt, J=7.8, 1.4 Hz, 1H), 7.90 (dt, J=7.7, 1.3 Hz, 1H), 7.58 (t, J=7.7 Hz, 1H), 7.41 (dd, J=7.3, 1.6 Hz, 1H), 7.18 (dd, J=10.3, 8.4 Hz, 1H), 7.04-7.13 (m, 3H), 3.53-3.64 (m, 5H), 3.40 (s, 3H), 2.40 (t, J=7.3 Hz, 2H), 2.31 (s, 3H), 1.75-1.86 (m, 2H), 1.66-1.72 (m, 2H)

Example 36

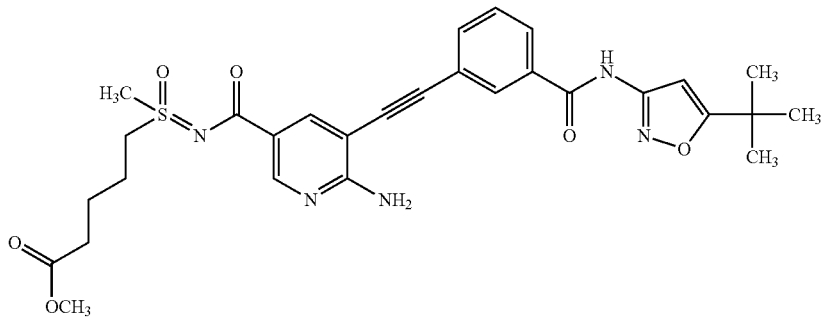 [SMILES: COC(=O)CCCCS(C)(=O)=NC(=O)c1cnc(N)c(C#Cc2cccc(C(=O)Nc3cc(C(C)(C)C)on3)c2)c1]

Methyl 5-[N-({6-amino-5-[(3-{[(5-tert-butylisox-azol-3-yl)amino]carbonyl}phenyl)ethynyl]pyridin-3-yl}carbonyl)-S-methylsulfonimidoyl]pentanoate In a manner similar to that described in Example 34, 3-{[2-amino-5-({[(5-methoxy-5-oxopentyl)(methyl)oxido-λ⁴-sulfanylidene]amino}carbonyl)pyridin-3-yl]ethynyl}benzoic acid and 5-(tert-butyl)isoxazol-3-amine were reacted to give the title compound as a clear oil (70 mg).

¹H NMR (DMSO-d₆) δ: 11.40 (s, 1H), 8.58 (d, J=2.3 Hz, 1H), 8.31 (t, J=1.5 Hz, 1H), 8.07 (d, J=2.2 Hz, 1H), 7.99 (dt, J=7.8, 1.4 Hz, 1H), 7.91 (dt, J=7.7, 1.1 Hz, 1H), 7.57 (t, J=7.8 Hz, 1H), 7.08 (br. s., 2H), 6.73 (s, 1H), 3.53-3.64 (m, 5H), 3.41 (s, 3H), 2.40 (t, J=7.3 Hz, 2H), 1.75-1.86 (m, 2H), 1.65-1.73 (m, 2H), 1.33 (s, 9H)

Example 37

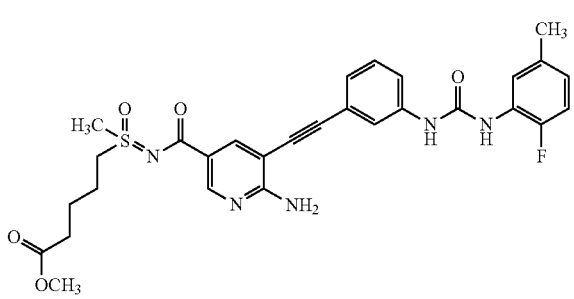 [SMILES: COC(=O)CCCCS(C)(=O)=NC(=O)c1cnc(N)c(C#Cc2cccc(NC(=O)Nc3cc(C)ccc3F)c2)c1]

Methyl 5-{N-[(6-amino-5-{[3-({[(2-fluoro-5-methylphenyl)amino]carbonyl}amino)phenyl]ethynyl}pyridin-3-yl)carbonyl]-S-methylsulfonimidoyl}pentanoate A solution of methyl 5-[N-({6-amino-5-[(3-aminophenyl)ethynyl]pyridin-3-yl}carbonyl)-S-methylsulfonimidoyl]pentanoate (85.6 mg, 0.2 mmol, 1 eq) and 2-fluoro-5-methylphenyl isocyanate (29 μL, 1.1 eq) in anhydrous DMF (2 mL) was stirred at room temperature overnight. The reaction was then diluted with EtOAc, washed sequentially with aq NH₄Cl, saturated aq NaHCO₃, brine, and lastly dried with sodium sulfate. The clear solution was decanted, concentrated, and the oily residue was subject to a gradient column chromatography (EtOAc-Hex from 1:1 to neat EtOAc). The product containing fractions were concentrated to give the title compound as a white foam (86.2 mg).

¹H NMR (DMSO-d₆) δ: 9.14 (s, 1H), 8.56 (d, J=2.2 Hz, 1H), 8.54 (d, J=2.2 Hz, 1H), 8.05 (d, J=2.2 Hz, 1H), 7.99 (dd, J=7.8, 1.5 Hz, 1H), 7.81 (s, 1H), 7.38-7.40 (m, 1H), 7.30-7.35 (m, 2H), 7.11 (dd, J=11.3, 8.4 Hz, 1H), 6.99 (br. s., 2H), 6.79-6.83 (m, 1H), 3.53-3.64 (m, 5H), 3.41 (s, 3H), 2.40 (t, J=7.3 Hz, 2H), 2.27 (s, 3H), 1.75-1.87 (m, 2H), 1.65-1.73 (m, 2H)

Example 38

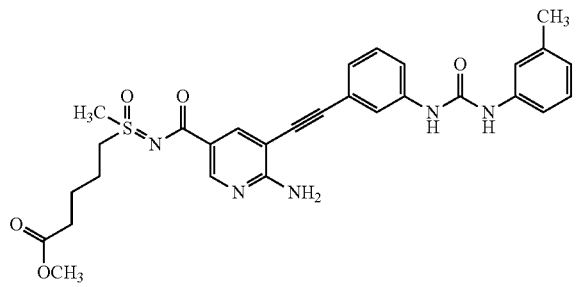 [SMILES: COC(=O)CCCCS(C)(=O)=NC(=O)c1cnc(N)c(C#Cc2cccc(NC(=O)Nc3cccc(C)c3)c2)c1]

Methyl 5-{N-[(6-amino-5-{[3-({[(3-methylphenyl)amino]carbonyl}amino)phenyl]ethynyl}pyridin-3-yl)carbonyl]-S-methylsulfonimidoyl}pentanoate In a manner similar to that describe in Example 37, methyl 5-[N-({6-amino-5-[(3-aminophenyl)ethynyl]pyridin-3-yl}carbonyl)-S-methylsulfonimidoyl]pentanoate and 5-methylphenyl isocyanate were coupled. Purification of the crude reaction product gave the title compound as a white foam (78.8 mg).

¹H NMR (DMSO-d₆) δ: 8.74 (br. s., 1H), 8.66 (br. s., 1H), 8.56 (d, J=2.2 Hz, 1H), 8.04 (d, J=2.1 Hz, 1H), 7.78 (s, 1H), 7.41 (dt, J=7.8, 1.7 Hz, 1H), 7.28-7.34 (m, 3H), 7.23 (d, J=8.1 Hz, 1H), 7.16 (t, J=7.7 Hz, 1H), 6.98 (br. s., 2H), 6.80 (d, J=7.3 Hz, 1H), 3.53-3.64 (m, 5H), 3.40 (s, 3H), 2.40 (t, J=7.3 Hz, 2H), 2.28 (s, 3H), 1.75-1.86 (m, 2H), 1.66-1.73 (m, 2H)

Preparation 44

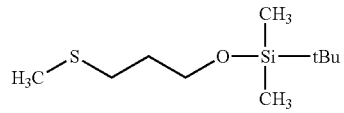

tert-Butyldimethyl(3-(methylthio)propoxy)silane

A solution of 3-(methylthiol)-1-propanol (10.52 mL, 0.1 mol, 1.0 eq) in anhydrous DMF (50 mL) was added tert-butyldimethylsilyl chloride (25 g, 1.6 eq) and imidazole (27.5 g, 4.0 eq). The resulting reaction solution was stirred at room temperature for 1 hour. It was then diluted with EtOAc, followed by a sequential wash with water (2×) and brine (1×), and was lastly dried with anhydrous sodium sulfate. The supernatant liquid was decanted, concentrated, and the oily residue was subject to column chromatography (from neat hexanes to EtOAc-hex 1:50). The compound containing fractions were concentrated to give the title compound as a clear oil in quantitative yield.

Preparation 45

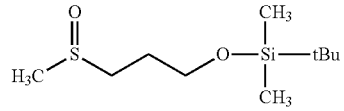

tert-Butyldimethyl(3-(methylsulfinyl)propoxy)silane

A solution of tert-butyldimethyl(3-(methylthio)propoxy)silane (0.1 mol) in water/MeOH (3:2, 500 mL) at 0° C. was added sodium (meta)periodate (~30 g). The reaction mixture was stirred first at 0° C. for 20 hours, then at room temperature for 3 hours. The reaction mixture was then filtered and the filtrate was concentrated under reduced pressure to remove the most of the organic solvent. The aqueous residue was then extracted with CHCl₃ (2×) and the combined organic extracts were dried with anhydrous sodium sulfate. The organic phase was decanted and concentrated to yield the title compound as an oil which solidified to provide a white solid upon standing (17.65 g).

Preparation 46

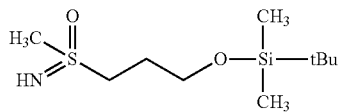

tert-Butyldimethyl(3-(S-methylsulfonimidoyl)propoxy)silane

To a 1-L round-bottom flask containing 2,2,2-trifluoroacetamide (17.43 g), magnesium oxide (12.1 g), and rhodium (II) acetate (0.99 g) in anhydrous dichloromethane (500 mL) was added tert-butyldimethyl(3-(methylsulfinyl)propoxy)silane (17.65 g) and (diacetoxyiodo)benzene (36.1 g). The resulting reaction mixture was stirred at room temperature for 24 hours and then filtered through a short pad of celite. The filtrate was concentrated, the brown oily residue was taken up in MeOH (~500 mL), and potassium carbonate (51.7 g) was added. The reaction mixture was stirred at RT for 2 hours. The mixture was then filtered through a pad of celite, the pad was washed with MeOH, and the filtrate was concentrated. The resulting soft brown solid was treated with DCM-EtOAc (4:1), the mixture was stirred at room temperature for 1 hour, and it was filtered again through a pad composed of silica gel and celite. The pad was washed with DCM-EtOAc (2:1) first and then with neat EtOAc only. The filtrate was concentrated and the brown oily residue was subject to a column chromatography (EtOAc-Hex 1:2 to neat EtOAc). Concentration of the product eluting fractions gave the title compound as a light brown oil (12.3 g).

Preparation 47

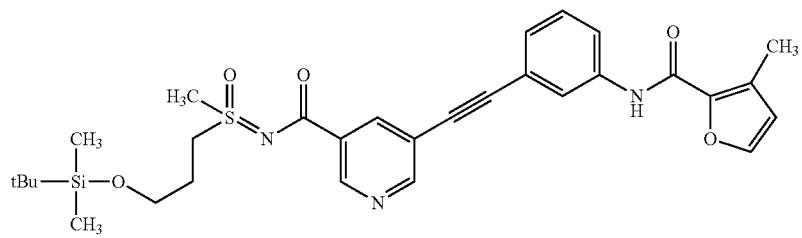 [SMILES: Cc1ccoc1C(=O)Nc1cccc(C#Cc2cncc(C(=O)N=S(C)(=O)CCCO[Si](C)(C)C(C)(C)C)c2)c1]

N-[(3-{[tert-Butyl(dimethyl)silyl]oxy}propyl)(methyl)oxido-$\lambda^4$-sulfanylidene]-5-({3-[(3-methyl-2-furoyl)amino]phenyl}ethynyl)nicotinamide To a solution of tert-butyldimethyl(3-(S-methylsulfonimidoyl)propoxy)silane (1.07 g, 4.25 mmol, 1 eq) in anhydrous DMF (8 mL) under nitrogen atmosphere was added 5-{3-[(3-methyl-furan-2-carbonyl)-amino]-phenylethynyl}-nicotinic acid (1.54 g, 1.05 eq), diisopropylethylamine (1.50 mL, 2.0 eq), and BOP (2.13 g, 1.1 eq). The reaction mixture was stirred at room temperature for 2 hours and then diluted with EtOAc. It was washed sequentially with aqueous NH₄Cl (2×), saturated aqueous NaHCO₃ (1×), and brine (1×). At last it was dried with anhydrous Na₂SO₄. The supernatant liquid was decanted, concentrated, and the oily residue was subject to column chromatography (EtOAc-Hex 1:4 to 1:2). Concentration of the product eluting fractions gave the title compound as a white foam (2.05 g).

Example 39

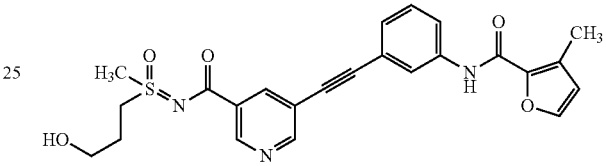

N-[(3-Hydroxypropyl)(methyl)oxido-$\lambda^4$-sulfanylidene]-5-({3-[(3-methyl-2-furoyl)amino]phenyl}ethynyl)nicotinamide To a solution of N-[(3-{[tert-butyl(dimethyl)silyl]oxy}propyl)(methyl)oxido-$\lambda^4$-sulfanylidene]-5-({3-[(3-methyl-2-furoyl)amino]phenyl}ethynyl)nicotinamide, (2.05 g) in anhydrous THF (70 mL) at 0° C. was added dropwise tetrabutylammonium fluoride (8.92 mL, 2.1 eq). After the reaction was further stirred at 0° C. for about 2 hours, it was concentrated at room temperature under reduced pressure and then partitioned between EtOAc and saturated aqueous NaHCO3. The organic layer was isolated, washed with aqueous NH₄Cl and brine, and dried with anhydrous sodium sulfate. The clear solution was decanted, concentrated, and the oily residue was subject to a gradient column chromatography (EtOAc-Hex 1:1 to 10:1). Concentration of the product eluting fractions gave the title compound as a white foam (1.34 g).

¹H NMR (DMSO-d₆) δ: 10.20 (s, 1H), 9.09 (d, J=2.1 Hz, 1H), 8.92 (d, J=2.1 Hz, 1H), 8.38 (t, J=2.1 Hz, 1H), 8.12 (t, J=1.8 Hz, 1H), 7.82 (d, J=1.6 Hz, 1H), 7.79-7.81 (m, 1H), 7.39-7.43 (m, 1H), 7.34 (dt, J=7.6, 1.2 Hz, 1H), 6.61 (d, J=1.6 Hz, 1H), 4.77 (t, J=5.3 Hz, 1H), 3.61-3.72 (m, 2H), 3.55 (q, J=5.9 Hz, 2H), 3.51 (s, 3H), 2.35 (s, 3H), 1.92-2.02 (m, 2H)

Preparation 48

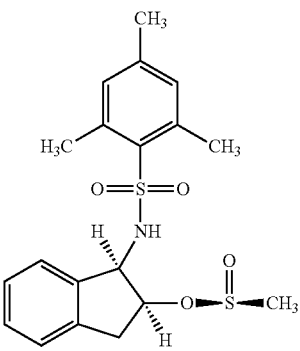 [SMILES: Cc1cc(C)c(S(=O)(=O)N[C@@H]2c3ccccc3C[C@@H]2O[S@](C)=O)c(C)c1]

[S(R)]-(1R,2S)-1-(2,4,6-Trimethylphenylsulfonamido)-2,3-dihydro-1H-inden-2-yl methanesulfinate The reagent (2S,3aR,8aS)-3-(mesitylsulfonyl)-3,3a,8,8a-tetrahydroindeno[1,2-d][1,2,3]oxathiazole 2-oxide (3.9 g, 10.3 mmol) was prepared by the method described by Han, Z. et al Tetrahedron 61 (2005) 6386-6408. To a solution of (2S,3aR,8aS)-3-(mesitylsulfonyl)-3,3a,8,8a-tetrahydroindeno[1,2-d][1,2,3]oxathiazole 2-oxide (3.9 g, 10.3 mmol) in THF (40 mL) was cooled to −78° C. and treated with MeMgBr (3.0M in ether, 4.1 mL, 12.4 mmol) slowly. The reaction mixture was stirred at −78° C. for 1 h, and quenched with saturated NaHCO3 (30 mL). The organic phase was separated and the aqueous phase was extracted with EtOAc (2×40 mL). The combined organic phase was washed with brine (40 mL), dried over Na2SO4, concentrated, and purified by chromatography (EtOAc/hexanes). Concentration of the product eluting fractions gave the thitle compound (2.7 g, 67%).

Preparation 49

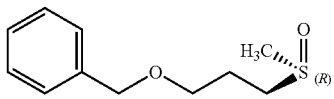

(R)-((3-(Methylsulfinyl)propoxy)methyl)benzene

A solution of [S(R)]-(1R,2S)-1-(2,4,6-trimethylphenylsulfonamido)-2,3-dihydro-1H-inden-2-yl methanesulfinate (2.7 g, 6.86 mmol) in THF (30 mL) was cooled to −78° C. and then treated with 3-(benzyloxy)propylmagnesium bromide (20 mL, 0.41M, 8.19 mmol) slowly. The reaction mixture was stirred at −78° C. for 1 h, warmed to −10° C. during 20 min, and quenched with saturated NaHCO3 (30 mL). The organic phase was separated and the aqueous phase was extracted with EtOAc (2×50 mL). The combined organic phase was washed with brine, dried over Na2SO4, concentrated, and purified by chromatography (EtOAc/hexanes). Concentration of the product eluting fractions gave the title compound (0.92 g, 63.7%, 69.7% ee).

Preparation 50

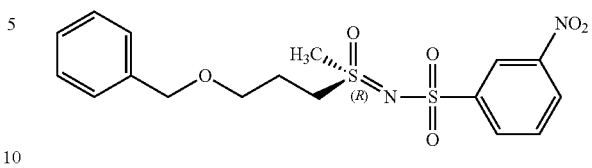

(R)-{[3-(S-Methylsulfonimidoyl)propoxy]methyl}benzene nosylate

To a mixture of (R)-((3-(methylsulfinyl)propoxy)methyl)benzene (0.50 g, 2.36 mmol, 1 eq.) was dissolved in DCM (15 mL) followed by addition of NsNH2 (0.71 g, 3.53 mmol, 1.5 eq.) and PhIO (0.77 g, 03.53 mol, 1.5 eq.). The reaction mixture was stirred at room temperature for 10 min followed by addition of Rh2(OAc)4 (30 mg, 0.07 mmol, 0.03 eq.), stirred for 1.5 hours, and filtered. The filtered cake was slurried with DCM (30 mL). The combined DCM was concentrated to give an oil product that was reslurried with hexane to give a crude product (0.26 g) that was recrystallized from MeOH/DCM to furnish the title compound (0.148 g, 15%, 98% ee).

Preparation 51

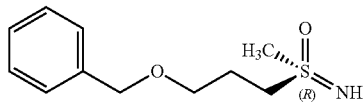

(R)-{[3-(S-Methylsulfonimidoyl)propoxy]methyl}benzene

A mixture of (R)-{[3-(S-methylsulfonimidoyl)propoxy]methyl}benzene nosylate (0.51 g, 1.24 mmol), PhSH (0.22 g, 1.98 mmol) and Cs2CO3 (0.73 g, 2.23 mmol) in CH3CN (10 mL) was stirred at 46° C. overnight, filtered, concentrated, and purified by chromatography (EtOAc/MeOH) to give the title compound (0.26 g, >99% ee).
$^1$H NMR (600 MHz, DMSO-$d_6$) d=7.37-7.34 (m, 2H, o), 7.34-7.31 (m, 2H, o), 7.31-7.27 (m, 1H), 4.47 (s, 2H), 3.62 (s, 1H), 3.53 (t, J=6.3 Hz, 2H), 3.08 (dd, J=7.5, 8.5 Hz, 2H), 2.88 (s, 3H), 2.03-1.91 (m, 2H)

Preparation 52

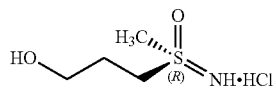

(R)-3-(S-Methylsulfonimidoyl)propan-1-ol

To a 50 mL round-bottom flask placed with (R)-{[3-(S-methylsulfonimidoyl)propoxy]methyl}benzene (459.23 mg, 2 mmol, 1 eq), EtOH (10 mL), Pd/C (10 wt. %, 92 mg, 0.3 eq),

Example 40

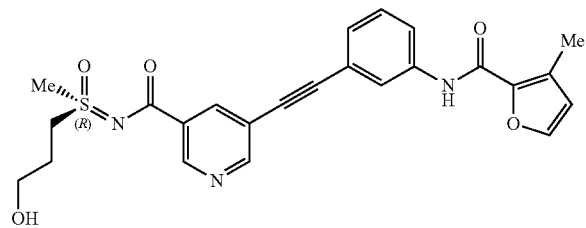

(R)—N-[(3-Hydroxypropyl)(methyl)oxido-λ⁴-sulfanylidene]-5-({3-[(3-methyl-2-furoyl)amino]phenyl}ethynyl)nicotinamide To the solution of 5-{3-[(3-methyl-furan-2-carbonyl)-amino]-phenylethynyl}-nicotinic acid (173 mg, 0.5 mmol, 1 eq), (R)-3-(S-methylsulfonimidoyl)propan-1-ol (200 mg, 2.3 eq), and diisopropylethylamine (0.26 mL, 3 eq) in anhydrous DMF (3 mL) was added BOP (251 mg, 1.1 eq). After the reaction was stirred at room temperature for 15 minutes, it was partitioned between ethyl acetate and aqueous ammonium chloride. The organic layer was isolated, washed with saturated aqueous sodium bicarbonate, brine, and dried with anhydrous sodium sulfate. The upper liquor was decanted, concentrated, and the oily residue was subject to a gradient column chromatography. Concentration of the product eluting fractions gave the title compound as a white foam (162.7 mg).

$^1$H NMR (DMSO-d$_6$) δ: 10.20 (s, 1H), 9.09 (d, J=1.8 Hz, 1H), 8.92 (d, J=2.1 Hz, 1H), 8.38 (t, J=2.1 Hz, 1H), 8.12 (t, J=1.8 Hz, 1H), 7.82 (d, J=1.5 Hz, 1H), 7.79-7.81 (m, 1H), 7.39-7.43 (m, 1H), 7.34 (dt, J=7.6, 1.2 Hz, 1H), 6.61 (d, J=1.2 Hz, 1H), 4.77 (t, J=5.3 Hz, 1H), 3.60-3.72 (m, 2H), 3.55 (q, J=5.9 Hz, 2H), 3.51 (s, 3H), 2.35 (s, 3H), 1.92-2.02 (m, 2H)

Preparation 53

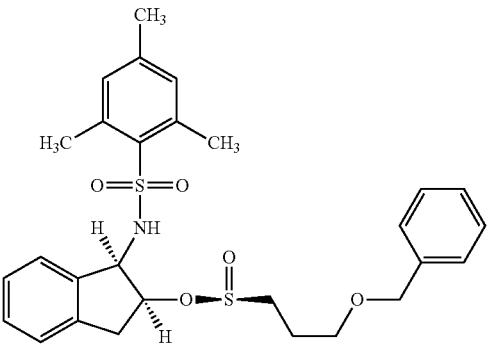 [SMILES: Cc1cc(C)c(S(=O)(=O)N[C@@H]2c3ccccc3C[C@@H]2O[S@@](=O)CCCOCc2ccccc2)c(C)c1]

[S(R)]-(1R,2S)-1-(2,4,6-Trimethylphenylsulfonamido)-2,3-dihydro-1H-inden-2-yl 3-(benzyloxy)propane-1-sulfinate The reagent (2S,3 aR,8aS)-3-(mesitylsulfonyl)-3,3a,8,8a-tetrahydroindeno[1,2-d][1,2,3]oxathiazole 2-oxide (3.9 g, 10.3 mmol) was prepared by the method described by Han, Z. et al Tetrahedron 61 (2005) 6386-6408. To a solution of (2S,3aR,8aS)-3-(mesitylsulfonyl)-3,3a,8,8a-tetrahydroindeno[1,2-d][1,2,3]oxathiazole 2-oxide (3.79 g, 10.3 mmol) in THF (40 mL) was at −78° C. added 3-(benzyloxy)propylmagnesium bromide (30 ml, 0.41M, 12.4 mmol, 1.2 eq) slowly. The reaction mixture was stirred at −70° C. for 1 h, and quenched with saturated NaHCO3 (30 mL), diluted with EtOAc (3×50 mL). The organic phase was separated, washed with sat. aq. NaCl (40 mL), dried over Na$_2$SO$_4$, concentrated, and purified by chromatography (EtOAc/hexanes) to give a the title compound (3.0 g, 55.1%).

Preparation 54

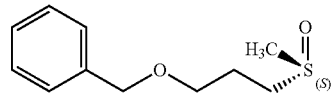

(S)-((3-(Methylsulfinyl)propoxy)methyl)benzene

To a solution of [S(R)]-(1R,2S)-1-(2,4,6-trimethylphenylsulfonamido)-2,3-dihydro-1H-inden-2-yl 3-(benzyloxy)propane-1-sulfinate (3.0 g, 5.69 mmol) in THF (30 mL) was added at −78° C. MeMgBr (3.0 M in ether, 2.85 ml, 8.55 mmol) solution slowly. The reaction mixture was stirred at −78° C. for 1 h, quenched with saturated NaHCO$_3$ (30 mL). The organic phase was separated and the aqueous phase was extracted with EtOAc (2×40 mL). The combined organic phase was washed with brine, dried over Na$_2$SO$_4$, concentrated, and purified by chromatography (EtOAc/hexanes). Concentration of the product eluting fractions gave the title compound (1.09 g, 90%, 87.4% ee).

Preparation 55

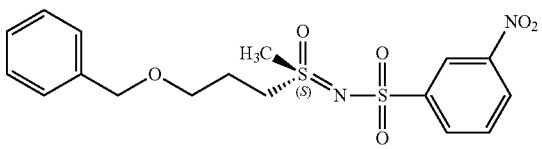

(S)-((3-(S-Methylsulfonimidoyl)propoxy)methyl)benzene nosylate

To a solution of (S)-((3-(methylsulfinyl)propoxy)methyl)benzene (0.5 g, 2.36 mmol, 1 eq.) was dissolved in DCM (1.5 L) followed by addition of $NsNH_2$ (0.71 g, 3.53 mmol, 1.5 eq.) and PhIO (0.77 g, 03.53 mol, 1.5 eq.). The reaction mixture was stirred at room temperature for 10 min followed by addition of $Rh_2(OAc)_4$ (30 mg, 0.07 mmol, 0.03 eq.), stirred for 1.5 hours, and filtered. The filtered cake was slurried with DCM (30 mL). The combined DCM was concentrated to give an oil product that was reslurried with hexane to give the crude title compound (0.26 g) that was recrystallized from MeOH/DCM to furnish the title compound (0.141 g, 15%, 97.78% ee).

Preparation 56

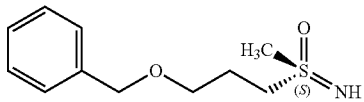

(S)-((3-(S-Methylsulfonimidoyl)propoxy)methyl)benzene

A mixture of (S)-((3-(S-methylsulfonimidoyl)propoxy)methyl)benzene nosylate (0.45 g, 1.09 mmol) and $Cs_2CO_3$ (0.64 g, 1.96 mmol) in $CH_3CN$ (10 mL) was stirred at 46° C. overnight, filtered, concentrated, and purified by chromatography (EtOAc/MeOH) to furnish the title compound (0.25 g, >99% ee).

$^1$H NMR (600 MHz, DMSO-$d_6$) δ=7.37-7.34 (m, 2H, o), 7.35-7.32 (m, 2H, o), 7.31-7.27 (m, 1H), 4.47 (s, 2H), 3.63 (s, 1H), 3.53 (t, J=6.3 Hz, 2H), 3.09 (dd, J=7.5, 8.5 Hz, 2H), 2.88 (s, 3H), 2.02-1.93 (m, 2H)

Preparation 57

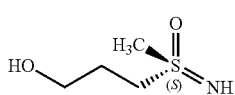

(S)-3-(S-Methylsulfonimidoyl)propan-1-ol

In a manner similar to that described in Preparation 52, (S)-((3-(S-methylsulfonimidoyl)propoxy)methyl)benzene is converted to the title compound.

Example 41

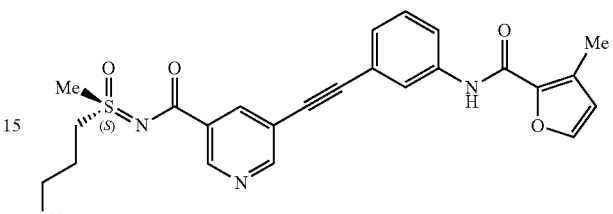

(S)—N-[(3-Hydroxypropyl)(methyl)oxido-λ$^4$-sulfanylidene]-5-({3-[(3-methyl-2-furoyl)amino]phenyl}ethynyl)nicotinamide In a manner similar to the procedure described in Example 40, 5-{3-[(3-methyl-furan-2-carbonyl)-amino]-phenylethynyl}-nicotinic acid and (S)-3-(S-methylsulfonimidoyl)propan-1-ol were converted to the title compound.

$^1$H NMR (600 MHz, DMSO-$d_6$) δ=10.20 (s, 1H), 9.09 (d, J=2.0 Hz, 1H), 8.92 (d, J=2.1 Hz, 1H), 8.38 (t, J=2.1 Hz, 1H), 8.12 (t, J=1.7 Hz, 1H), 7.81 (d, J=1.7 Hz, 1H), 7.81-7.79 (m, 1H), 7.43-7.39 (m, 1H), 7.34 (td, J=1.3, 7.7 Hz, 1H), 6.61 (d, J=1.6 Hz, 1H), 4.78 (t, J=5.3 Hz, 1H), 3.73-3.60 (m, 2H), 3.55 (q, J=6.0 Hz, 2H), 3.51 (s, 3H), 2.35 (s, 3H), 2.04-1.91 (m, 2H)

Example 42

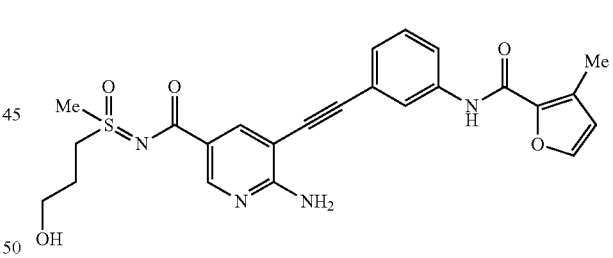

6-Amino-N-[(3-hydroxypropyl)(methyl)oxido-λ$^4$-sulfanylidene]-5-({3-[(3-methyl-2-furoyl)amino]phenyl}ethynyl)nicotinamide In a manner similar to the procedure described in Example 40, 6-amino-5-{3-[(3-methyl-furan-2-carbonyl)-amino]-phenylethynyl}-nicotinic acid and 3-(S-methylsulfonimidoyl)propan-1-ol are converted to the title compound.

Biological data for the compounds of the present invention was generated by use of the following assays.

VEGFR2 Kinase Assay

Biochemical KDR kinase assays were performed in 96 well microtiter plates that were coated overnight with 75 µg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 2.7 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of 0-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

VEGFR2 Cellular Assay

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 384-well fibronectin coated black-walled plates overnight @ 37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 uM) or at concentrations ranging from 0.0001 to 10.0 uM followed by $VEGF_{165}$ stimulation (10 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of VEGF stimulated responses in the absence of inhibitor.

PDGFRβ Kinase Assay

Biochemical PDGFRβ kinase assays were performed in 96 well microtiter plates that were coated overnight with 75 μg of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 36 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain PDGFR-b protein (Millipore). Following a 60 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

PDGFRβ Cellular Assay

Automated FLIPR (Fluorometric Imaging Plate Reader) technology was used to screen for inhibitors of PDGF-induced increases in intracellular calcium levels in fluorescent dye loaded endothelial cells. NHDF-Ad (Normal Human Dermal Fibroblasts, Adult; Lonza) were seeded in 384-well fibronectin coated black-walled plates overnight @ 37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 uM) or at concentrations ranging from 0.0001 to 10.0 uM followed by PDGF-BB stimulation (30 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of PDGF-BB stimulated responses in the absence of inhibitor.

The biological results for the various compounds are shown in Table 6-10 below.

| Example | Structure | VEGFR2 Enzyme Assay ($IC_{50}$ nM) | VEGFR2 Cellular Assay ($IC_{50}$ nM) | PDGFRβ Enzyme Assay ($IC_{50}$ nM) | PDGFRβ Cellular Assay ($IC_{50}$ nM) |
|---|---|---|---|---|---|
| 1 | [structure] | 6 | 1 | 16 | 11 |

-continued

| Example | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 2 | 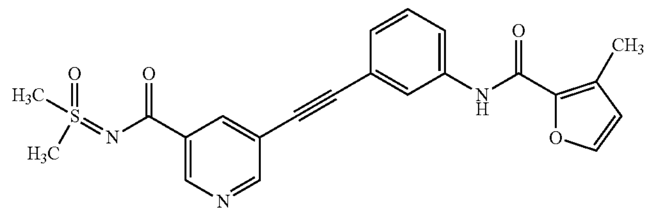 [SMILES: Cc1ccoc1C(=O)Nc1cccc(C#Cc2cncc(C(=O)N=S(C)(C)=O)c2)c1] | 2 | 6 | 6 | |
| 3 | 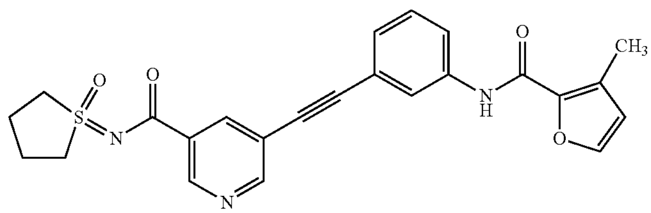 [SMILES: Cc1ccoc1C(=O)Nc1cccc(C#Cc2cncc(C(=O)N=S3(=O)CCCC3)c2)c1] | 2 | 3 | 34 | 66 |
| 4 | 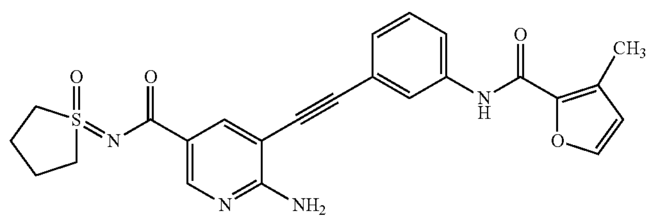 [SMILES: Cc1ccoc1C(=O)Nc1cccc(C#Cc2cc(C(=O)N=S3(=O)CCCC3)cnc2N)c1] | 2 | 2 | 30 | 15 |
| 5 | 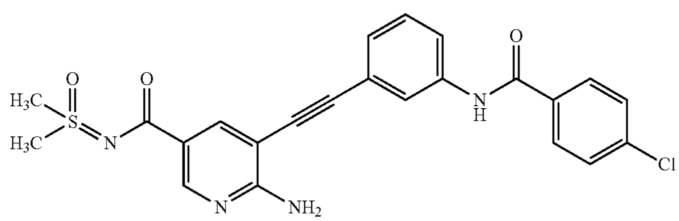 | 2 | 9 | 22 | |
| 6 | 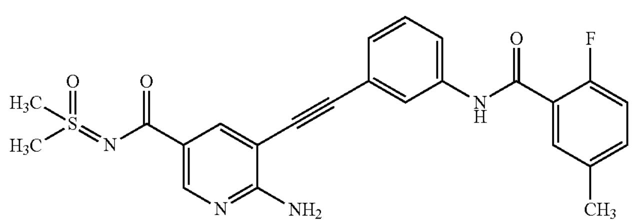 [SMILES: Cc1ccc(F)c(C(=O)Nc2cccc(C#Cc3cc(C(=O)N=S(C)(C)=O)cnc3N)c2)c1] | 7 | 5 | 7 | 10 |
| 7 | 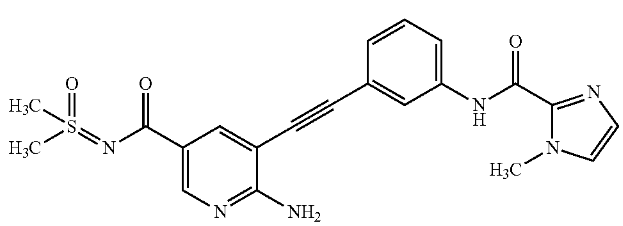 [SMILES: Cn1ccnc1C(=O)Nc1cccc(C#Cc2cc(C(=O)N=S(C)(C)=O)cnc2N)c1] | 6 | 51 | | |

-continued
| Example | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 8 | 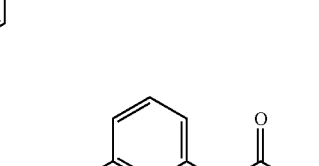 | 3 | 10 | | 28 |
| 9 | 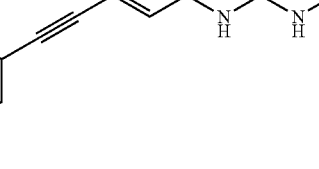 | 8 | 48 | | |
| 10 | 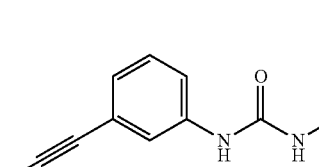 | 8 | 11 | | 19 |
| 11 | 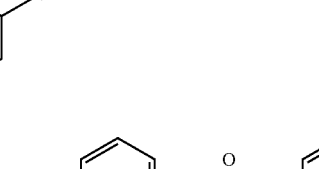 | 6 | 15 | | 19 |
| 12 | 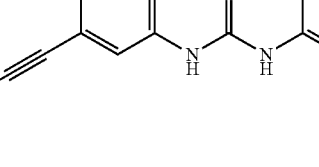 | 3 | 3 | | |
| 13 | 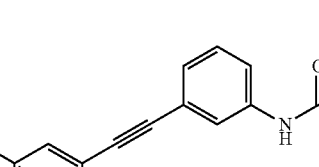 | 9 | 10 | | |

-continued

| Example | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 14 | 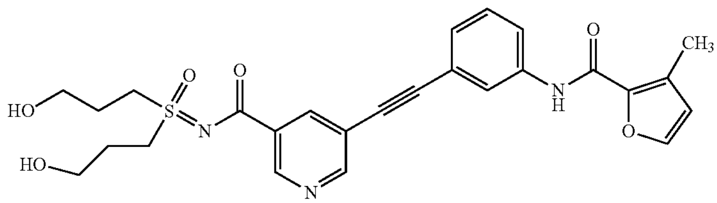 [SMILES: Cc1ccoc1C(=O)Nc1cccc(C#Cc2cncc(C(=O)N=S(=O)(CCCO)CCCO)c2)c1] | 5 | | 26 | |
| 15 | 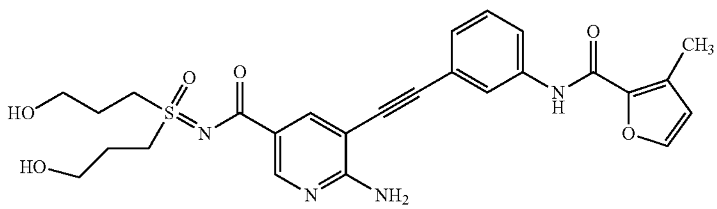 [SMILES: Cc1ccoc1C(=O)Nc1cccc(C#Cc2cc(C(=O)N=S(=O)(CCCO)CCCO)cnc2N)c1] | 3 | | 16 | |
| 16 | 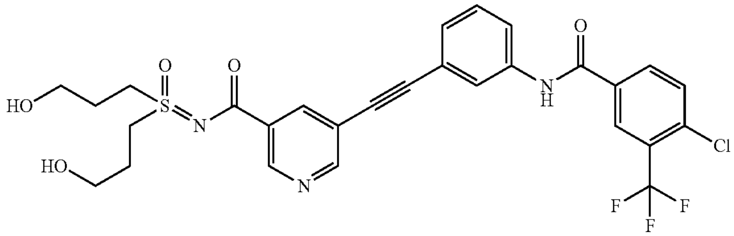 [SMILES: O=C(N=S(=O)(CCCO)CCCO)c1cncc(C#Cc2cccc(NC(=O)c3ccc(Cl)c(C(F)(F)F)c3)c2)c1] | 3 | | | |
| 17 | 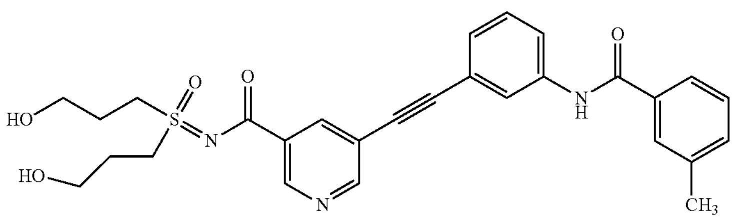 [SMILES: Cc1cccc(C(=O)Nc2cccc(C#Cc3cncc(C(=O)N=S(=O)(CCCO)CCCO)c3)c2)c1] | 3 | | 6 | |
| 18 | 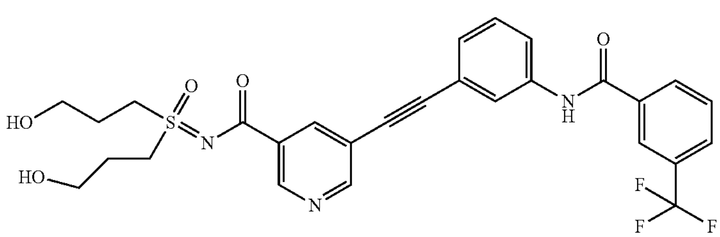 [SMILES: O=C(N=S(=O)(CCCO)CCCO)c1cncc(C#Cc2cccc(NC(=O)c3cccc(C(F)(F)F)c3)c2)c1] | 4 | | | |
| 19 | 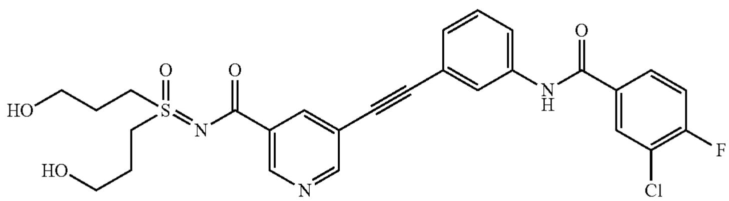 [SMILES: O=C(N=S(=O)(CCCO)CCCO)c1cncc(C#Cc2cccc(NC(=O)c3ccc(F)c(Cl)c3)c2)c1] | 5 | | | |

-continued

| Example | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 20 | 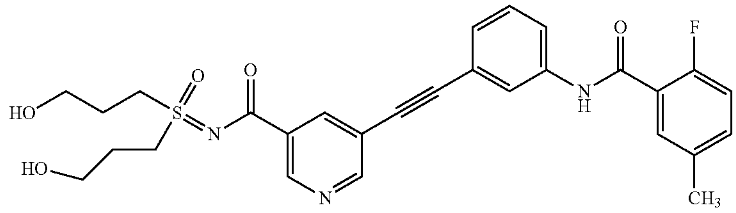 [SMILES: Cc1ccc(F)c(C(=O)Nc2cccc(C#Cc3cncc(C(=O)N=S(=O)(CCCO)CCCO)c3)c2)c1] | 9 | | | |
| 21 | 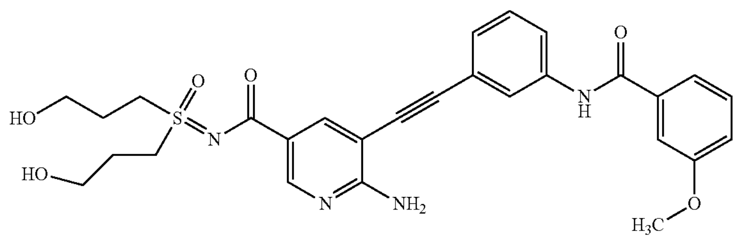 [SMILES: COc1cccc(C(=O)Nc2cccc(C#Cc3cc(C(=O)N=S(=O)(CCCO)CCCO)cnc3N)c2)c1] | 5 | | | |
| 22 | 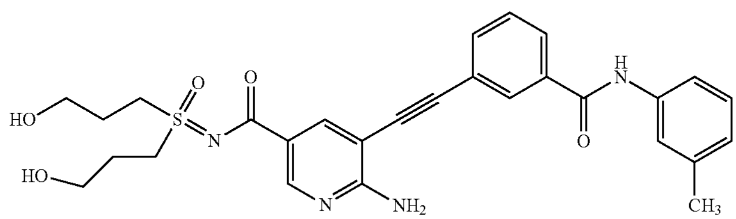 [SMILES: Cc1cccc(NC(=O)c2cccc(C#Cc3cc(C(=O)N=S(=O)(CCCO)CCCO)cnc3N)c2)c1] | 3 | 8 | | |
| 23 | 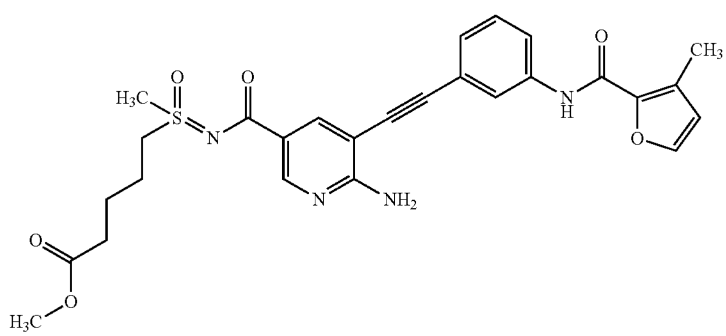 [SMILES: COC(=O)CCCCS(C)(=O)=NC(=O)c1cnc(N)c(C#Cc2cccc(NC(=O)c3occc3C)c2)c1] | 7 | 1 | 54 | 31 |
| 24 | 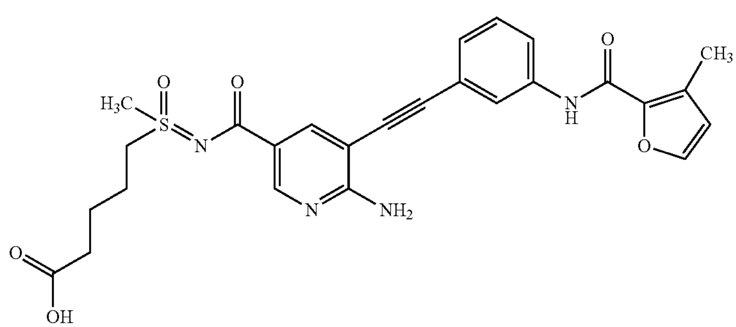 [SMILES: Cc1ccoc1C(=O)Nc1cccc(C#Cc2cc(C(=O)N=S(C)(=O)CCCCC(=O)O)cnc2N)c1] | 5 | 46 | | |

-continued

| Example | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 25 | 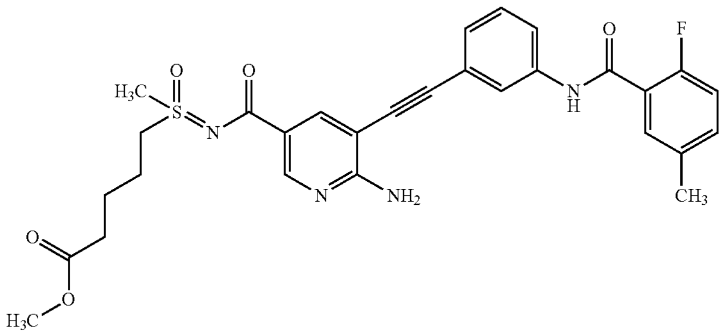 | 8 | | 45 | 27 |
| 26 | 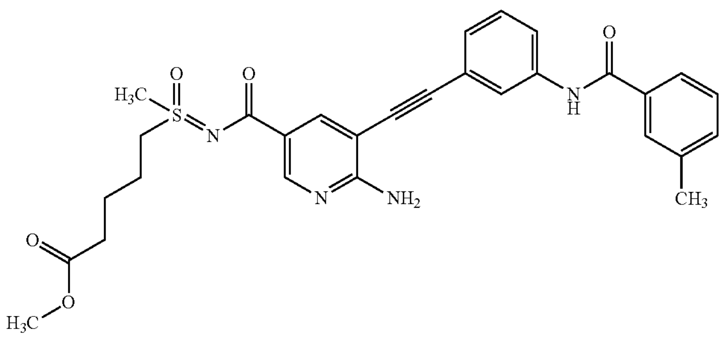 | 4 | 1 | 11 | 10 |
| 27 | 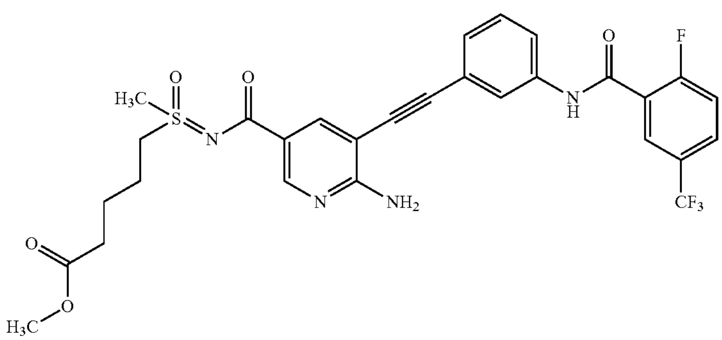 [SMILES: COC(=O)CCCCS(C)(=O)=NC(=O)c1cnc(N)c(C#Cc2cccc(NC(=O)c3cc(C(F)(F)F)ccc3F)c2)c1] | 10 | 1 | 40 | 19 |
| 28 | 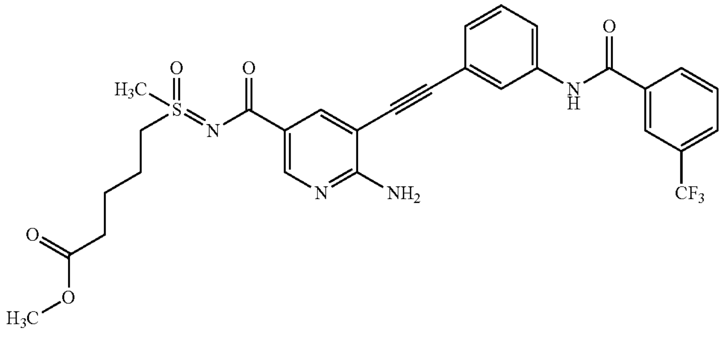 [SMILES: COC(=O)CCCCS(C)(=O)=NC(=O)c1cnc(N)c(C#Cc2cccc(NC(=O)c3cccc(C(F)(F)F)c3)c2)c1] | 4 | 4 | 9 | 12 |

-continued

| Example | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 29 | 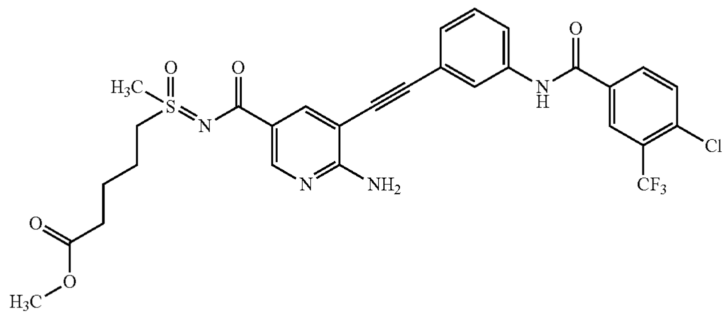 [SMILES: COC(=O)CCCCS(C)(=O)=NC(=O)c1cnc(N)c(C#Cc2cccc(NC(=O)c3ccc(Cl)c(C(F)(F)F)c3)c2)c1] | 4 | 6 | 25 | 15 |
| 30 | 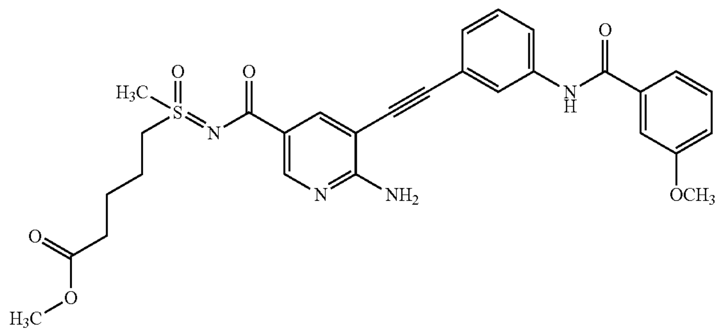 [SMILES: COC(=O)CCCCS(C)(=O)=NC(=O)c1cnc(N)c(C#Cc2cccc(NC(=O)c3cccc(OC)c3)c2)c1] | 5 | 1 | 14 | 9 |
| 31 | 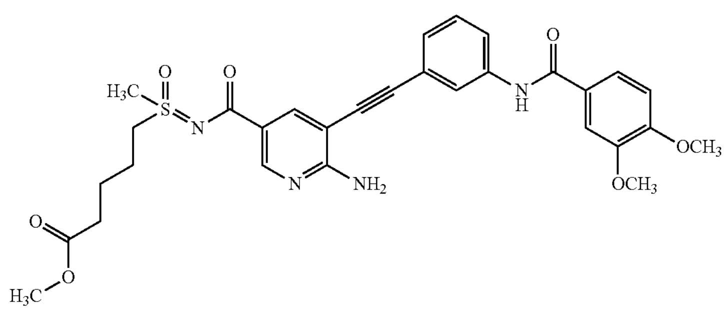 [SMILES: COC(=O)CCCCS(C)(=O)=NC(=O)c1cnc(N)c(C#Cc2cccc(NC(=O)c3ccc(OC)c(OC)c3)c2)c1] | 15 | 4 | 38 | 13 |
| 32 | 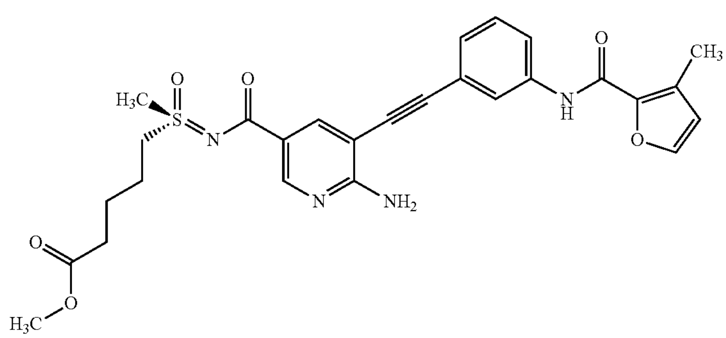 [SMILES: COC(=O)CCCC[S@](C)(=O)=NC(=O)c1cnc(N)c(C#Cc2cccc(NC(=O)c3occc3C)c2)c1] | 3 | 1 | 31 | 60 |

-continued

| Example | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 33 | 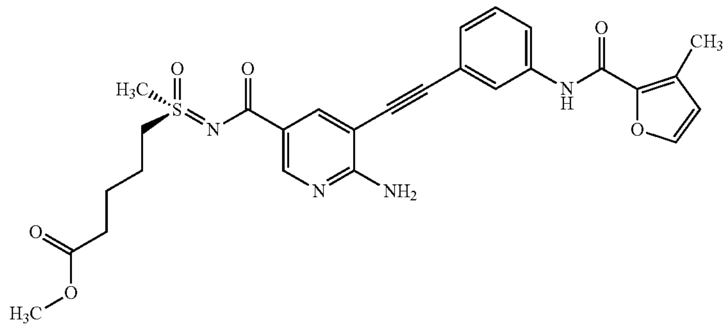 [SMILES: COC(=O)CCCC[S@@](C)(=O)=NC(=O)c1cnc(N)c(C#Cc2cccc(NC(=O)c3occc3C)c2)c1] | 6 | 1 | 27 | 86 |
| 34 | 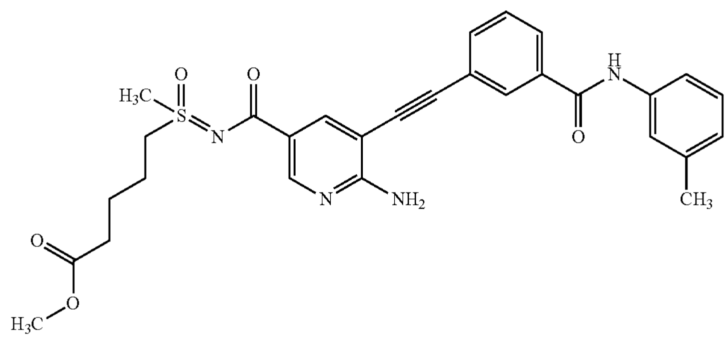 [SMILES: COC(=O)CCCCS(C)(=O)=NC(=O)c1cnc(N)c(C#Cc2cccc(C(=O)Nc3cccc(C)c3)c2)c1] | 7 | 2 | 15 | 13 |
| 35 | 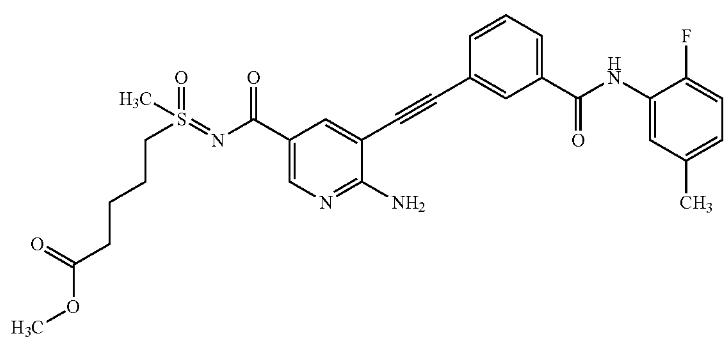 [SMILES: COC(=O)CCCCS(C)(=O)=NC(=O)c1cnc(N)c(C#Cc2cccc(C(=O)Nc3cc(C)ccc3F)c2)c1] | 17 | | | 43 |
| 36 | 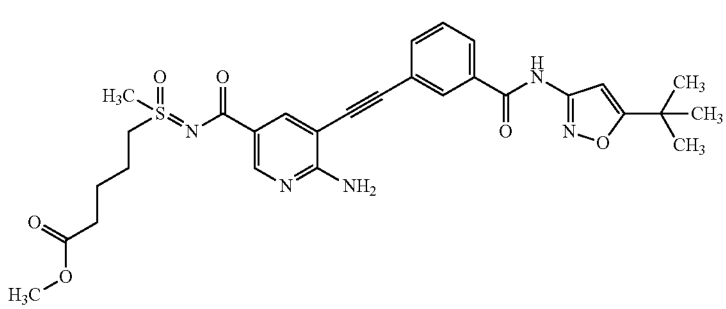 [SMILES: COC(=O)CCCCS(C)(=O)=NC(=O)c1cnc(N)c(C#Cc2cccc(C(=O)Nc3cc(C(C)(C)C)on3)c2)c1] | 10 | 1 | | 18 |

-continued
| Example | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 37 | 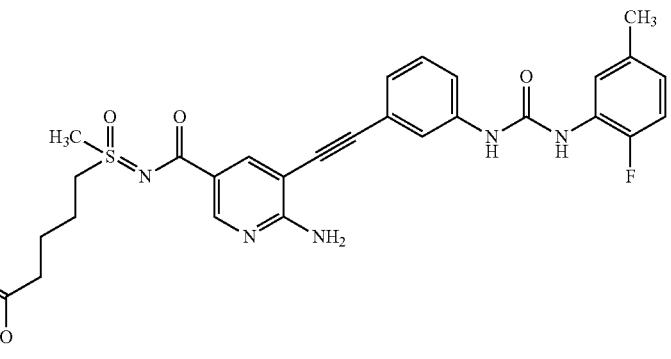 | 5 | | 14 | 44 |
| 38 | 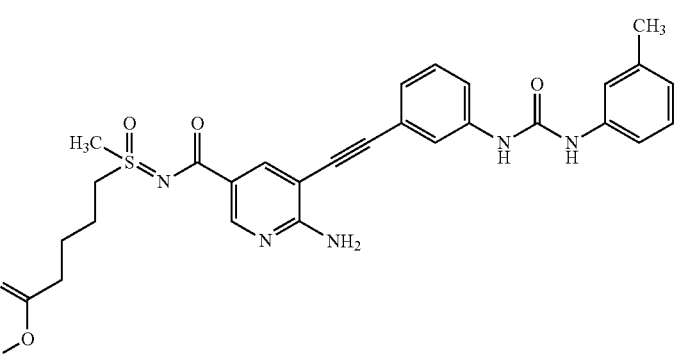 | 4 | | 13 | 25 |
| 39 | 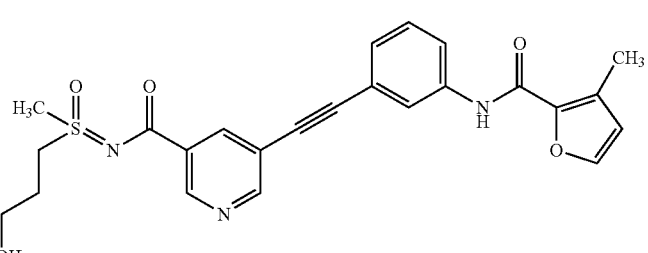 | 14 | 1 | 13 | 31 |
| 40 | 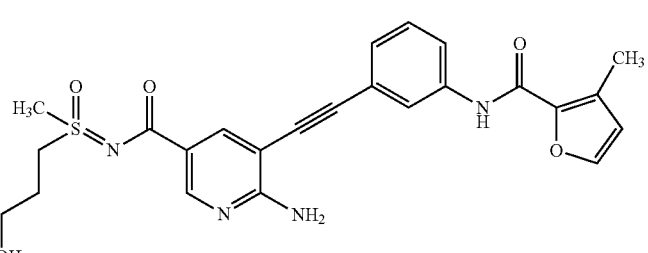 | 3 | 2 | | |
| 41 | 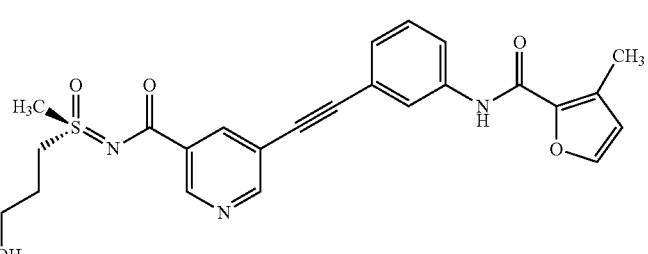 | 3 | | 18 | |

| Example | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 42 | 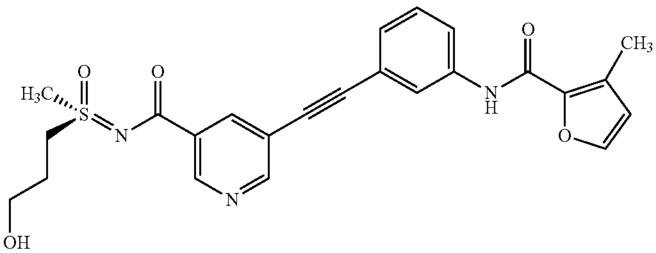 [SMILES: Cc1ccoc1C(=O)Nc1cccc(C#Cc2cncc(C(=O)N=[S@](C)(=O)CCCO)c2)c1] | | 5 | | 13 |

As can be seen from the above Tables, all of the compounds are quite potent at VEGFR2 and PDGFRβ. In particular, the compounds of Examples 23, 26, 30, 32, 33 and 34 are preferred as they have good in vivo efficacy when dosed by intravitreal injection in the VEGF permeability model. (See See J. L. Edelmen, Experimental Eye Research 80 (2005), 249-258.) The compounds of Examples 39 to 41 are also preferred as they have good efficacy when administered by topical delivery in a topical corneal angiogenesis model ("Inhibition of Corneal Neovascularization by Topical Bevacizumab (Anti-VEGF) and Sunitinib (Anti-VEGF and Anti-PDGF) in an Animal Model", by Juan J. Perez-Sanonja et. al. American Journal of Ophthalmology (2010), 150(4), 519-528) In particular, Example 41 is most preferred as it demonstrated the greatest degree of topical efficacy in the above corneal neovascularization model.

The present invention is not to be limited in scope by the exemplified embodiments which are intended as illustrations of single aspects of the invention only. Indeed, various modifications of the invention in addition to those described herein will become apparent to those skilled in the art from the foregoing description. Such modifications are intended to fall within the scope of the appended claims.

All references cited herein are hereby incorporated by reference in their entirety. Also, the compounds of the present invention may be tested by the various in-vitro and in-vivo assays disclosed in such references to demonstrate the claimed utilities.

We claim:
1. A compound of formula I:

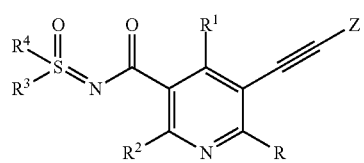

or a pharmaceutically acceptable salt thereof, wherein:
Z is

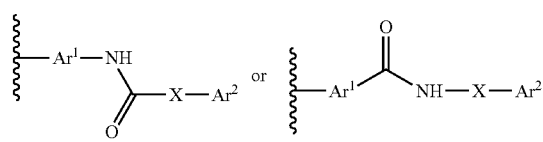

wherein X is absent or X is selected from the group consisting of O, NH and CH$_2$;

R is selected from the group consisting of hydrogen, amino and lower alkyl;

R$^1$ is selected from the group consisting of hydrogen, halogen, lower alkyl, CF$_3$, alkoxy, OCF$_3$, CN and N(R$^5$)$_2$;

R$^2$ is selected from the group consisting of hydrogen, amino and lower alkyl;

R$^3$ and R$^4$ are independently selected from the group consisting of hydrogen, C$_1$ to C$_8$ alkyl, (CR$^5$R$^6$)$_a$C(O)OR$^7$, (CR$^5$R$^6$)$_a$OR$^7$, (CR$^5$R$^6$)$_a$N(R$^5$)C(O)R$^7$, (CR$^5$R$^6$)$_a$C(O)N(R$^7$)$_2$, (CR$^5$R$^6$)$_a$N(R$^5$)C(O)OR$^7$, (CR$^5$R$^6$)$_a$N(R$^5$)C(O)N(R$^7$)$_2$, (CR$^5$R$^6$)$_a$N(R$^7$)$_2$, wherein N(R$^7$)$_2$ may be taken together to form a 3 to 7 membered heterocyclic ring optionally substituted with one or more of R$^5$ and wherein when one of R$^3$ and R$^4$ is selected from the group consisting of, (CR$^5$R$^6$)$_a$C(O)OR$^7$, (CR$^5$R$^6$)$_a$OR$^7$, (CR$^5$R$^6$)$_a$C(O)N(R$^7$) and (CR$^5$R$^6$)$_a$N(R$^7$)$_2$, then the other may not be aryl, and wherein when one of R$^3$ and R$^4$ is (CR$^5$R$^6$)$_a$C(O)OR$^7$, then the other may not be (CR$^5$R$^6$)$_a$C(O)OR$^7$, or R$^3$ and R$^4$ may be taken together with the sulfur atom to form a 4 to 7 membered heterocyclic ring containing one or more heteroatoms optionally substituted by one or more of R$^9$;

R$^5$ is selected from the group consisting of hydrogen, C$_1$ to C$_8$ alkyl, fluoro, hydroxy, hydroxymethyl, COCH$_3$, CH$_2$CH$_2$OH, CH$_2$CH$_2$CH$_2$OH and CH$_2$CH$_2$OCH$_2$CH$_2$OH;

R$^6$ is selected from the group consisting of hydrogen, C$_1$ to C$_8$ alkyl, hydroxy and fluoro;

R$^7$ is selected from the group consisting of hydrogen, C$_1$ to C$_8$ alkyl, fluoro, hydroxy, hydroxymethyl, COCH$_3$, CH$_2$CH$_2$OH and CH$_2$CH$_2$CH$_2$OH;

R$^9$ is selected from the group consisting of hydrogen, C$_1$ to C$_8$ alkyl, (CR$^5$R$^6$)$_a$C(O)OR$^7$, (CR$^5$R$^6$)$_a$OR$^7$, (CR$^5$R$^6$)$_a$N(R$^5$)C(O)R$^7$, (CR$^5$R$^6$)$_a$C(O)N(R$^7$)$_2$, (CR$^5$R$^6$)$_a$N(R$^5$)C(O)OR$^7$, (CR$^5$R$^6$)$_a$N(R$^5$)C(O)N(R$^7$)$_2$, (CR$^5$R$^6$)$_a$N(R$^7$)$_2$, (CR$^5$R$^6$)$_a$C(O)N(R$^5$)(CR$^5$R$^6$)$_a$C(O)OR$^7$, (CR$^5$R$^6$)$_a$C(O)N(R$^5$)(CR$^5$R$^6$)$_a$C(O)N(R$^7$)$_2$, wherein N(R$^7$)$_2$ may be taken together to form a 3 to 7 membered heterocyclic ring containing one or more heteroatoms;

Ar$^1$ and Ar$^2$ are independently selected from the group consisting of

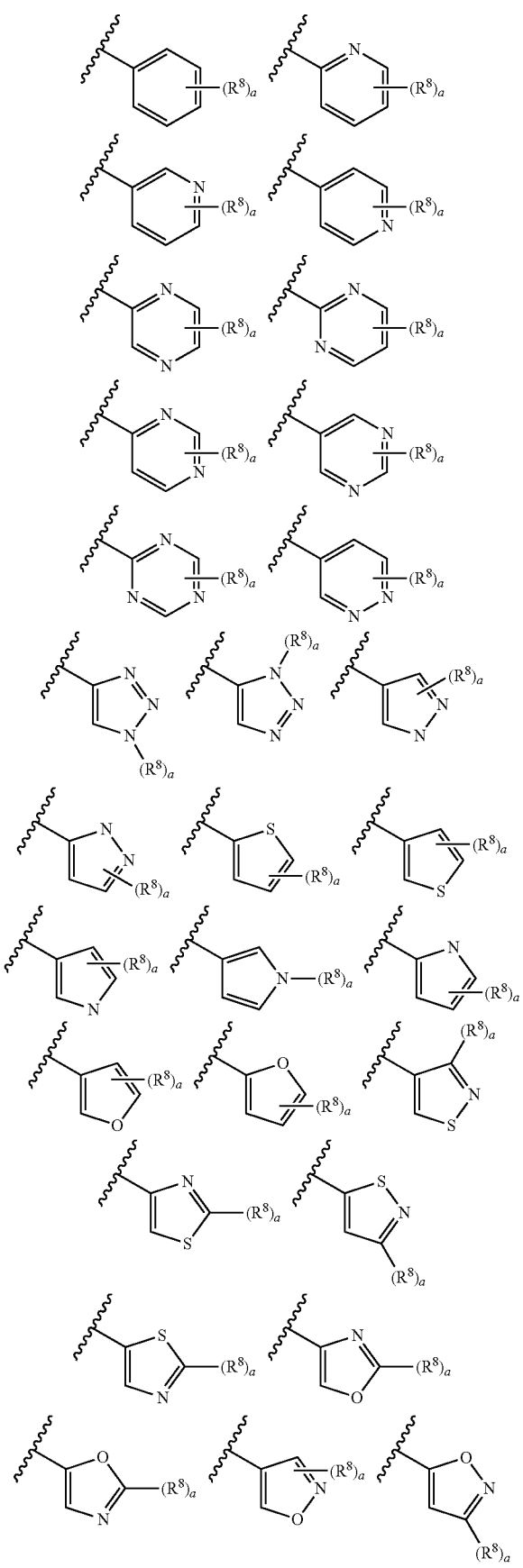

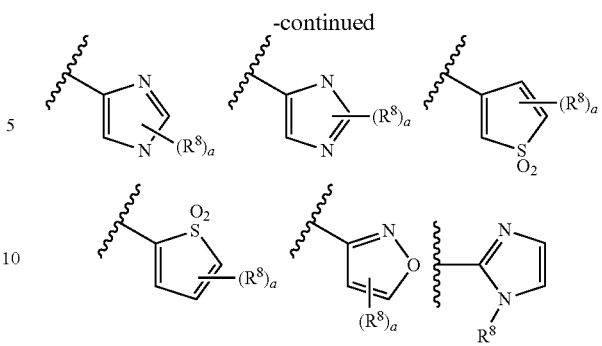

wherein $R^8$ is selected from the group consisting of hydrogen, alkyl, amino, hydroxyl, alkoxy, halogen and $CF_3$; and a is 0 or an integer of from 1 to 4.

2. The compound of claim 1 wherein $Ar^1$ is phenyl.

3. The compound of claim 1 wherein $Ar^2$ is selected from the group consisting of phenyl, furanyl, oxazoyl, diazinyl and mono and disubstituted derivatives thereof wherein the substituent may be selected from the group consisting of halogen, alkyl, alkyloxy and trifluoromethyl.

4. The compound of claim 3 wherein said $Ar^2$ substituent is selected from the group consisting of fluoro, chloro, methyl, ethyl, methyloxy, t-butyloxy and trifluoromethyl.

5. The compound of claim 1 wherein $Ar^2$ is selected from the group consisting of 3-methylfuranyl, 2-fluoro 5-methylphenyl, 4-chloro 5-t-butylphenyl, 3-methoxyphenyl and 5-butyloxazoyl.

6. The compound of claim 1 wherein $R^2$ is H.

7. The compound of claim 1 that is selected from the group consisting of 6-amino-N-[dimethyl(oxido)-$\lambda^4$-sulfanylidene]-5-({3-[(3-methyl-2-furoyl)amino]phenyl}ethynyl)nicotinamide, N-[dimethyl(oxido)-$\lambda^4$-sulfanylidene]-5-({3-[(3-methyl-2-furoyl)amino]phenyl}ethynyl)nicotinamide, 5-({3-[(3-methyl-2-furoyl)amino]phenyl}ethynyl)-N-(1-oxidotetrahydro-1H-1$\lambda^4$-thien-1-ylidene)nicotinamide, 6-amino-5-({3-[(3-methyl-2-furoyl)amino]phenyl}ethynyl)-N-(1-oxidotetrahydro-1H-1$\lambda^4$-thien-1-ylidene)nicotinamide, 6-amino-5-({3-[(4-chlorobenzoyl)amino]phenyl}ethynyl)-N-[dimethyl(oxido)-$\lambda^4$-sulfanylidene]nicotinamide, 6-amino-N-[dimethyl(oxido)-$\lambda^4$-sulfanylidene]-5-({3-[(2-fluoro-5-methylbenzoyl)amino]phenyl}ethynyl)nicotinamide, 6-amino-N-[dimethyl(oxido)-$\lambda^4$-sulfanylidene]-5-[(3-{[(1-methyl-1H-imidazol-2-yl)carbonyl]amino}phenyl)ethynyl]nicotinamide, N-[dimethyl(oxido)-$\lambda^4$-sulfanylidene]-5-{[3-({[(2-fluoro-5-methylphenyl)amino]carbonyl}amino)phenyl]ethynyl}nicotinamide, N-[dimethyl(oxido)-$\lambda^4$-sulfanylidene]-5-{[3-({[(2-fluorophenyl)amino]carbonyl}amino)phenyl]ethynyl}nicotinamide, N-[dimethyl(oxido)-$\lambda^4$-sulfanylidene]-5-{[3-({[(3-methylphenyl)amino]carbonyl}amino)phenyl]ethynyl}nicotinamide, N-[dimethyl(oxido)-$\lambda^4$-sulfanylidene]-5-{[3-({[(4-methylphenyl)amino]carbonyl}amino)phenyl]ethynyl}nicotinamide, 6-amino-N-{[2-(3-hydroxypyrrolidin-1-yl)-2-oxoethyl](methyl)oxido-$\lambda^4$-sulfanylidene}-5-({3-[(3-methyl-2-furoyl)amino]phenyl}ethynyl)nicotinamide, N-[(3-{4-[2-(2-hydroxyethoxy)ethyl]piperazin-1-yl}propyl)(methyl)oxido-$\lambda^4$-sulfanylidene]-5-({3-[(3-methyl-2-furoyl)amino]phenyl}ethynyl)nicotinamide, N-[bis(3-hydroxypropyl)(oxido)-$\lambda^4$-sulfanylidene]-5-({3-[(3-methyl-2-furoyl)amino]phenyl}ethynyl)nicotinamide, 6-amino-N-[bis(3-hydroxypropyl)(oxido)-$\lambda^4$-sulfanylidene]-5-({3-[(3-methyl-2-furoyl)amino]phenyl}ethynyl)nicotinamide, N-[bis(3-hydroxypropyl)(oxido)-$\lambda^4$-sulfanylidene]-5-[(3-{[4-chloro-3-(trifluoromethyl)benzoyl]amino}phenyl)ethynyl]nicotinamide, N-[bis(3-hydroxypropyl)(oxido)-$\lambda^4$-sulfanylidene]-5-({3-[(3-methylbenzoyl)amino]phenyl}ethynyl)nicotinamide, N-[bis(3-hydroxypropyl)(oxido)-$\lambda^4$-sulfanylidene]-5-[(3-{[3-(trifluoromethyl)benzoyl]amino}phenyl)ethynyl]nicotinamide, N-[bis(3-hydroxypropyl)(oxido)-$\lambda^4$-sulfanylidene]-5-({3-[(3-chloro-4-fluorobenzoyl)amino]phenyl}ethynyl)nicotinamide, N-[bis(3-hydroxypropyl)(oxido)-$\lambda^4$-sulfanylidene]-5-({3-[(2-fluoro 5-methylbenzoyl)amino]phenyl}ethynyl)nicotinamide, 6-amino-N-[bis(3-hydroxypropyl)(oxido)-$\lambda^4$-sulfanylidene]-5-({3-[(3-methoxybenzoyl)amino]phenyl}ethynyl)nicotinamide, 6-amino-N-[bis(3-hydroxypropyl)(oxido)-$\lambda^4$-sulfanylidene]-5-[(3-{[(3-methylphenyl)amino]carbonyl}phenyl)ethynyl]nicotinamide, methyl 5-(N-{[6-amino-5-({3-[(3-methyl-2-furoyl)amino]phenyl}ethynyl)pyridin-3-yl]carbonyl}-S-methylsulfonimidoyl)pentanoate, 5-(N-{[6-amino-5-({3-[(3-methyl-2-furoyl)amino]phenyl}ethynyl)pyridin-3-yl]carbonyl}-S-methylsulfonimidoyl)pentanoic acid, methyl 5-(N-{[6-amino-5-({3-[(2-fluoro-5-methylbenzoyl)amino]phenyl}ethynyl)pyridin-3-yl]carbonyl}-S-methylsulfonimidoyl)pentanoate, methyl 5-(N-{[6-amino-5-({3-[(3-methylbenzoyl)amino]phenyl}ethynyl)pyridin-3-yl]carbonyl}-S-methylsulfonimidoyl)pentanoate, methyl 5-[N-({6-amino-5-[(3-{[2-fluoro-5-(trifluoromethyl)benzoyl]amino}phenyl)ethynyl]pyridin-3-yl}carbonyl)-S-methylsulfonimidoyl]pentanoate, methyl 5-[N-({6-amino-5-[(3-{[3-(trifluoromethyl)benzoyl]amino}phenyl)ethynyl]pyridin-3-yl}carbonyl)-S-methylsulfonimidoyl]pentanoate, methyl 5-[N-({6-amino-5-[(3-{[4-chloro-3-(trifluoromethyl)benzoyl]amino}phenyl)ethynyl]pyridin-3-yl}carbonyl)-S-methylsulfonimidoyl]pentanoate, methyl 5-(N-{[6-amino-5-({3-[(3-methoxybenzoyl)amino]phenyl}ethynyl)pyridin-3-yl]carbonyl}-S-methylsulfonimidoyl)pentanoate, methyl 5-(N-{[6-amino-5-({3-[(3,4-di methoxybenzoyl)amino]phenyl}ethynyl)pyridin-3-yl]carbonyl}-S-methylsulfonimidoyl)pentanoate, (S)-methyl 5-(N-{[6-amino-5-({3-[(3-methyl-2-furoyl)amino]phenyl}ethynyl)pyridin-3-yl]carbonyl}-S-methylsulfonimidoyl)pentanoate, (R)-methyl 5-(N-{[6-amino-5-({3-[(3-methyl-2-furoyl)amino]phenyl}ethynyl)pyridin-3-yl]carbonyl}-S-methylsulfonimidoyl)pentanoate, methyl 5-[N-({6-amino-5-[(3-{[(3-methylphenyl)amino]carbonyl}phenyl)ethynyl]pyridin-3-yl}carbonyl)-S-methylsulfonimidoyl]pentanoate, methyl 5-[N-({6-amino-5-[(3-{[(2-fluoro-5-methylphenyl)amino]carbonyl}phenyl)ethynyl]pyridin-3-yl}carbonyl)-S-methylsulfonimidoyl]pentanoate, methyl 5-[N-({6-amino-5-[(3-{[(5-tert-butylisoxazol-3-yl)amino]carbonyl}phenyl)ethynyl]pyridin-3-yl}carbonyl)-S-methylsulfonimidoyl]pentanoate, methyl 5-{N-[(6-amino-5-{[3-({[(2-fluoro-5-methylphenyl)amino]carbonyl}amino)phenyl]ethynyl}pyridin-3-yl)carbonyl]-S-methylsulfonimidoyl}pentanoate, methyl 5-{N-[(6-amino-5-{[3-({[(3-methylphenyl)amino]carbonyl}amino)phenyl]ethynyl}pyridin-3-yl)carbonyl]-S-methylsulfonimidoyl}pentanoate, N-[(3-hydroxypropyl)(methyl)oxido-$\lambda^4$-sulfanylidene]-5-({3-[(3-methyl-2-furoyl)amino]phenyl}ethynyl)nicotinamide, (R)—N-[(3-hydroxypropyl)(methyl)oxido-$\lambda^4$-sulfanylidene]-5-({3-[(3-methyl-2-furoyl)amino]phenyl}ethynyl)nicotinamide, (S)—N-[(3-hydroxypropyl)(methyl)oxido-$\lambda^4$-sulfanylidene]-5-({3-[(3-methyl-2-furoyl)amino]phenyl}ethynyl)nicotinamide, and 6-amino-N-[(3-hydroxypropyl)(methyl)oxido-$\lambda^4$-sulfanylidene]-5-({3-[(3-methyl-2-furoyl)amino]phenyl}ethynyl)nicotinamide; or a pharmaceutically acceptable salt thereof.

8. The compound of claim 1, that is selected from the group consisting of methyl 5-(N-{[6-amino-5-({3-[(3-methyl-2-furoyl)amino]phenyl}ethynyl)pyridin-3-yl]carbonyl}-S-methylsulfonimidoyl)pentanoate, 5-(N-{[6-amino-5-({3-[(3-methyl-2-furoyl)amino]phenyl}ethynyl)pyridin-3-yl]carbonyl}-S-methylsulfonimidoyl)pentanoic acid, methyl 5-(N-{[6-amino-5-({3-[(2-fluoro-5-methylbenzoyl)amino]phenyl}ethynyl)pyridin-3-yl]carbonyl}-S-methylsulfonimidoyl)pentanoate, methyl 5-(N-{[6-amino-5-({3-[(3-methylbenzoyl)amino]phenyl}ethynyl)pyridin-3-yl]carbonyl}-S-methylsulfonimidoyl)pentanoate, methyl 5-[N-({6-amino-5-[(3-{[2-fluoro-5-(trifluoromethyl)benzoyl]amino}phenyl)ethynyl]pyridin-3-yl}carbonyl)-S-methylsulfonimidoyl]pentanoate, methyl 5-[N-({6-amino-5-[(3-{[3-(trifluoromethyl)benzoyl]amino}phenyl)ethynyl]pyridin-3-yl}carbonyl)-S-methylsulfonimidoyl]pentanoate, methyl 5-[N-({6-amino-5-[(3-{[4-chloro-3-(trifluoromethyl)benzoyl]amino}phenyl)ethynyl]pyridin-3-yl}carbonyl)-S-methylsulfonimidoyl]pentanoate, methyl 5-(N-{[6-amino-5-({3-[(3-methoxybenzoyl)amino]phenyl}ethynyl)pyridin-3-yl]carbonyl}-S-methylsulfonimidoyl)pentanoate, methyl 5-(N-{[6-amino-5-({3-[(3,4-di methoxybenzoyl)amino]phenyl}ethynyl)pyridin-3-yl]carbonyl}-S-methylsulfonimidoyl)pentanoate, (S)-methyl 5-(N-{[6-amino-5-({3-[(3-methyl-2-furoyl)amino]phenyl}ethynyl)pyridin-3-yl]carbonyl}-S-methylsulfonimidoyl)pentanoate, (R)-methyl 5-(N-{[6-amino-5-({3-[(3-methyl-2-furoyl)amino]phenyl}ethynyl)pyridin-3-yl]carbonyl}-S-methylsulfonimidoyl)pentanoate, methyl 5-[N-({6-amino-5-[(3-{[(3-methylphenyl)amino]carbonyl}phenyl)ethynyl]pyridin-3-yl}carbonyl)-S-methylsulfonimidoyl]pentanoate, methyl 5-[N-({6-amino-5-[(3-{[(2-fluoro-5-methylphenyl)amino]carbonyl}phenyl)ethynyl]pyridin-3-yl}carbonyl)-S-methylsulfonimidoyl]pentanoate, methyl 5-[N-({6-amino-5-[(3-{[(5-tert-butylisoxazol-3-yl)amino]carbonyl}phenyl)ethynyl]pyridin-3-yl}carbonyl)-S-methylsulfonimidoyl]pentanoate, methyl 5-{N-[(6-amino-5-{[3-({[(2-fluoro-5-methylphenyl)amino]carbonyl}amino)phenyl]ethynyl}pyridin-3-yl)carbonyl]-S-methylsulfonimidoyl}pentanoate, and methyl 5-{N-[(6-amino-5-{[3-({[(3-methylphenyl)amino]carbonyl}amino)phenyl]ethynyl}pyridin-3-yl)carbonyl]-S-methylsulfonimidoyl}pentanoate; or a pharmaceutically acceptable salt thereof.

9. The compound of claim 1, that is selected from the group consisting of

N-[(3-hydroxypropyl)(methyl)oxido-$\lambda^4$-sulfanylidene]-5-({3-[(3-methyl-2-furoyl)amino]phenyl}ethynyl)nicotinamide, (R)—N-[(3-hydroxypropyl)(methyl)oxido-$\lambda^4$-sulfanylidene]-5-({3-[(3-methyl-2-furoyl)amino]phenyl}ethynyl)nicotinamide, (S)—N-[(3-hydroxypropyl)(methyl)oxido-$\lambda^4$-sulfanylidene]-5-({3-[(3-methyl-2-furoyl)amino]phenyl}ethynyl)nicotinamide, and 6-amino-N-[(3-hydroxypropyl)(methyl)oxido-$\lambda^4$-sulfanylidene]-5-({3-[(3-methyl-2-furoyl)amino]phenyl}ethynyl)nicotinamide; or a pharmaceutically acceptable salt thereof.

10. The compound of claim 1, that is (S)—N-[(3-hydroxypropyl)(methyl)oxido-$\lambda^4$-sulfanylidene]-5-({3-[(3-methyl-2-furoyl)amino]phenyl}ethynyl)nicotinamide, or a pharmaceutically acceptable salt thereof.

11. A method for treating a disease selected from the group consisting of cancer, blood vessel proliferative disorders, fibrotic disorders, mesangial cell proliferative disorders, ophthalmic disease, dermatological indications, and metabolic diseases, the method comprising the step of administering to a subject in need thereof a therapeutically effective amount of at least one compound of formula I

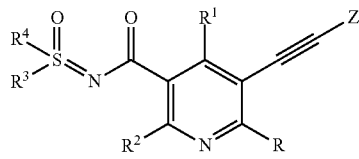

I or a pharmaceutically acceptable salt thereof, wherein:

Z is

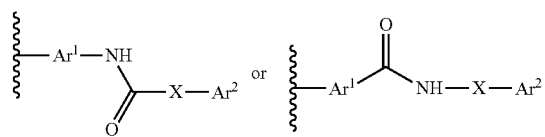

wherein X is absent or X is selected from the group consisting of O, NH and $CH_2$;

R is selected from the group consisting of hydrogen, amino and lower alkyl;

$R^1$ is selected from the group consisting of hydrogen, halogen, lower alkyl, $CF_3$, alkoxy, $OCF_3$, CN and $N(R^5)_2$;

$R^2$ is selected from the group consisting of hydrogen, amino and lower alkyl, $R^3$ and $R^4$ are independently selected from the group consisting of hydrogen, $C_1$ to $C_8$ alkyl, $(CR^5R^6)_aC(O)OR^7$, $(CR^5R^6)_aOR^7$, $(CR^5R^6)_aN(R^5)C(O)R^7$, $(CR^5R^6)_aC(O)N(R^7)_2$, $(CR^5R^6)_aN(R^5)C(O)OR^7$, $(CR^5R^6)_aN(R^5)C(O)N(R^7)_2$, $(CR^5R^6)_aN(R^7)_2$, wherein $N(R^7)_2$ may be taken together to form a 3 to 7 membered heterocyclic ring optionally substituted with one or more of $R^5$ and wherein when one of $R^3$ and $R^4$ is selected from the group consisting of, $(CR^5R^6)_aC(O)OR^7$, $(CR^5R^6)_aOR^7$, $(CR^5R^6)_aC(O)N(R^7)$ and $(CR^5R^6)_aN(R^7)_2$, then the other may not be aryl, and wherein when one of $R^3$ and $R^4$ is $(CR^5R^6)_aC(O)OR^7$, then the other may not be $(CR^5R^6)_aC(O)OR^7$, or $R^3$ and $R^4$ may be taken together with the sulfur atom to form a 4 to 7 membered heterocyclic ring containing one or more heteroatoms optionally substituted by one or more of $R^9$;

$R^5$ is selected from the group consisting of hydrogen, $C_1$ to $C_8$ alkyl, fluoro, hydroxyl, hydroxymethyl, $COCH_3$, $CH_2CH_2OH$, $CH_2CH_2CH_2OH$ and $CH_2CH_2OCH_2CH_2OH$;

$R^6$ is selected from the group consisting of hydrogen, $C_1$ to $C_8$ alkyl, hydroxy and fluoro;

$R^7$ is selected from the group consisting of hydrogen, $C_1$ to $C_8$ alkyl, fluoro, hydroxy, hydroxymethyl, $COCH_3$, $CH_2CH_2OH$ and $CH_2CH_2CH_2OH$;

$R^9$ is selected from the group consisting of hydrogen, $C_1$ to $C_8$ alkyl, $(CR^5R^6)_aC(O)OR^7$, $(CR^5R^6)_aOR^7$, $(CR^5R^6)_aN(R^5)C(O)R^7$, $(CR^5R^6)_aC(O)N(R^7)_2$, $(CR^5R^6)_aN(R^5)C(O)OR^7$, $(CR^5R^6)_aN(R^5)C(O)N(R^7)_2$, $(CR^5R^6)_aN(R^7)_2$, $(CR^5R^6)_aC(O)N(R^5)(CR^5R^6)_aC(O)OR^7$, $(CR^5R^6)_aC(O)N(R^5)(CR^5R^6)_aC(O)N(R^7)_2$, wherein $N(R^7)_2$ may be taken together to form a 3 to 7 membered heterocyclic ring containing one or more heteroatoms;

$Ar^1$ and $Ar^2$ are independently selected from the group consisting of

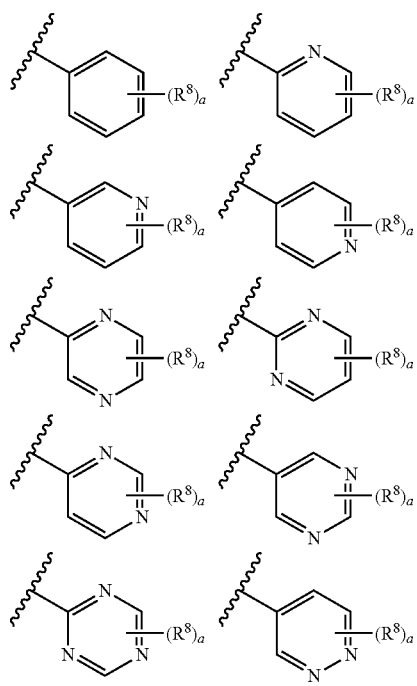

-continued

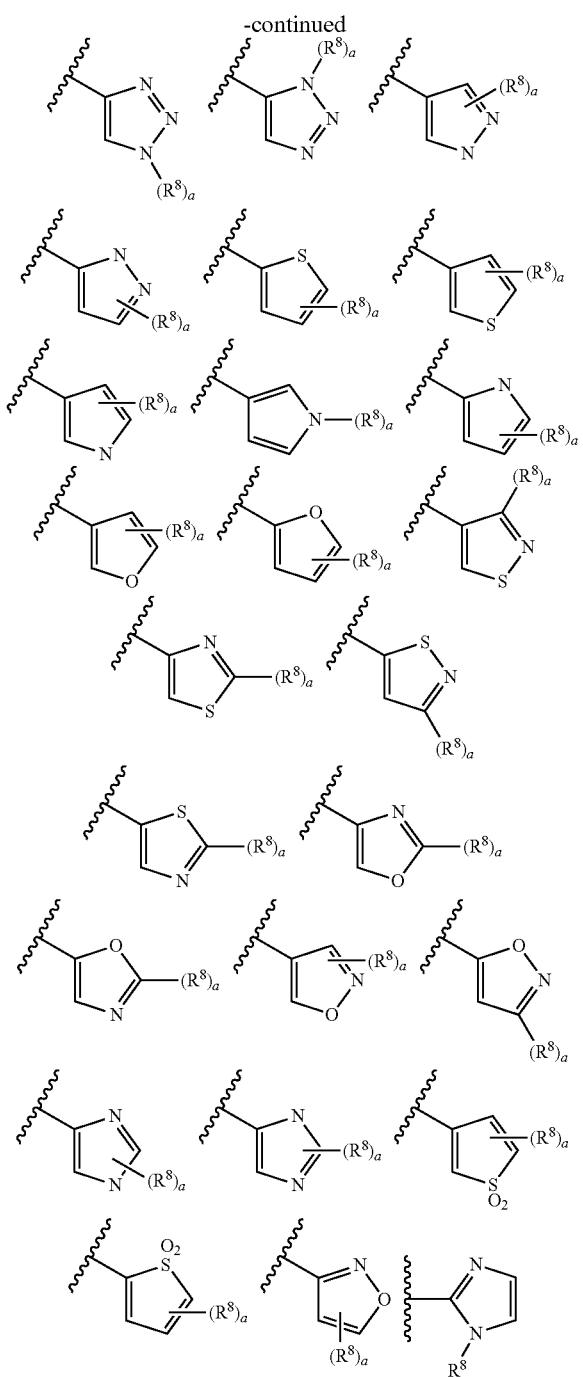

wherein $R^8$ is selected from the group consisting of hydrogen, alkyl, amino, hydroxyl, alkoxy, halogen and $CF_3$; and a is 0 or an integer of from 1 to 4.

12. The method of claim 11 wherein the blood vessel proliferative disorder is selected from the group consisting of diabetic retinopathy, exudative age-related macular degeneration, retinopathy of prematurity, pterigium, rosacea, arthritis and restenosis.

13. The method of claim 11 wherein the fibrotic disorder is selected from the group consisting of hepatic cirrhosis and atherosclerosis.

14. The method of claim 11 wherein the mesangial cell proliferative disorder is selected from the group consisting of glomerulonephritis, diabetic nephropathy, malignant nephrosclerosis, thrombotic microangiopathy syndromes, transplant rejection and glomerulopathies.

15. The method of claim 11 wherein the metabolic disease is selected from the group consisting of psoriasis, diabetes mellitus, wound healing, and neurodegenerative diseases.

16. The method of claim 11 wherein said ophthalmic disease is selected from the group consisting of pterygia, hyperemia related to an actively inflamed pterygia, recurrent pterygia following excisional surgery, progressive pterygia approaching the visual axis, chronic low grade hyperemia associated with pterygia, corneal neovascularization, neovascular glaucoma, iris neovascularization, chronic allergic conjunctivitis, ocular rosacea, blepharoconjunctivitis, recurrent episcleritis, keratoconjunctivitis sicca, ocular graft vs host disease, diabetic retinopathy, diabetic macular edema, proliferative diabetic retinopathy, exudative or neovascular age-related macular degeneration, high-risk eyes with dry age-related macular degeneration, neovascular disease associated with retinal vein occlusion, neovascular disease associated with the following: pathologic myopia, pseudoxanthoma elasticum, optic nerve drusen, traumatic choroidal rupture, idiopathic etiologies, presumed ocular histoplasmosis syndrome, and retinopathy of prematurity.

17. The method of claim 11 wherein said dermatological indication is selected from the group consisting of sun burn, eczema, psoriasis and contact dermatitis.

18. A pharmaceutical composition comprising a pharmaceutically effective amount of at least one compound of formula I

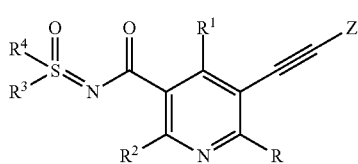

I or a pharmaceutically acceptable salt thereof, wherein:
Z is

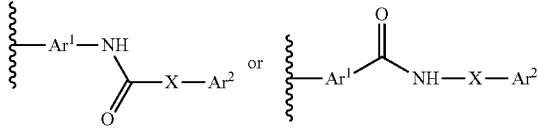

wherein X is absent or X is selected from the group consisting of O, NH and $CH_2$;

R is selected from the group consisting of hydrogen, amino and lower alkyl;

$R^1$ is selected from the group consisting of hydrogen, halogen, lower alkyl, $CF_3$, alkoxy, $OCF_3$, CN and $N(R^5)_2$;

$R^2$ is selected from the group consisting of hydrogen, amino and lower alkyl;

$R^3$ and $R^4$ are independently selected from the group consisting of hydrogen, $C_1$ to $C_8$ alkyl, $(CR^5R^6)_aC(O)OR^7$, $(CR^5R^6)_aOR^7$, $(CR^5R^6)_aN(R^5)C(O)R^7$, $(CR^5R^6)_aC(O)N(R^7)_2$, $(CR^5R^6)_aN(R^5)C(O)OR^7$, $(CR^5R^6)_aN(R^5)C(O)N(R^7)_2$, $(CR^5R^6)_aN(R^7)_2$, wherein $N(R^7)_2$ may be taken together to form a 3 to 7 membered heterocyclic ring optionally substituted with one or more of $R^5$ and wherein when one of $R^3$ and $R^4$ is selected from the group consisting of, $(CR^5R^6)_aC(O)OR^7$, $(CR^5R^6)_aOR^7$, $(CR^5R^6)_aC(O)N(R^7)$ and $(CR^5R^6)_aN(R^7)_2$, then the other may not be aryl, and wherein when one of $R^3$ and $R^4$ is $(CR^5R^6)_aC(O)OR^7$, then the other may not be $(CR^5R^6)_aC(O)OR^7$, or $R^3$ and $R^4$ may be taken together with the sulfur atom to form a 4 to 7 membered carbocyclic or heterocyclic ring containing one or more heteroatoms optionally substituted by one or more of $R^9$;

$R^5$ is selected from the group consisting of hydrogen, $C_1$ to $C_8$ alkyl, fluoro, hydroxy, hydroxymethyl, $COCH_3$, $CH_2CH_2OH$, $CH_2CH_2CH_2OH$ and $CH_2CH_2OCH_2CH_2OH$;

$R^6$ is selected from the group consisting of hydrogen, $C_1$ to $C_8$ alkyl, hydroxy and fluoro;

$R^7$ is selected from the group consisting of hydrogen, $C_1$ to $C_8$ alkyl, fluoro, hydroxy, hydroxymethyl, $COCH_3$, $CH_2CH_2OH$ and $CH_2CH_2CH_2OH$;

$R^9$ is selected from the group consisting of hydrogen, $C_1$ to $C_8$ alkyl, $(CR^5R^6)_aC(O)OR^7$, $(CR^5R^6)_aOR^7$, $(CR^5R^6)_a N(R^5)C(O)R^7$, $(CR^5R^6)_aC(O)N(R^7)_2$, $(CR^5R^6)_aN(R^5)C(O)OR^7$, $(CR^5R^6)_aN(R^5)C(O)N(R^7)_2$, $(CR^5R^6)_aN(R^7)_2$, $(CR^5R^6)_aC(O)N(R^5)(CR^5R^6)_aC(O)OR^7$, $(CR^5R^6)_aC(O)N(R^5)(CR^5R^6)_aC(O)N(R^7)_2$, wherein $N(R^7)_2$ may be taken together to form a heterocyclic ring containing one or more heteroatoms;

$Ar^1$ and $Ar^2$ are independently selected from the group consisting of

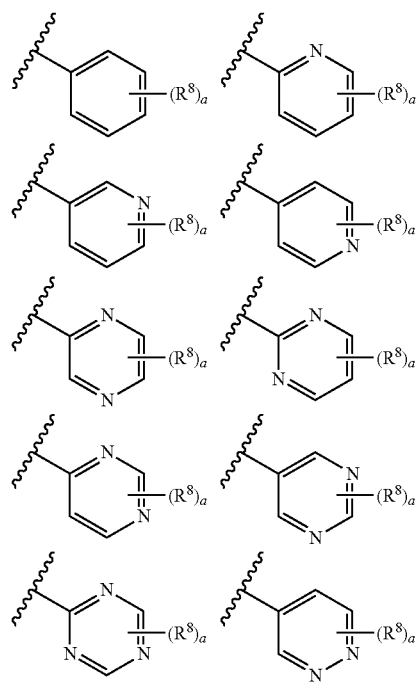

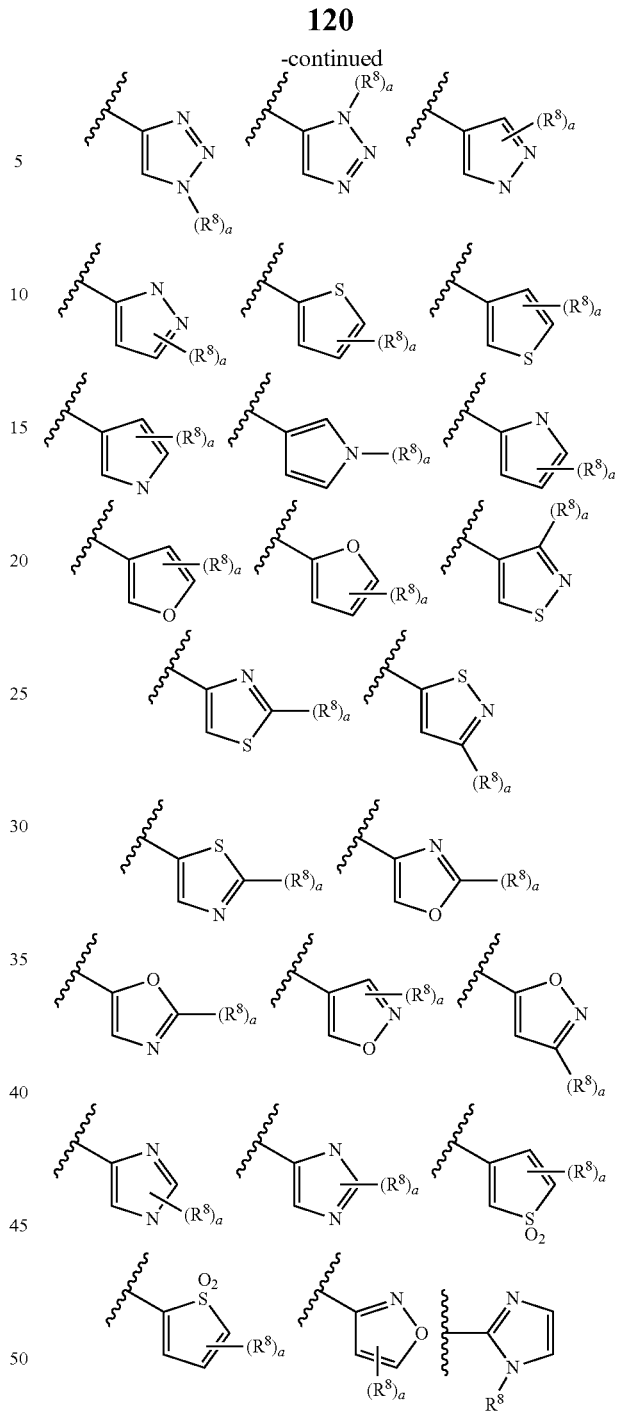

wherein $R^8$ is selected from the group consisting of hydrogen, alkyl, amino, hydroxyl, alkoxy, halogen and $CF_3$; and a is 0 or an integer of from 1 to 4 and a pharmaceutically acceptable carrier or excipient.

* * * * *